(12) United States Patent
Lenker et al.

(10) Patent No.: US 8,425,549 B2
(45) Date of Patent: Apr. 23, 2013

(54) SYSTEMS AND METHODS FOR REMOVING OBSTRUCTIVE MATTER FROM BODY LUMENS AND TREATING VASCULAR DEFECTS

(75) Inventors: Jay A. Lenker, Laguna Beach, CA (US); Brian Michael Strauss, Trabuco Canyon, CA (US); Gerard Von Hoffman, Trabuco Canyon, CA (US)

(73) Assignee: Reverse Medical Corporation, Irvine, CA (US)

( * ) Notice: Subject to any disclaimer, the term of this patent is extended or adjusted under 35 U.S.C. 154(b) by 784 days.

(21) Appl. No.: 12/343,374

(22) Filed: Dec. 23, 2008

(65) Prior Publication Data

US 2010/0114017 A1    May 6, 2010

(51) Int. Cl.
*A61M 29/00* (2006.01)
(52) U.S. Cl.
USPC .......................................... 606/198; 606/200
(58) Field of Classification Search .................. 604/103, 604/99.01–99.04, 93.01, 96.01, 158, 164.01–164.02; 606/198, 200, 191, 192, 194; 600/585
See application file for complete search history.

(56) References Cited

U.S. PATENT DOCUMENTS

| | | | |
|---|---|---|---|
| 2,042,900 A | 6/1936 | James | |
| 4,403,612 A | 9/1983 | Fogarty | |
| 4,601,713 A | 7/1986 | Fuqua | |
| 4,646,736 A | 3/1987 | Auth | |
| 4,692,139 A | 9/1987 | Stiles | |
| 4,706,671 A | 11/1987 | Weinrib | |
| 4,710,181 A | 12/1987 | Fuqua | |
| 4,716,901 A | 1/1988 | Jackson et al. | |
| 4,738,666 A | 4/1988 | Fuqua | |
| 4,739,768 A | 4/1988 | Engelson | |
| 4,798,193 A | 1/1989 | Giesy et al. | |
| 4,820,349 A | 4/1989 | Saab | |
| 4,846,791 A | 7/1989 | Hattler et al. | |
| 5,011,488 A * | 4/1991 | Ginsburg | 606/159 |

(Continued)

FOREIGN PATENT DOCUMENTS

| | | |
|---|---|---|
| EP | 0177177 A2 | 9/1985 |
| EP | 0249456 A2 | 6/1987 |

(Continued)

OTHER PUBLICATIONS

PCT International Search Report and Written Opinion dated Aug. 13, 2010 in PCT Application No. PCT/US2009/069498.

(Continued)

*Primary Examiner* — Theodore Stigell
(74) *Attorney, Agent, or Firm* — K. David Crockett, Esq.; Crockett & Crockett, PC

(57) ABSTRACT

Systems and methods for removing obstructions from, delivering implantable devices or substances in or near and/or restoring flow through body lumens, such as blood vessel lumens. A catheter having a proximal portion of a first diameter and a distal portion of a second diameter (smaller than the first diameter) is advanced into a body lumen. The distal portion of the catheter is caused to expand to a diameter that is larger than the second diameter but no larger than the first diameter. A working device is then advanced out of the distal end of the catheter and used to remove obstructive matter, deliver an implantable device or substance and/or restore flow. The distal portion can be reduced in diameter prior to removal from the body.

18 Claims, 38 Drawing Sheets

U.S. PATENT DOCUMENTS

| | | | |
|---|---|---|---|
| 5,066,285 A | 11/1991 | Hillstead | |
| 5,092,839 A | 3/1992 | Kipperman | |
| 5,158,545 A | 10/1992 | Trudell et al. | |
| 5,176,659 A | 1/1993 | Mancini | |
| 5,183,464 A | 2/1993 | Dubrul et al. | |
| 5,201,756 A | 4/1993 | Horzewski et al. | |
| 5,217,474 A | 6/1993 | Zacca et al. | |
| 5,318,532 A | 6/1994 | Frassica | |
| 5,318,588 A | 6/1994 | Horzewski et al. | |
| 5,336,205 A | 8/1994 | Zenzen et al. | |
| 5,344,402 A | 9/1994 | Crocker | |
| 5,407,430 A | 4/1995 | Peters | |
| 5,431,676 A | 7/1995 | Dubrul et al. | |
| 5,460,170 A | 10/1995 | Hammerslag | |
| 5,474,537 A | 12/1995 | Solar | |
| 5,522,800 A | 6/1996 | Crocker | |
| 5,533,968 A | 7/1996 | Muni et al. | |
| 5,542,926 A | 8/1996 | Crocker | |
| 5,554,136 A | 9/1996 | Luther | |
| 5,571,089 A | 11/1996 | Crocker | |
| 5,573,509 A | 11/1996 | Thornton | |
| 5,599,306 A | 2/1997 | Klein et al. | |
| 5,674,240 A | 10/1997 | Bonutti et al. | |
| 5,704,926 A | 1/1998 | Sutton | |
| 5,728,132 A * | 3/1998 | Van Tassel et al. | 606/213 |
| 5,766,201 A | 6/1998 | Ravenscroft et al. | |
| 5,782,797 A | 7/1998 | Schweich, Jr. et al. | |
| 5,795,322 A * | 8/1998 | Boudewijn | 604/22 |
| 5,827,243 A | 10/1998 | Palestrant | |
| 5,843,050 A | 12/1998 | Jones et al. | |
| 5,846,251 A | 12/1998 | Hart | |
| 5,891,114 A | 4/1999 | Chien et al. | |
| 5,895,398 A | 4/1999 | Wensel et al. | |
| 5,899,890 A | 5/1999 | Chiang et al. | |
| 5,928,260 A * | 7/1999 | Chin et al. | 606/200 |
| 5,938,645 A | 8/1999 | Gordon | |
| 5,957,900 A | 9/1999 | Ouchi | |
| 5,971,938 A | 10/1999 | Hart et al. | |
| 5,972,019 A | 10/1999 | Engelson et al. | |
| 5,997,508 A | 12/1999 | Lunn et al. | |
| 6,044,845 A | 4/2000 | Lewis | |
| 6,090,072 A | 7/2000 | Kratoska et al. | |
| 6,136,016 A * | 10/2000 | Barbut et al. | 606/200 |
| 6,161,547 A | 12/2000 | Barbut | |
| 6,165,199 A | 12/2000 | Barbut | |
| 6,183,443 B1 | 2/2001 | Kratoska et al. | |
| 6,190,357 B1 | 2/2001 | Ferrari et al. | |
| 6,196,994 B1 | 3/2001 | Maahs | |
| 6,290,710 B1 | 9/2001 | Cryer et al. | |
| 6,295,990 B1 | 10/2001 | Lewis et al. | |
| 6,306,124 B1 * | 10/2001 | Jones et al. | 604/509 |
| 6,309,399 B1 | 10/2001 | Barbut et al. | |
| 6,312,374 B1 | 11/2001 | von Hoffmann | |
| 6,312,444 B1 | 11/2001 | Barbut | |
| 6,494,860 B2 | 12/2002 | Rocamora et al. | |
| 6,692,462 B2 | 2/2004 | Mackenzie et al. | |
| 7,217,255 B2 * | 5/2007 | Boyle et al. | 604/104 |
| 2001/0037126 A1 | 11/2001 | Stack et al. | |
| 2002/0010476 A1 | 1/2002 | Mulholland et al. | |
| 2003/0050600 A1 | 3/2003 | Ressemann et al. | |
| 2003/0065353 A1 | 4/2003 | Horzewski et al. | |
| 2003/0097149 A1 | 5/2003 | Edwards et al. | |
| 2003/0212384 A1 | 11/2003 | Hayden | |
| 2004/0006344 A1 | 1/2004 | Nguyen et al. | |
| 2004/0176801 A1 | 9/2004 | Edwards et al. | |
| 2005/0124937 A1 | 6/2005 | Kick et al. | |
| 2005/0137499 A1 | 6/2005 | Sheets et al. | |
| 2007/0293727 A1 | 12/2007 | Goldfarb et al. | |

FOREIGN PATENT DOCUMENTS

| | | |
|---|---|---|
| EP | 0385920 A2 | 2/1990 |
| EP | 0206553 B1 | 1/1991 |
| WO | WO 92/19312 | 11/1992 |
| WO | WO 03/090834 A2 | 11/2003 |

OTHER PUBLICATIONS

USPTO Office Action dated Jun. 30, 2010 in related U.S. Appl. No. 11/936,632, filed Nov. 7, 2007.

USPTO Office Action dated Jan. 8, 2010 in related U.S. Appl. No. 11/936,632, filed Nov. 7, 2007.

USPTO Office Action dated Dec. 3, 2008 in related U.S. Appl. No. 11/936,632, filed Nov. 7, 2007.

* cited by examiner

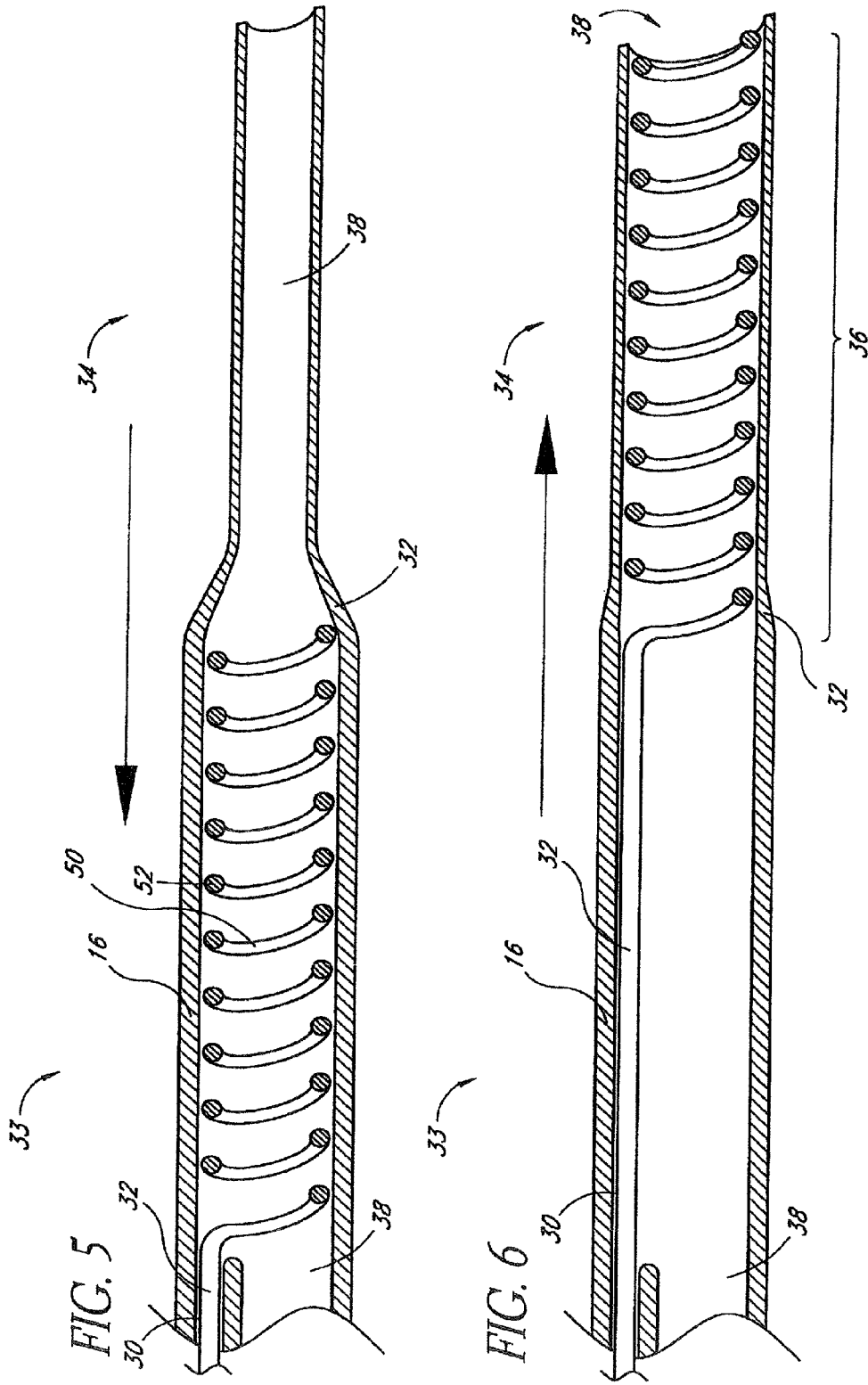

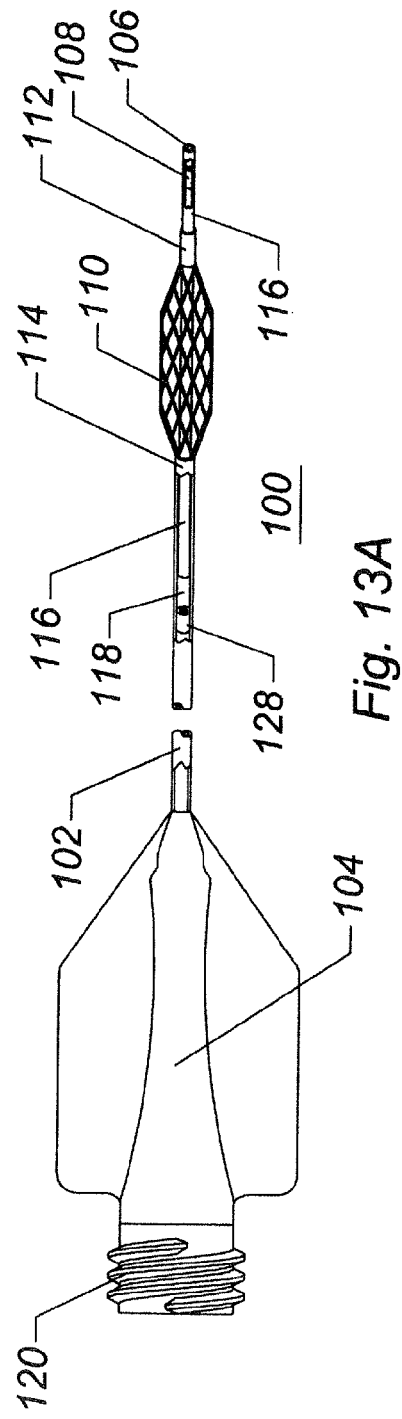
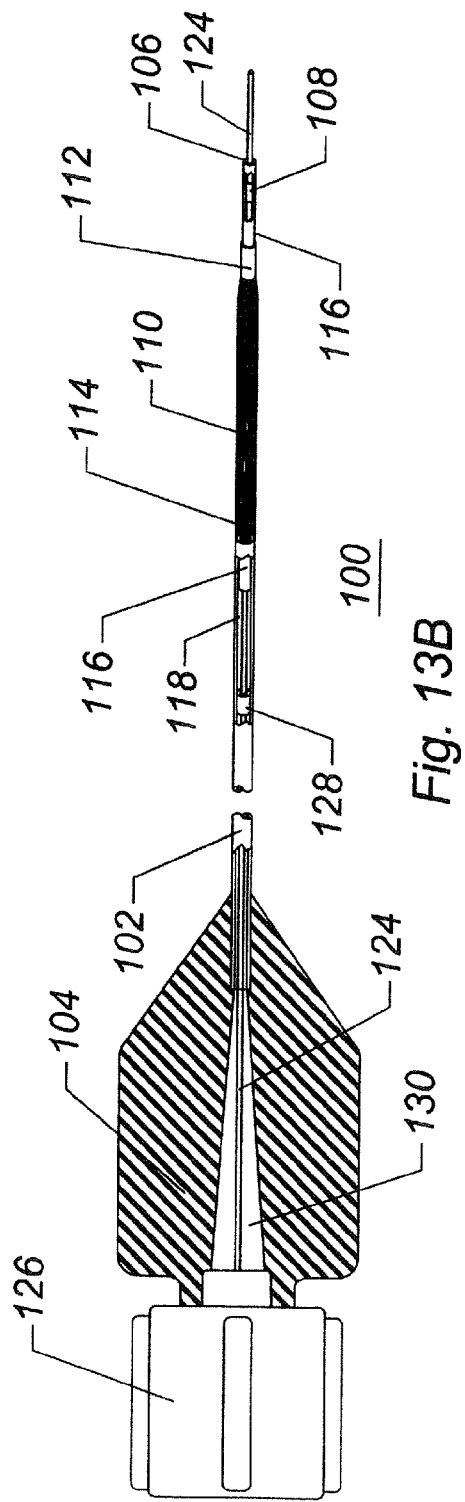
Fig. 13A
Fig. 13B

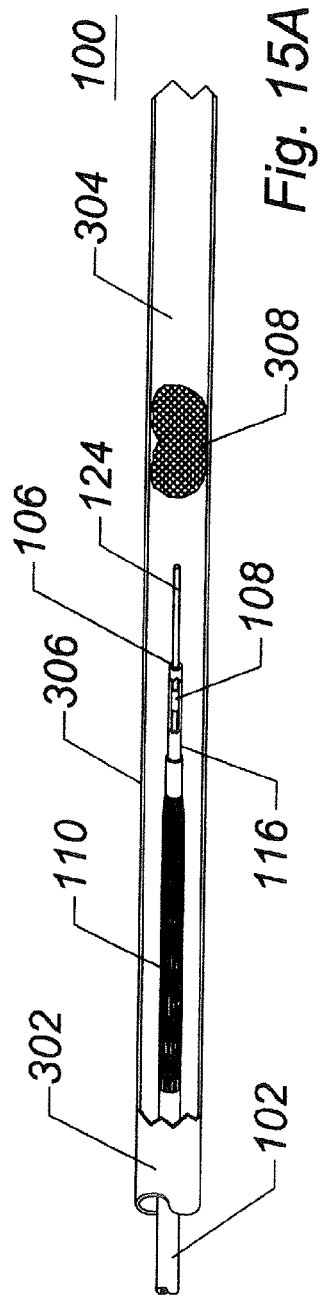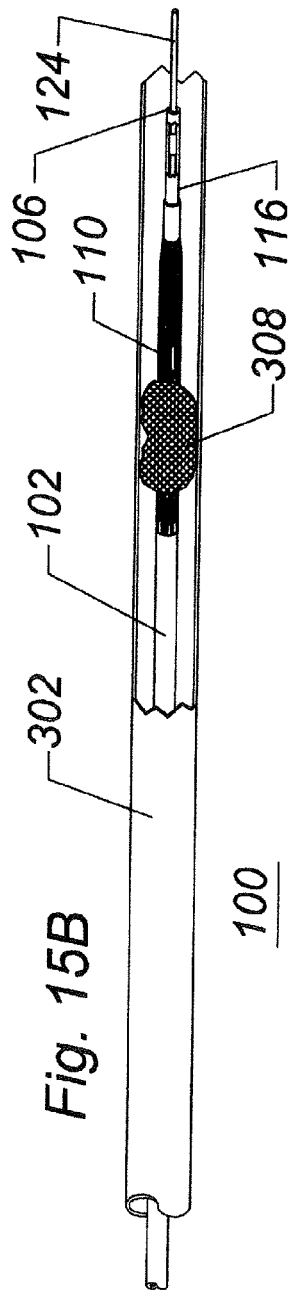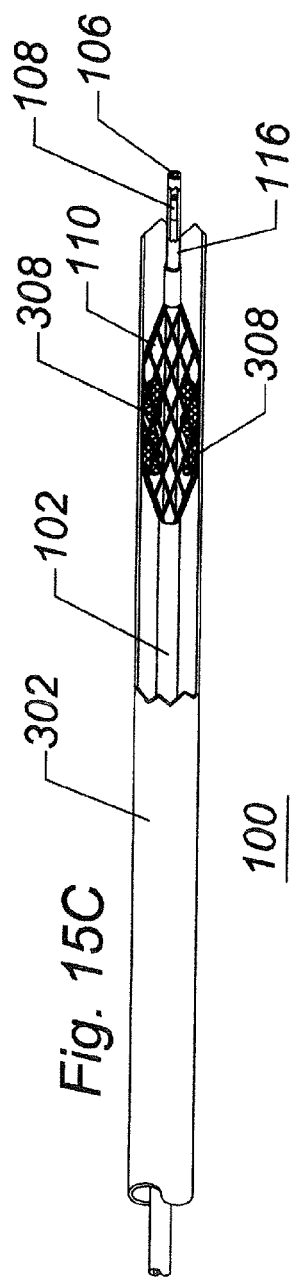

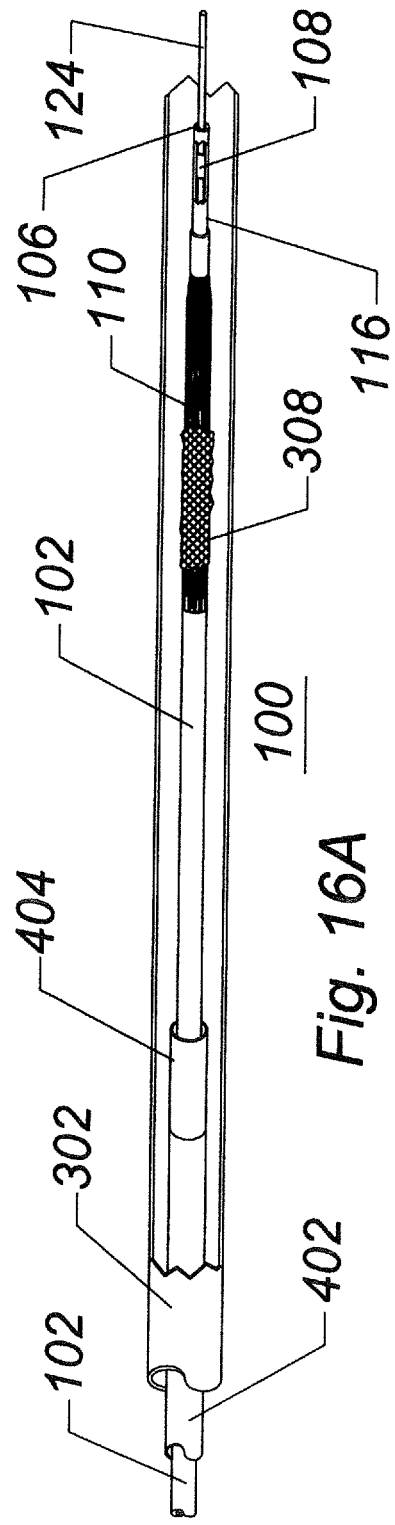
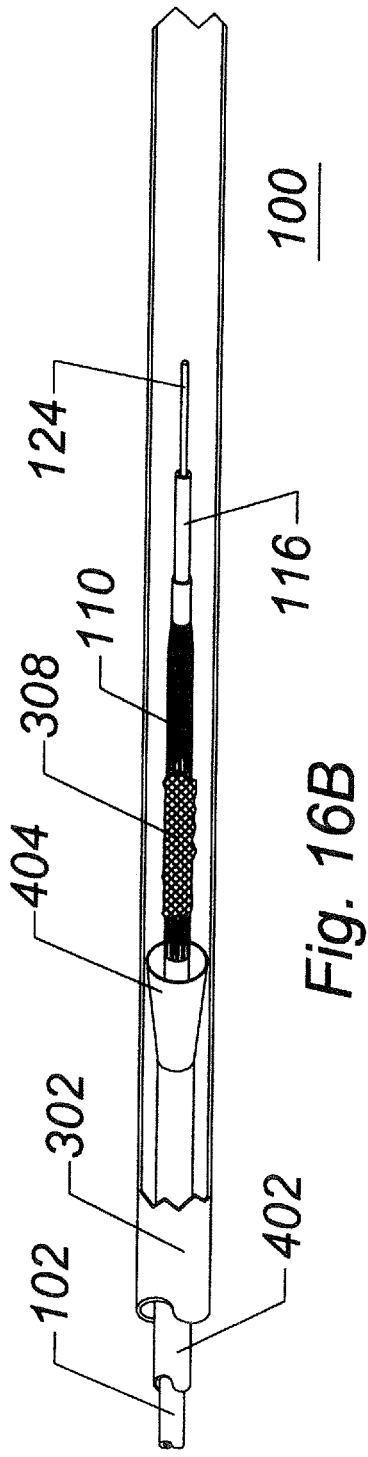

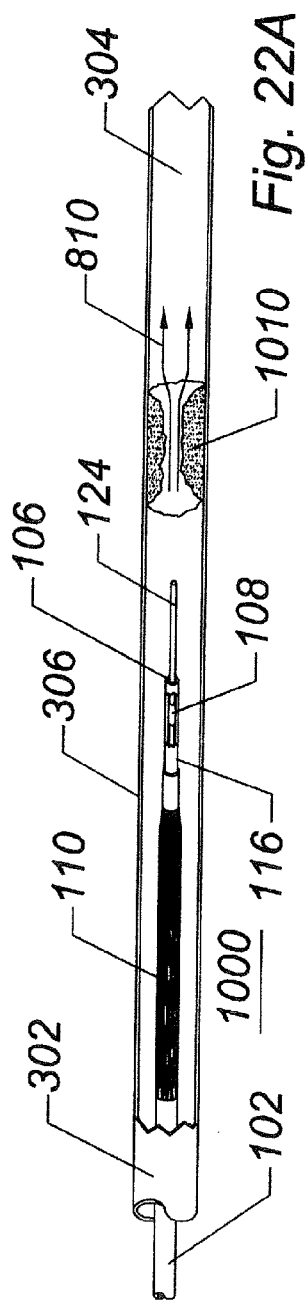
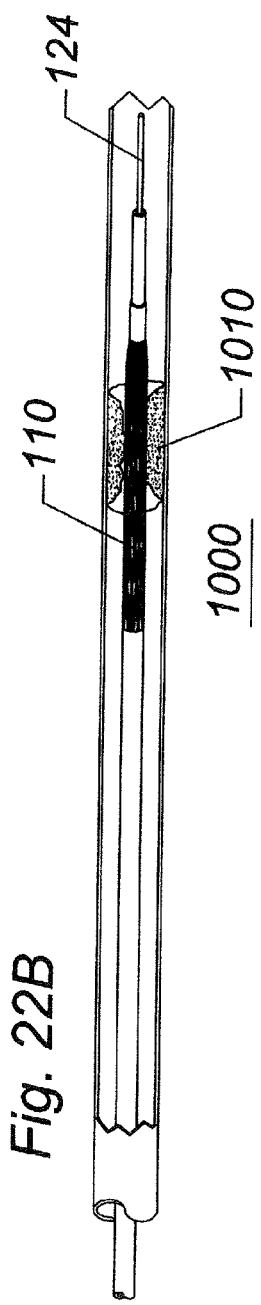
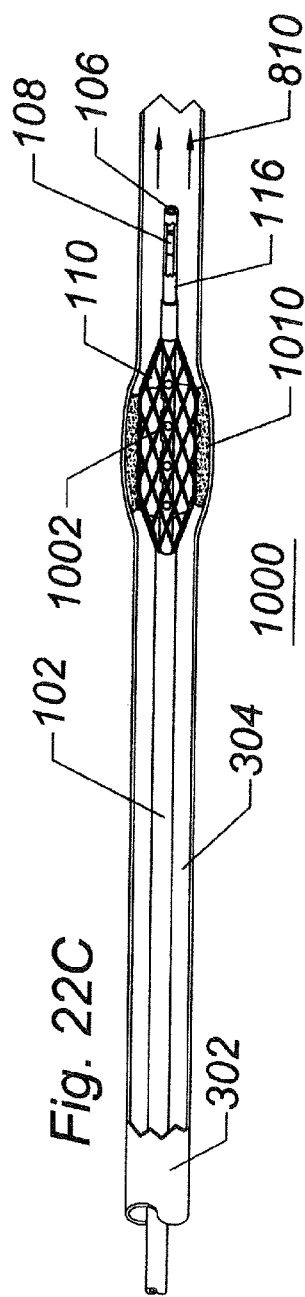

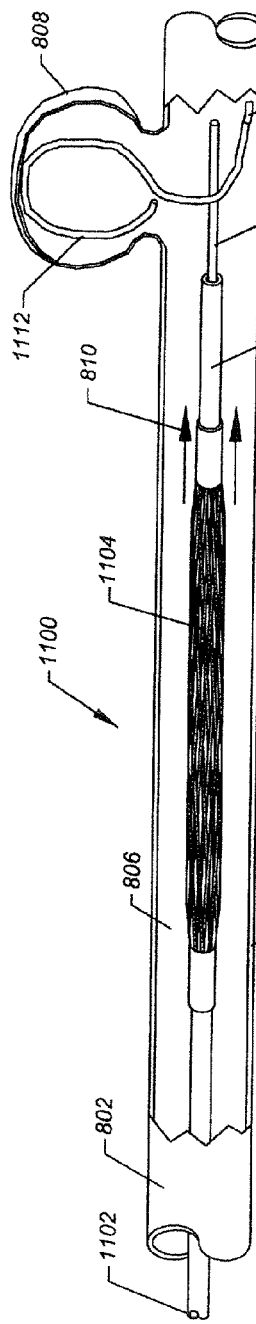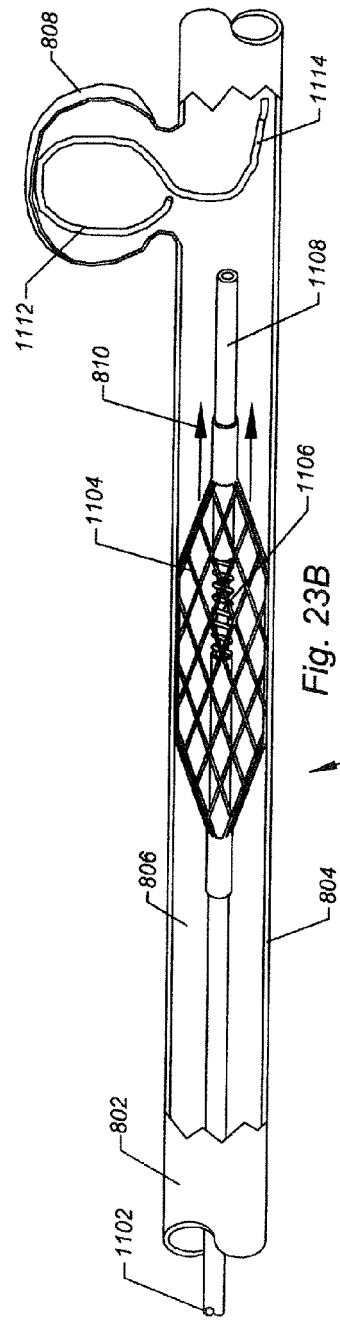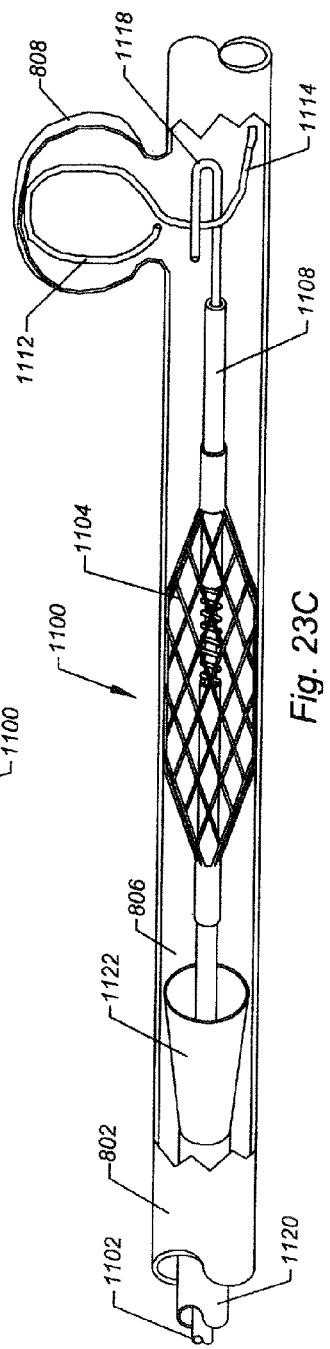

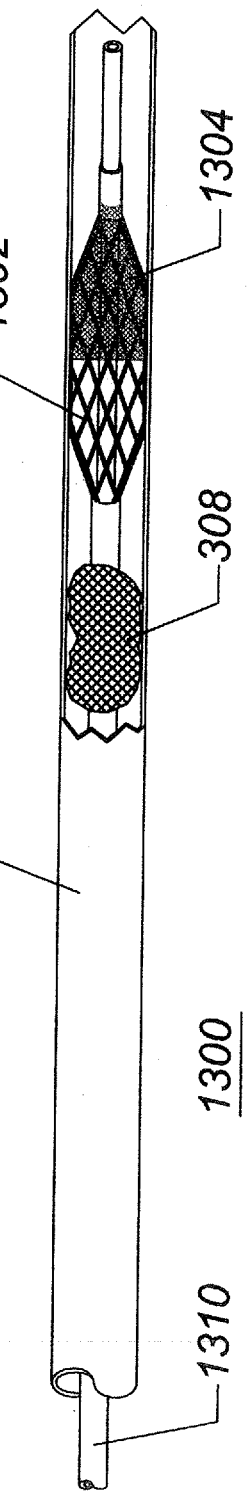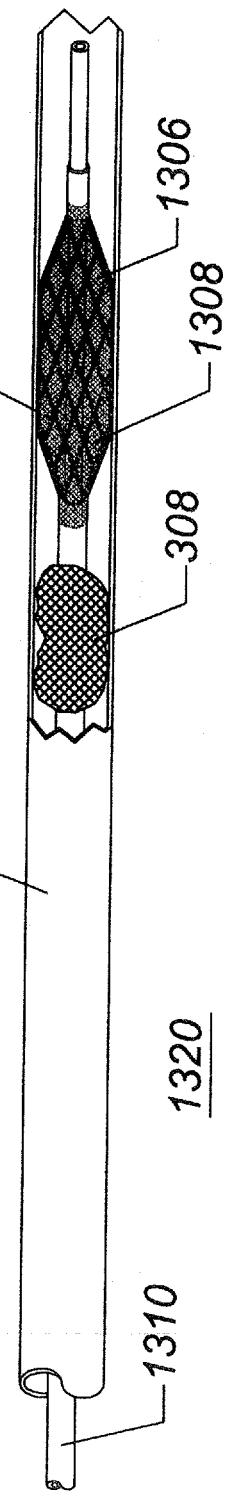

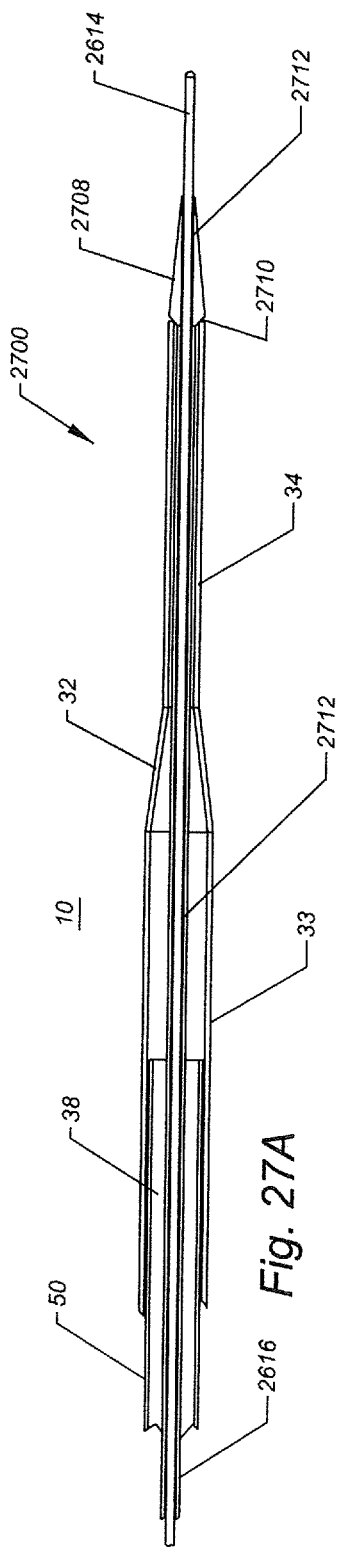
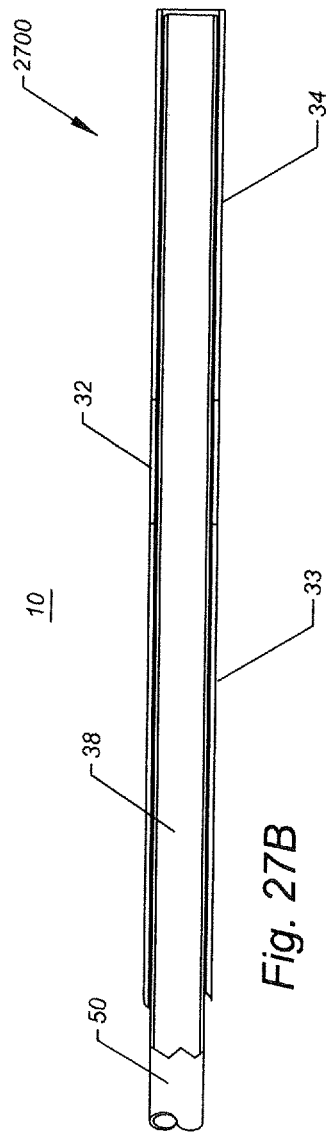
Fig. 27A
Fig. 27B

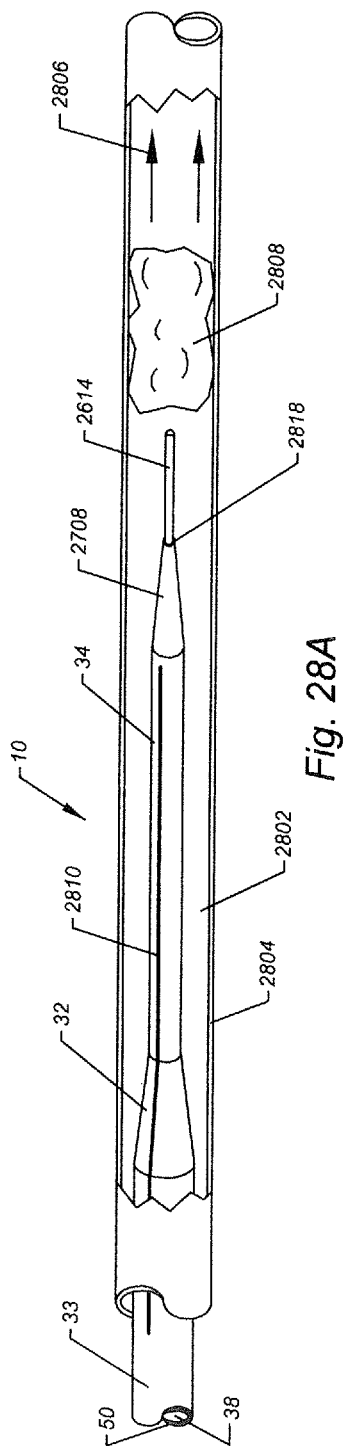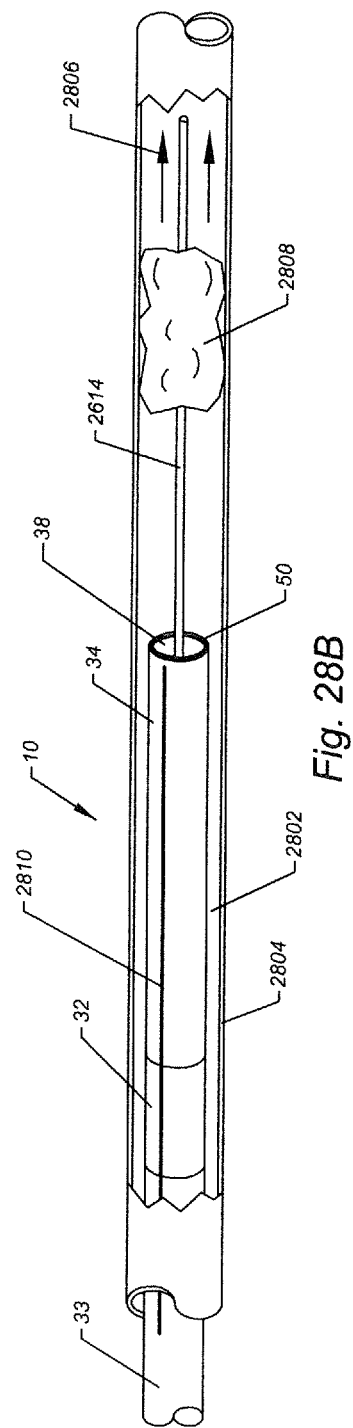

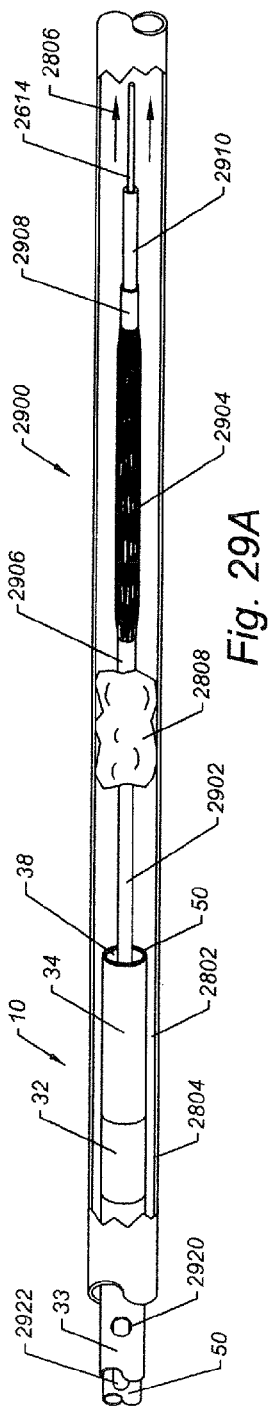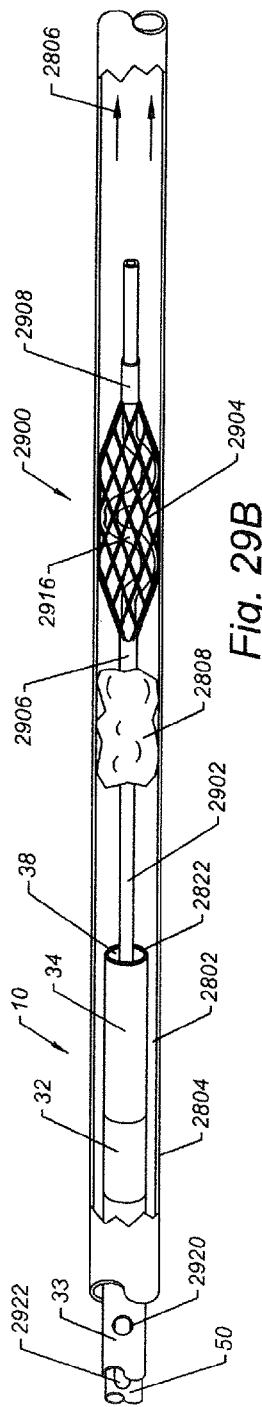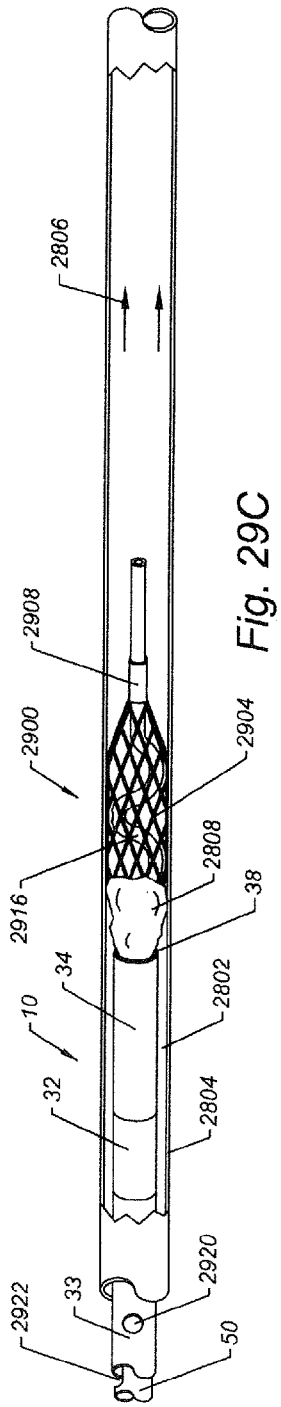

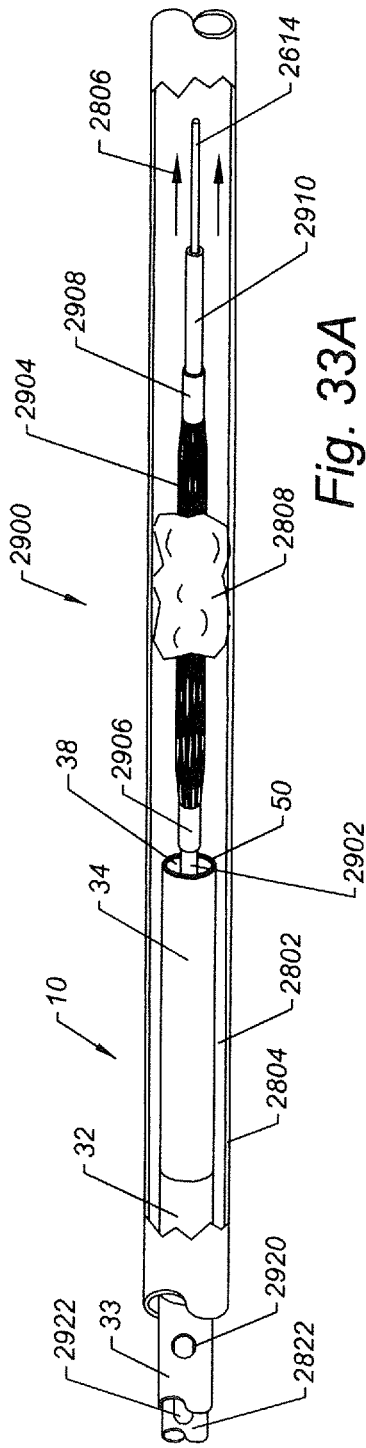
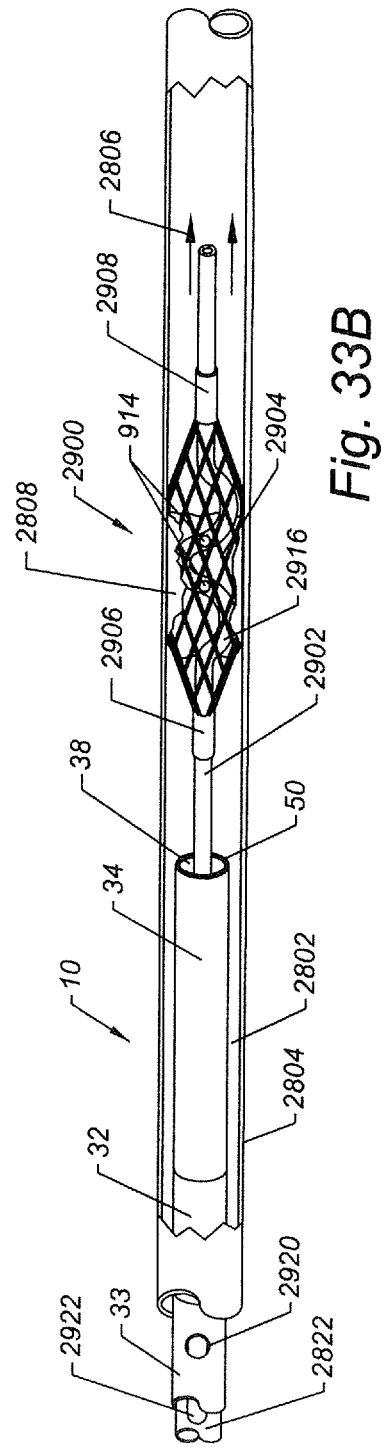
Fig. 33A
Fig. 33B

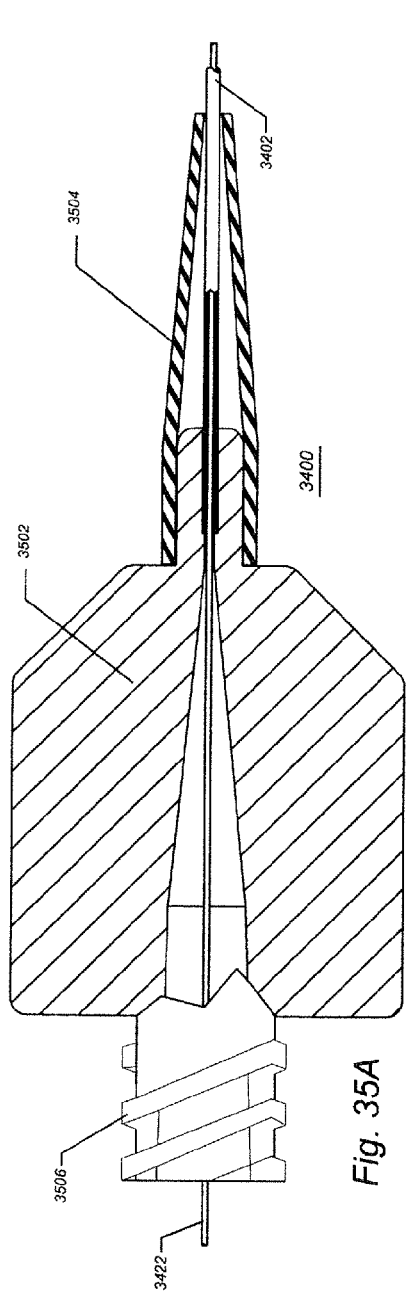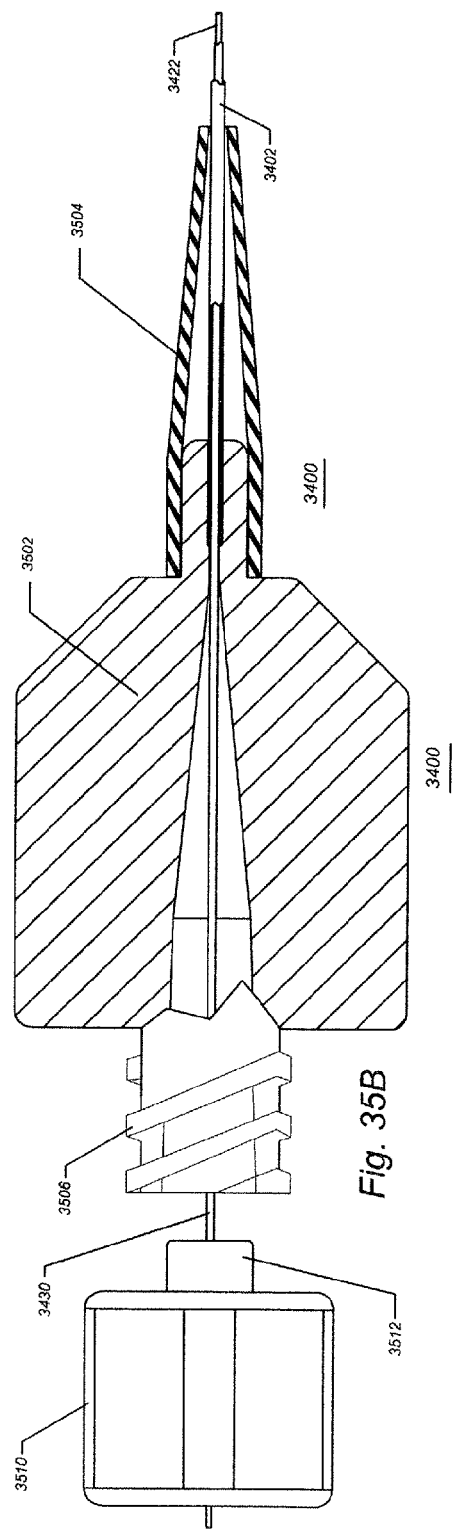

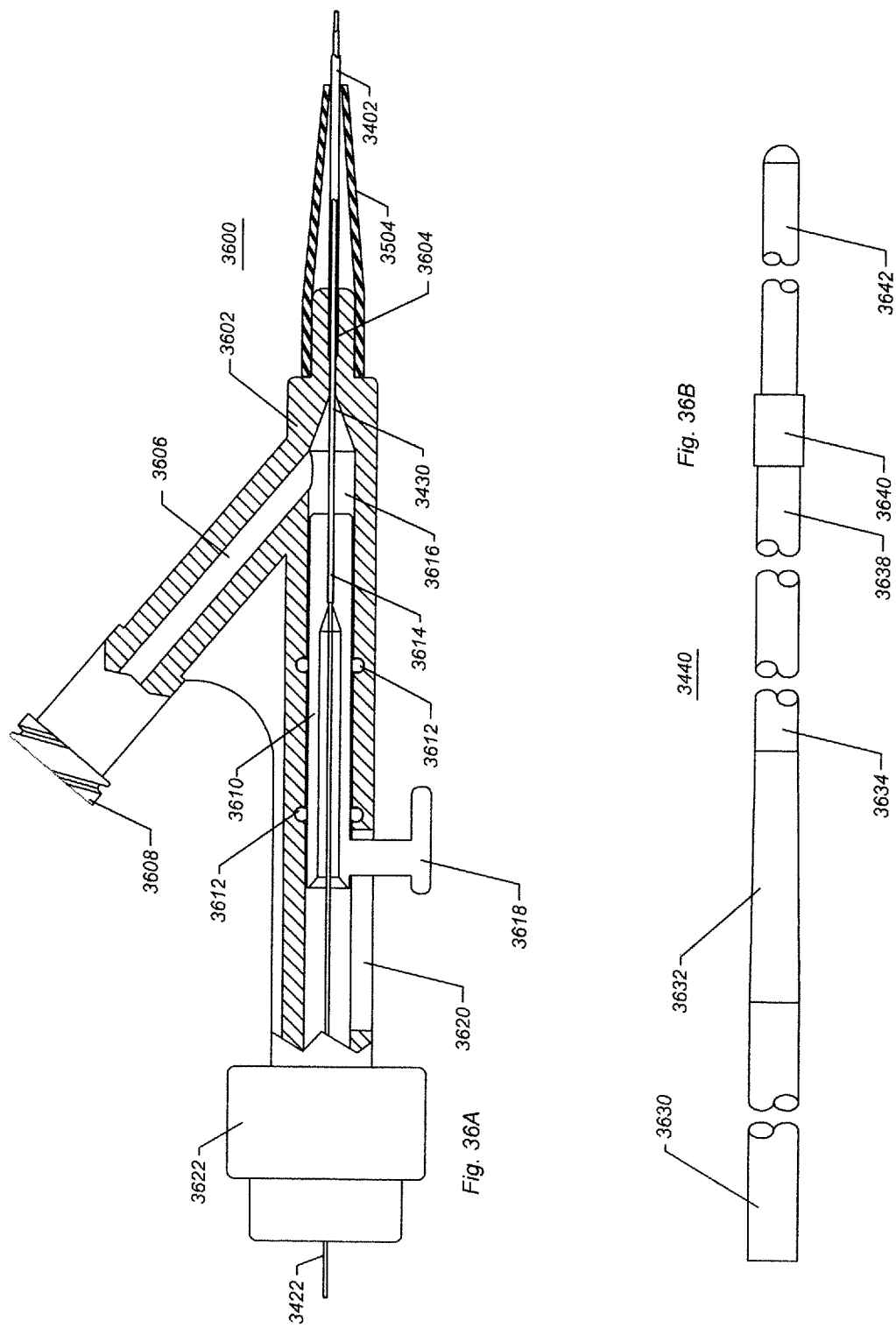

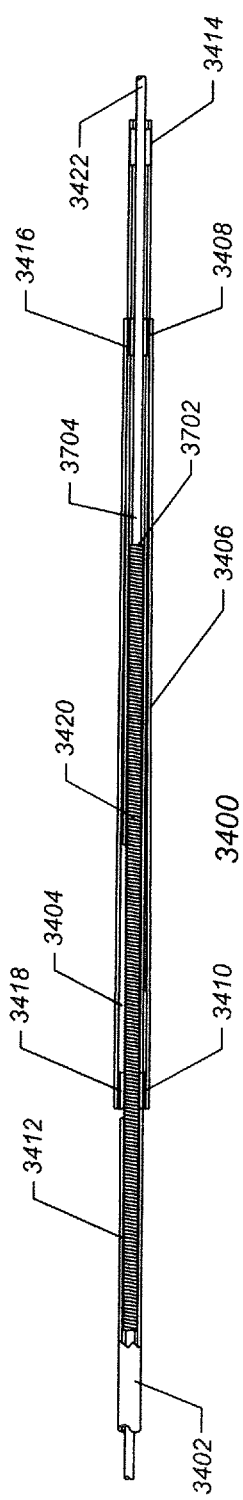
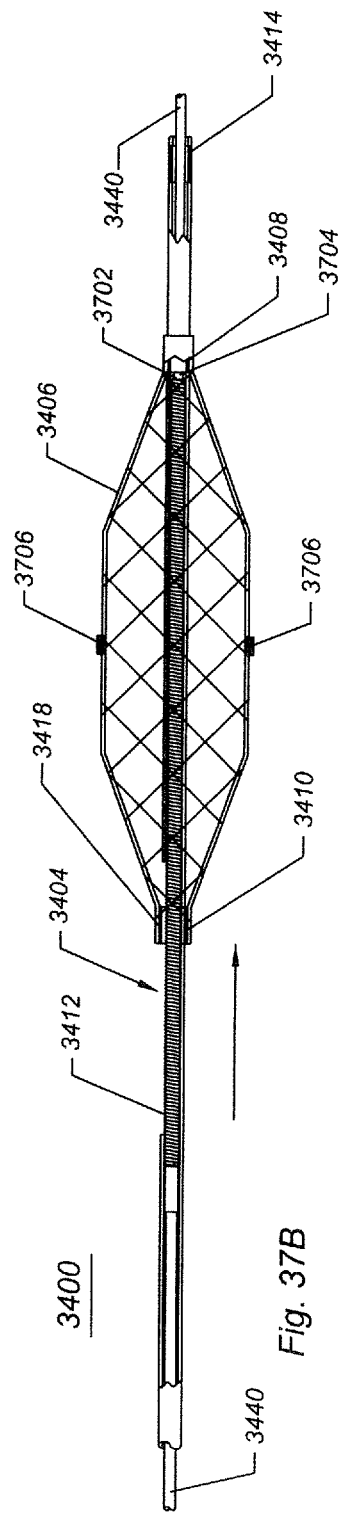

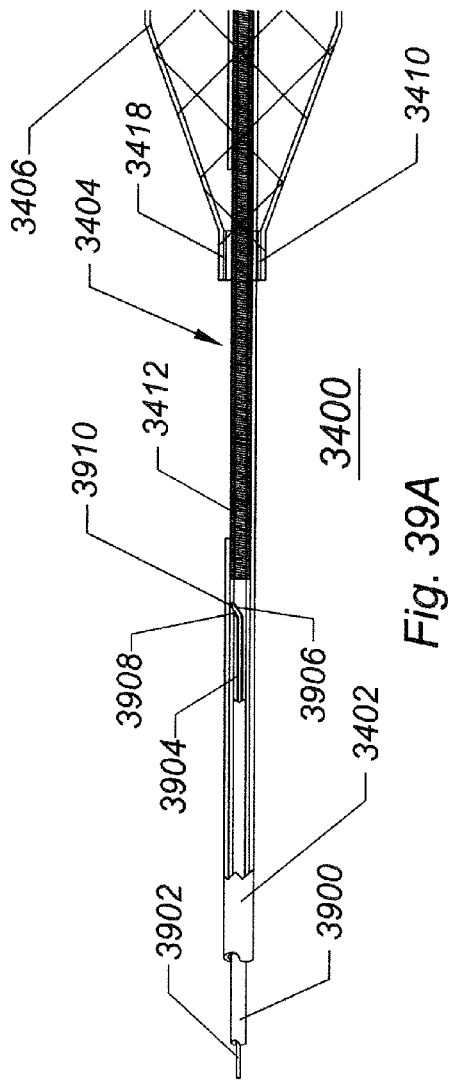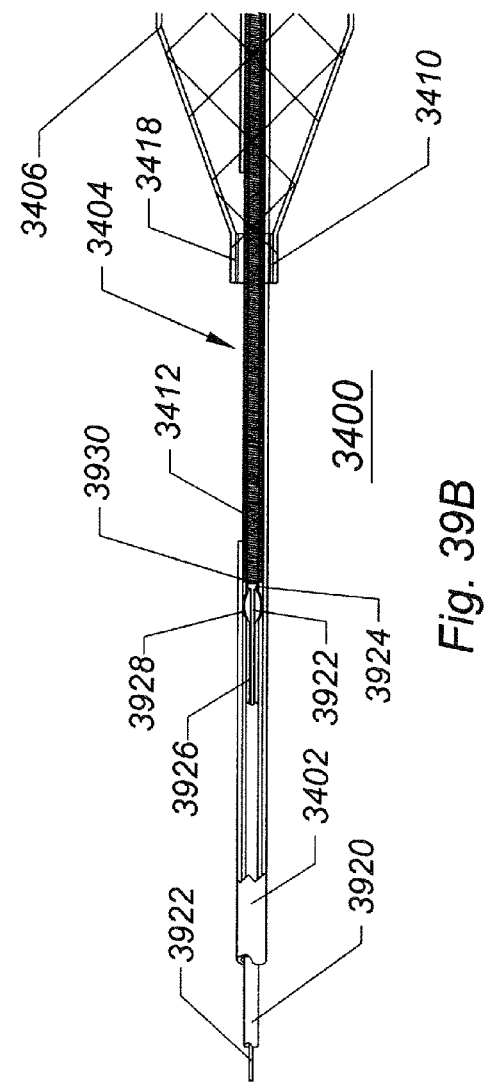
Fig. 39A
Fig. 39B

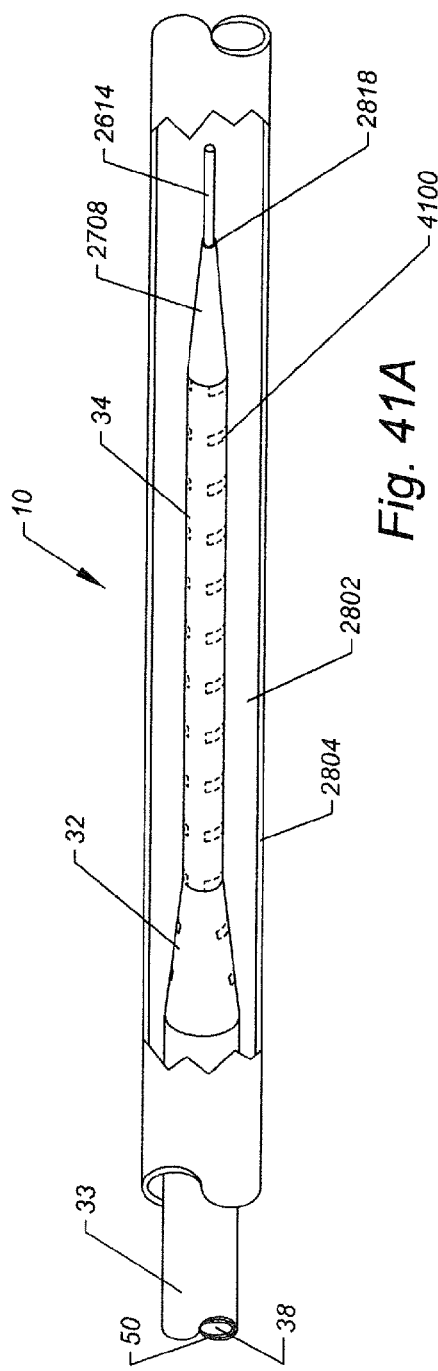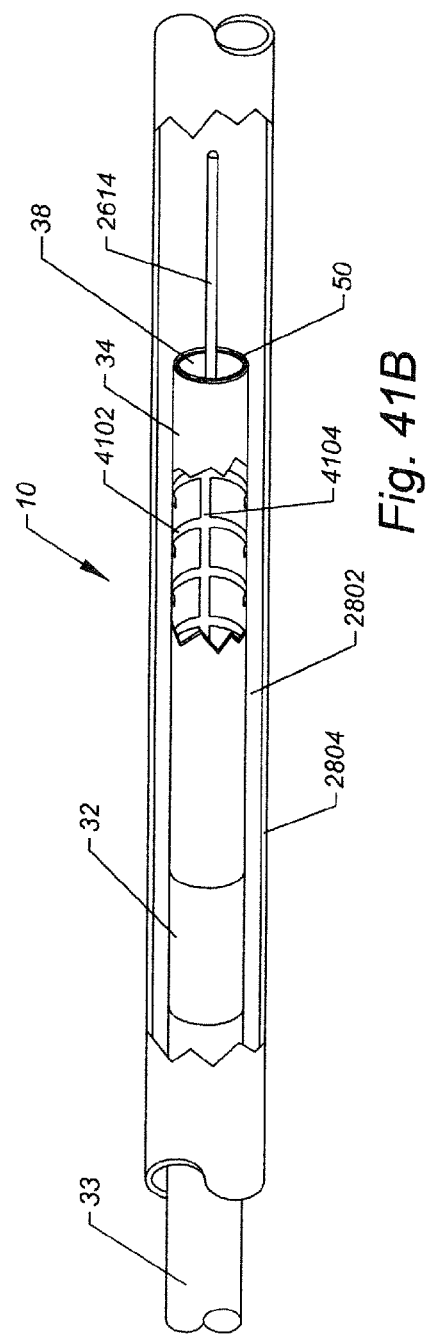
Fig. 41A
Fig. 41B

SYSTEMS AND METHODS FOR REMOVING OBSTRUCTIVE MATTER FROM BODY LUMENS AND TREATING VASCULAR DEFECTS

FIELD OF THE INVENTION

The present invention relates generally to medical devices and methods and more particularly to catheter-based systems and methods useable for removing obstructions from or treating defects in blood vessels, such as blood vessels of the brain.

BACKGROUND OF THE INVENTION

Stroke is a common cause of death in the United States and disabling neurologic disorder. Approximately 700,000 patients suffer from stroke annually. Stroke is a syndrome characterized by the acute onset of a neurological deficit that persists for at least 24 hours, reflecting focal involvement of the central nervous system, and is the result of a disturbance of the cerebral circulation. Its incidence increases with age. Risk factors for stroke include systolic or diastolic hypertension, hypercholesterolemia, cigarette smoking, heavy alcohol consumption, and oral contraceptive use.

Hemorrhagic stroke accounts for 20% of the annual stroke population. Hemorrhagic stroke often occurs due to rupture of an aneurysm or arteriovenous malformation (AVM), causing bleeding into the brain tissue and resultant infarction of brain tissue. The remaining 80% of the stroke population are ischemic strokes and are caused by occluded vessels that deprive the brain of oxygen-carrying blood. Ischemic strokes are often caused by emboli or pieces of thrombotic tissue that have dislodged from other body sites or from the cerebral vessels themselves to occlude in the narrow cerebral arteries more distally. When a patient presents with neurological symptoms and signs, which resolve completely within 1 hour, the term transient ischemic attack (TIA) is used. Etiologically, TIA and ischemic stroke share the same pathophysiologic mechanisms and thus represent a continuum based on persistence of symptoms and extent of ischemic insult.

Emboli occasionally form around the valves of the heart or in the left atrial appendage during periods of irregular heart rhythm and then are dislodged and follow the blood flow into the distal regions of the body. Those emboli can pass to the brain and cause an embolic stroke. As will be discussed below, many such occlusions occur in the middle cerebral artery (MCA), although such is not the only site where emboli come to rest.

When a patient presents with neurological deficit, a diagnostic hypothesis for the cause of stroke can be generated based on the patient's history, a review of stroke risk factors, and a neurologic examination. If an ischemic event is suspected, a clinician can tentatively assess whether the patient has a cardiogenic source of emboli, large artery extracranial or intracranial disease, small artery intraparenchymal disease, or a hematologic or other systemic disorder. A head CT scan is often performed to determine whether the patient has suffered an ischemic or hemorrhagic insult. Blood would be present on the CT scan in subarachnoid hemorrhage, intraparenchymal hematoma, or intraventricular hemorrhage.

Traditionally, emergent management of acute ischemic stroke consisted mainly of general supportive care, e.g. hydration, monitoring neurological status, blood pressure control, and/or anti-platelet or anti-coagulation therapy. In 1996, the Food and Drug Administration approved the use of Genentech Inc.'s thrombolytic drug, tissue plasminogen activator (t-PA) or Activase RTM, for treating acute stroke. A randomized, double-blind trial, the National Institute of Neurological Disorders and t-PA Stroke Study, revealed a statistically significant improvement in stroke scale scores at 24 hours in the group of patients receiving intravenous t-PA within 3 hours of the onset of an ischemic stroke. Since the approval of t-PA, an emergency room physician could, for the first time, offer a stroke patient an effective treatment besides supportive care.

However, treatment with systemic t-PA is associated with increased risk of intracerebral hemorrhage and other hemorrhagic complications. Patients treated with t-PA were more likely to sustain a symptomatic intracerebral hemorrhage during the first 36 hours of treatment. The frequency of symptomatic hemorrhage increases when t-PA is administered beyond 3 hours from the onset of a stroke. Besides the time constraint in using t-PA in acute ischemic stroke, other contraindications include the following: if the patient has had a previous stroke or serious head trauma in the preceding 3 months, if the patient has a systolic blood pressure above 185 mmHg or diastolic blood pressure above 110 mmHg, if the patient requires aggressive treatment to reduce the blood pressure to the specified limits, if the patient is taking anticoagulants or has a propensity to hemorrhage, and/or if the patient has had a recent invasive surgical procedure. Therefore, only a small percentage of selected stroke patients are qualified to receive t-PA.

Obstructive emboli have also been mechanically removed from various sites in the vasculature for years. For example, the "Fogarty catheter" or variations thereof has been used, typically in the periphery, to remove clots from arteries found in legs and in arms. These well known devices are described, for example, in U.S. Pat. No. 3,435,826, to Fogarty and in U.S. Pat. Nos. 4,403,612 and 3,367,101. In general, these patents describe a balloon catheter in which a balloon material is longitudinally stretched when deflated.

In procedures for removing emboli using the Fogarty catheter or other similar catheters, it is typical, first, to locate the clot using fluoroscopy. The embolectomy catheter is then inserted and directed to the clot. The distal tip of the balloon catheter is then carefully moved through the center of the clot. Once the balloon has passed through the distal side of the clot, the balloon is inflated. The balloon catheter is then gradually proximally withdrawn. The balloon, in this way, acts to pull the clot proximally ahead of the balloon to a point where it can be retrieved. The majority of procedures using a Fogarty type catheter repeat these steps until the pertinent vessel is cleared of clot material.

A variety of alternative emboli retrieval catheters have also been developed, in which various wire corkscrews and baskets must be advanced distally through the embolic material in order to achieve capture and removal. However, removal of emboli using such catheters carries attendant potential problems. One such problem occurs when advancing the catheter through the clot dislodges material to a more remote site where removal may become more difficult or impossible.

Although neurointerventional devices and procedures have advanced, there remains a need for expeditious restoration of distal flow to blocked, or stenotic, cerebrovascular vessels, which can lead to severe neurological deficit or patient death.

New devices and methods are thus needed in treating vasculature occlusions in the body, including patients with acute ischemic stroke and occlusive cerebrovascular disease, in treating symptomatic patients with embolization or hemodynamic compromise, or in stroke prevention, e.g., patients with incidental finding of asymptomatic carotid lesion, which improve a patient's neurological function and quality of life without causing significant side effect, and can thus also be used in patients with contraindication to the use of t-PA.

SUMMARY OF THE INVENTIONS

In accordance with one aspect of the present invention, there is provided a system useable for performing a therapeutic or diagnostic task at a location within the body of a human or animal subject, such system comprising a) catheter that has a proximal portion, a distal portion, a lumen and a distal end opening, said catheter being transitionable from a first configuration wherein the distal portion has a first outer diameter that is smaller than the outer diameter of the proximal portion and a second configuration wherein the distal portion is expanded to a second outer diameter that is larger than the first outer diameter and no larger than the outer diameter of the proximal portion and b) a working device that is advanceable though the lumen of the catheter and out of its distal opening at least when the distal portion of the catheter is in is second configuration, said working device being useable to perform the therapeutic or diagnostic task. Examples of the types of working devices that may be used in this system include but are but are not limited to; i) devices for removing thrombus or other obstructive matter from body lumens, ii) flow restoration devices useable to facilitate flow of a fluid though or around an obstruction within a body lumen and iii) devices for deploying or delivering implants (e.g., implantable occlusion coils or implantable embolic devices).

Further in accordance with the invention, there is provided a method for performing a therapeutic or diagnostic task at a location within the body of a human or animal subject, such method comprising the steps of: a) inserting into the subject's body a catheter that has a proximal portion, a distal portion, a lumen and a distal end opening, said catheter being transitionable from a first configuration wherein the distal portion has a first outer diameter that is smaller than the outer diameter of the proximal portion and a second configuration wherein the distal portion is expanded to a second outer diameter that is larger than the first outer diameter and no larger than the outer diameter of the proximal portion; b) positioning the distal end opening in a desired body lumen while the distal portion of the catheter is in its first configuration; c) causing the distal portion of the catheter to transition to its second configuration; d) advancing a working device though the lumen of the catheter and out of its distal opening; and, using the working device to perform the therapeutic or diagnostic task. Examples of the types of working devices that may be used in this method include but are but are not limited to; devices for removing thrombus or other obstructive matter from body lumens, flow restoration devices useable to restore blood flow though an obstructed body lumen and devices for delivering implants (e.g., implantable occlusion coils or embolic devices).

Still further in accordance with the invention there is provided a method for removing obstructive matter from a body lumen, such method comprising the steps of: a) inserting a catheter that has a proximal portion, a distal portion, a lumen and a distal end opening, said catheter being transitionable from a first configuration wherein the distal portion has a first outer diameter that is smaller than the outer diameter of the proximal portion and a second configuration wherein the distal portion is expanded to a second outer diameter that is larger than the first outer diameter and no larger than the outer diameter of the proximal portion; b) positioning the catheter, while in the first configuration, such that its distal end opening is within a body lumen; c) causing the catheter to transition from the first configuration to the second configuration; d) moving obstructive matter through the distal end opening and into the lumen of the catheter; and e) removing the catheter along with the obstructive matter that has been moved into the lumen of the catheter. In some embodiments, negative pressure may be applied through the lumen of the catheter to aspirate obstructive matter through the distal end opening and into the lumen of the catheter. In some embodiments Step D of the method may comprise advancing an obstructive matter moving device (e.g., an embolectomy device) from the catheter and using the obstructive matter moving device to move obstructive matter through the distal end opening and into the lumen of the catheter. One non-limiting example of the types of obstructive matter moving device that may be used is a device having an expandable element that is expanded within the body lumen such that obstructive matter becomes entrained in or engaged by the expandable element in a manner that allows it to thereafter move some or all of the obstructive matter. Such expandable element is then retracted, along with obstructive matter that has become entrained in or engaged by the expandable member, through the distal end opening and into the lumen of the catheter. In some cases the method may further include the step of delivering a therapeutic substance. For example, in cases where the obstructive matter comprises thrombus, a thrombolytic agent or other substance that will dissolving some of the thrombus and/or deter adherence of the thrombus to a wall of the body lumen may be delivered. In some embodiments where an obstructive matter moving device is used, such obstructive matter moving device is used to move the obstructive matter into the catheter, the obstructive matter moving device may initially be used to canalize or compress the obstructive matter in a manner that improves blood flow through or around the obstructive matter for a period of time and, thereafter, is used to move at least some of the obstructive matter through the distal opening and into the lumen of the catheter.

Still further in accordance with the present invention, there is provided a method for increasing flow of a body fluid through an obstructed body lumen, such method comprising the steps of: a) inserting a catheter that has a proximal portion, a distal portion, a lumen and a distal end opening, said catheter being transitionable from a first configuration wherein the distal portion has a first outer diameter that is smaller than the outer diameter of the proximal portion and a second configuration wherein the distal portion is expanded to a second outer diameter that is larger than the first outer diameter and no larger than the outer diameter of the proximal portion; b) positioning the catheter, while in the first configuration, such that its distal end opening is within a body lumen; c) causing the catheter to transition from the first configuration to the second configuration; and d) using the catheter to deliver a treatment that restores or improving flow of a body fluid through an obstructed body lumen. In some embodiments, the treatment delivered may comprise the delivery of a therapeutic substance (e.g., a thrombolytic agent) of a type and in an amount that is effective to improve flow of body fluid through the body lumen. In some embodiments, the treatment delivered may comprise use of a device that canalizes or compresses obstructive matter in a manner that improves flow of body fluid through or around the obstructive matter.

Further aspects, embodiments, variations, details, elements and examples of the present inventions will be understood by those of skill in the relevant art from the accompanying drawings and the following detailed description.

BRIEF DESCRIPTION OF THE DRAWINGS

A general architecture that implements the various features of the invention will now be described with reference to the drawings. The drawings and the associated descriptions are provided to illustrate some but not all embodiments or examples of the invention and do not limit the scope of the claimed inventions in any way. Throughout the drawings, reference numbers are re-used to indicate correspondence between referenced elements.

FIG. 5 is a side elevational cross-sectional view through a distal portion of the catheter of FIG. 1, illustrating an axially movable support coil in a proximal position, according to an embodiment of the invention;

FIG. 6 is a cross-sectional view as in FIG. 5, with the axially movable support coil in a distal position, according to an embodiment of the invention;

FIG. 13A illustrates a side view of a catheter, wherein a guidewire has not yet been inserted into the central catheter lumen, thus the expandable element remains biased in it's fully expanded configuration, according to an embodiment of the invention;

FIG. 13B illustrates a side view of the catheter of FIG. 13A, wherein a guidewire is fully inserted into the catheter lumen resulting in the expandable element being forced into its fully collapsed, minimum diameter configuration, according to an embodiment of the intention;

FIG. 15A illustrates a thrombus removal catheter in its minimum diameter configuration being advanced toward a mass of thrombus within a blood vessel, according to an embodiment of the invention;

FIG. 15B illustrates the thrombus removal catheter of FIG. 15A, wherein the catheter has been advanced through a central portion of the thrombus such that a radially expandable region extends beyond both ends of the thrombus, according to an embodiment of the invention;

FIG. 15C illustrates the thrombus removal catheter of FIG. 15B, wherein the radially expandable region has been diametrically expanded to contact and entrap the thrombus, according to an embodiment of the invention;

FIG. 16A illustrates the thrombus removal catheter of FIG. 15C, wherein the radially expandable region has been re-collapsed, according to an embodiment of the invention;

FIG. 16B illustrates the thrombus removal catheter of FIG. 16A, wherein the catheter, with entrapped thrombus material, is being withdrawn into a funneled guide catheter, according to an embodiment of the invention;

FIG. 22A illustrates a length of vasculature, partially blocked by a hard plaque formation, being approached by a microcatheter and guidewire, according to an embodiment of the invention;

FIG. 22B illustrates the microcatheter of FIG. 22A having been advanced through the central opening of the plaque, according to an embodiment of the invention;

FIG. 22C illustrates the microcatheter of FIG. 22A and FIG. 22B fully dilated within the region of plaque, thus temporarily relieving the restriction caused by the plaque, according to an embodiment of the invention;

FIG. 23A illustrates a length of vasculature having an aneurysm and a partially dislodged embolic coil projecting into the lumen of the parent vessel, wherein a microcatheter is being advanced toward the dislodged coil, according to an embodiment of the invention;

FIG. 23B illustrates an expandable region of the microcatheter in its fully dilated configuration in the proximity of the aneurysm and the partially dislodged coil, according to an embodiment of the invention;

FIG. 23C illustrates a grasper advanced through the central lumen of the microcatheter, wherein the grasper is snaring an end of the dislodged embolic coil, and further wherein an expandable tip guide catheter has been advanced over the microcatheter to receive the snared coil;

FIG. 25A illustrates an expandable member dilated downstream of a thrombus formation through which a microcatheter has been advanced, wherein a membrane partially covers the expandable member, according to an embodiment of the invention;

FIG. 25B illustrates an expandable member dilated downstream of a thrombus formation wherein a membrane substantially seals the gaps in the entire expandable member, according to an embodiment of the invention;

FIG. 27A illustrates a longitudinal cross-section of the distal end of an expandable guide catheter in its radially collapsed configuration, according to an embodiment of the invention;

FIG. 27B illustrates a partial breakaway view of the distal end of the expandable guide catheter of FIG. 27A, wherein the distal end has been radially expanded to a second, larger diameter or cross-section, according to an embodiment of the invention;

FIG. 28A illustrates a radially collapsed, expandable guide catheter being advanced toward a vascular occlusion, according to an embodiment of the invention;

FIG. 28B illustrates the expandable guide catheter of FIG. 28A following radial expansion of the distal end and distal extension of a guidewire, according to an embodiment of the invention;

FIG. 29A illustrates a thrombectomy catheter advanced through the expandable guide catheter and placed with its collapsed, distal end across an occlusive thrombus; according to an embodiment of the invention;

FIG. 29B illustrates the thrombectomy catheter of FIG. 29A with its mesh or snare diametrically expanded at a point past the location of a thrombus;

FIG. 29C illustrates the expanded thrombectomy catheter of FIG. 29B wherein the thrombectomy catheter has been withdrawn proximally to cause the thrombus to be trapped within the expandable guide catheter;

FIG. 33A illustrates a breakaway side view of a vessel having a thrombus disposed therein, wherein a temporary flow restoration catheter has been inserted through the clot, according to an embodiment of the invention;

FIG. 33B illustrates a breakaway side view of the vessel of FIG. 33A wherein the temporary flow restoration catheter has expanded an element within the clot to create a channel through which blood can flow, according to an embodiment of the invention;

FIG. 35A illustrates the proximal end of a thrombectomy or flow restoration catheter comprising a hub, a strain relief, a catheter tube, and a guidewire, according to an embodiment of the invention;

FIG. 35B illustrates the proximal end of a thrombectomy or flow restoration catheter comprising a sleeve for actuating the distal expandable region and a displacement limiting member, according to an embodiment of the invention;

FIG. 36A illustrates the proximal end of a thrombectomy or flow restoration catheter comprising a hub, a hemostasis valve, an injection port for thrombolytic or other pharmacologic agents, and a control member for advancing or retracting an actuation sleeve, according to an embodiment of the invention;

FIG. 36B illustrates an actuation guidewire suitable for distal advance of the proximal end of an expandable mesh, according to an embodiment of the invention;

FIG. 37A illustrates a thrombectomy or flow restoration catheter comprising a radiopaque slider having increased length, according to an embodiment of the invention;

FIG. 37B illustrates the thrombectomy or flow restoration catheter of FIG. 37A wherein the slider has been advanced distally to substantially close the visual, or radiographic, gap between the slider and a forward radiopaque marker, according to an embodiment of the invention;

FIG. 39A illustrates an activation guidewire slidably disposed within a catheter and passing out through the distal end of a mesh, according to an embodiment of the invention;

FIG. 39B illustrates the activation guidewire of FIG. 39A having been radially expanded such that it can exert distal force against a slider coupled to the proximal end of the expandable mesh, according to an embodiment of the invention;

FIG. 41A illustrates the distal end of an expandable guide catheter further comprising a reinforcing backbone and rib structure, wherein the guide catheter is deployed inside a blood vessel with its distal end unexpanded, according to an embodiment of the invention;

FIG. 41B illustrates the expandable guide catheter of FIG. 41A with its distal end expanded inside the blood vessel, according to an embodiment of the invention;

DETAILED DESCRIPTION OF THE PREFERRED EMBODIMENTS

Figure 1:
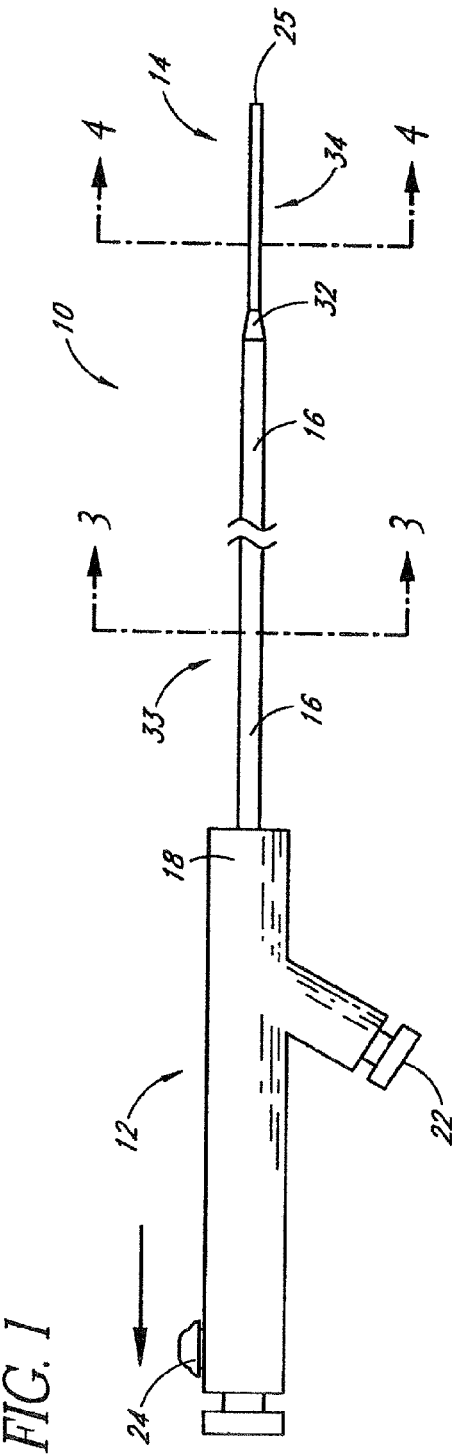
FIG. 1 is a side elevational schematic view of an intracranial aspiration catheter in accordance with the present invention, with a distal segment in a reduced crossing profile configuration, according to an embodiment of the invention.

The inventions disclosed herein may be embodied in other specific forms without departing from its spirit or essential characteristics. The described embodiments are to be considered in all respects only as illustrative and not restrictive. The scope of the inventions is therefore indicated by the appended claims rather than the foregoing description. All changes that come within the meaning and range of equivalency of the claims are to be embraced within their scope.

As used herein, the terms proximal and distal refer to a direction or a position along a longitudinal axis of a catheter or medical instrument. Proximal refers to the end of the catheter or medical instrument closer to the operator, while distal refers to the end of the catheter or medical instrument closer to the patient. For example, a first point is proximal to a second point if it is closer to the operator end of the catheter or medical instrument than the second point. The measurement term French, abbreviated Fr or F, is defined as three times the diameter of a device as measured in mm. Thus, a 3 mm diameter catheter is 9 French in diameter.

There is provided in accordance with one aspect of the present invention, a method for removing, or restoring flow through, thromboembolic material from a carotid or cerebral artery. The method comprises the steps of providing a catheter having a proximal end, a distal end, an expandable distal section having a distal port, an aspiration lumen communicating with the port, and an axially movable support. The distal end of the catheter is inserted into the artery, and the support is distally advanced to expand the distal section. Negative pressure is applied to the aspiration port, to draw the thromboembolic material into the distal section.

The carotid artery may be the common carotid artery, the internal carotid artery or the carotid siphon. Alternatively, the artery may be the middle cerebral artery or the anterior cerebral artery, or elsewhere in the brain.

The method may additionally comprise the steps of introducing oxygenated medium into the artery through the aspiration lumen, or infusing pharmaceutical agent into the artery through the aspiration lumen. The pharmaceutical agent may be a vasodilator such as nifedipine or nitroprusside. The pharmaceutical agent may alternatively comprise t-PA. The thromboembolic material may be located using intravascular ultrasound, or carotid Doppler imaging techniques.

In accordance with another aspect of the present invention, there is provided an intracranial aspiration catheter. The catheter comprises an elongate flexible tubular body, having a proximal end, a distal end, and an aspiration lumen extending therethrough. The aspiration lumen in a distal section of the body is movable between a first, reduced inside diameter for transluminal navigation and a second, enlarged inside diameter for aspirating material. A support is provided, for controllably supporting the aspiration lumen against collapse when in the second diameter. A control is provided on the proximal end of the catheter for controlling the support. In one implementation, the support comprises a spiral element such as a spring coil. The support may be axially movable, such as between a proximal position when the distal section is in the low cross sectional configuration, and a distal position in which the distal section is enlarged, and supported against collapse under aspiration. Alternatively, the support is activated by rotating a first end of the support relative to a second end of the support.

The aspiration lumen may be defined within a tubular wall having a plurality of folds therein, when the aspiration lumen is in the first inside diameter configuration. Alternatively, the aspiration lumen may be defined within a wall made from a stretchable material.

In accordance with another aspect of the present invention, there is provided a method of establishing a flow path through a catheter, positioned across a non-linear segment of vasculature. The method comprises the steps of transluminally navigating an enlargeable tubular wall through a non-linear segment of vasculature, and manipulating a support within a tubular wall to enlarge the inside diameter of the tubular wall to create a flow path across the non-linear segment. The manipulating step may comprise distally advancing a tubular support structure within the tubular wall. In one implementation, the method comprises distally advancing a coil within the tubular wall.

In accordance with a further aspect of the present invention, there is provided a method of aspirating material. The method comprises the steps of transluminally advancing a catheter to the site of an obstruction, the catheter having an aspiration lumen therein. A support is moved within the aspiration lumen, and, thereafter, material is aspirated from the obstruction through the aspiration lumen.

In accordance with another aspect of the present invention, there is provided an intracranial aspiration catheter. The catheter comprises an elongate flexible tubular body, having a proximal end, a distal end, and an aspiration lumen extending therethrough. The distal section on the body is movable between a first, reduced inside diameter for transluminal navigation, and a second, enlarged inside diameter for aspirating material. A support is axially movable between a proximal position when the aspiration lumen is in the first diameter, and a distal position for supporting the aspiration lumen against collapse when in the second diameter.

In one implementation, the support comprises a coil. The distal section may have a length of no greater than about 20 cm, in certain embodiments a length of no greater than about 10 cm, and often within the range of from about 5 cm to about 15 cm.

In other embodiments, a microcatheter is disclosed, having an outside diameter of approximately 3-French or smaller, with the incorporation of an outer, diametrically expansile/contractile element or snare near the distal region of the device. This expansile/contractile element coupled with the micro-catheter system can serve a variety of therapeutic indications within t h e cerebrovasculature. Herein, the system may be defined as a multi-utilitarian microcatheter. Included amongst these indications are flow restoration within occluded vasculature or ducts, thrombus retrieval, thrombolysis, and temporary neck bridging/neck remodeling of aneurysms. In some embodiments, the microcatheter can comprise a distention means for vascular anastomotic regions, flow restoration within an occluded vessel, foreign body retrieval, or an endovascular filter.

In an embodiment, the micro-catheter can comprise means to deliver therapeutic devices and diagnostic agents through one or more of the catheter's lumens or side holes, which further adds to this systems utility. The devices' lumen, or lumens, could allow for aspiration or drainage.

The Multi-Utilitarian Micro-Catheter System can be provided as an axially elongate tubular structure with distal and proximal ends and a lumen throughout its length. The length of the catheter can be approximately 150 cm and can range between 100 cm and 200 cm. The catheter can have an outer diameter with the element contracted of no more than 1 mm (3 F). The micro-catheter advantageously comprises lateral flexibility which can be constant or can comprise a plurality of increasingly flexible regions moving from the proximal to the distal end of the micro-catheter. The micro-catheter advantageously comprises the property of substantial column strength to facilitate pushability through the vasculature.

The outer diametrically expansile/contractile element, hereafter referred to as the expandable element, which can be generally affixed to the catheter shaft near the distal end of the micro-catheter shaft, can be fabricated from a variety of metallic or polymeric materials, either porous, non-porous, or a combination of these materials. This expandable element can be located proximate the distal region of the micro-catheter. In other embodiments, the expandable element or snare can be located about 3-5 cm from the distal tip to improve guidewire aided navigation through tortuous vasculature. The design is provided with the expandable element having a maximum, expanded outer diameter of 2 mm to 10 mm, but preferably between 2 mm to 7 mm. The expandable element outer diameter can range between 0.2 mm to 10 mm larger in diameter than the outer diameter of the micro-catheter shaft.

To contract the expandable element diametrically, a standard 0.010", 0.013" diameter guidewire, or other appropriate size, is introduced with the catheter's lumen and one or more lumen constrictions are provided just distal to the expandable element, with an optional constriction positioned proximal to the expandable element. Once the guidewire is positioned through these constrictions, it provides enough frictionally induced axial force on the distal constriction to cause the expandable element to contract in diameter (and expand the element linearly). The guidewire can also increase the bending stiffness of the catheter system. The proximal constriction is useful in maintaining guidewire position and can be advantageous if the guidewire is not otherwise secured at the proximal end of the catheter system. The distal lumen within the element can be provided with a length of helically disposed tubing, a length of serpentine tubing, a biased coil having a central lumen through which a secondary catheter can be inserted, a telescoping tube set, or a bellows mechanism, which provides a corresponding length alteration of the catheter's lumen to coincide with that of the expandable element. The length of the expandable element can be between 10 mm and 50 mm in the outer diametrically expansile configuration and between 12 mm and 100 mm in length in its contractile, minimum diameter configuration.

In other embodiments, the guidewire can straighten a pre-curved catheter shaft disposed between the two ends of an expandable snare or element. Straightening of the pre-curved catheter shaft can result in the two ends of the expandable element being moved axially apart causing the expandable snare or element to diametrically collapse to a first, diametrically unexpanded configuration. Removing the guidewire can cause the pre-curved catheter shaft to restore to its original curved or serpentine shape, decreasing the distance between the two ends of an expandable snare or mesh, and causing the snare or mesh to increase in diameter to a second, diametrically expanded configuration.

Another aspect or embodiment of the invention comprises a radially, or diametrically, expandable or contractible flow restoration, foreign body retrieval, or thrombus retrieval element that is expanded by coercing the proximal end of the element to advance distally, relative to a stationary distal end of the element. Distal advance of the proximal portion of the element is slidably constrained about the outer diameter of the catheter shaft. A guidewire, sleeve, step guidewire, linkage, pusher, or other element can be inserted from the proximal end of the catheter, through a central lumen of the catheter and force an internal traveler, slider, or gate to advance distally. The traveler can be affixed to an external collar through a window or skive in the catheter shaft, causing the external collar, to which the proximal end of the element is affixed, to move distally, resulting in diametric, lateral, or radial, expansion of the element.

Other aspects or embodiments of the inventions include the methods of use. In a first embodiment, the device can be used for the purposes of thrombus engagement, thrombus manipulation, and flow restoration within a partially or totally occluded vessel. In this embodiment, the device is first prepared by flushing, or priming, the lumen with saline. A 0.010" OD guidewire is then placed within the lumen to contract, inwards or downwards, the outer diameter of the expandable element. The system (catheter and guidewire) are then navigated together to the site of the occlusive thrombus. The catheter and guidewire are advanced through the thrombus so that the expandable element is positioned within the thrombus. Once positioned through the thrombus, the guidewire is then removed (or partially pulled back away for the lumen constrictions). This allows for the element to expand within the thrombus accomplishing two purposes; 1) to entwine the thrombus, pushing it outwardly against the vessel wall, and 2) to allow blood flow restoration to occur to ischemic areas distal of the thrombus, either acutely or extended periods of time. Additionally, diagnostic agents (such as radiographic, MRI, or other contrast agents) can be administered through the catheter lumen to assess the vasculature distal to the occlusive thrombus.

In another embodiment of the methods of use, the catheter can be used to perform targeted thrombolysis. In this embodiment, the device is first prepared by flushing or priming the lumen with saline. A 0.010" OD, or other size, guidewire can then be inserted within the lumen to contract, inwards or downwards, the outer diameter of the element. The system (catheter and guidewire) are then navigated together to the site of the occlusive thrombus. The catheter and guidewire are advanced through the thrombus so that the expandable element is positioned within the thrombus. Once the element is expanded, the thrombus is immobilized. Thrombolytic agents, or other therapeutic agents, can be administered directly into the thrombus through side holes located in the wall of the catheter in the region of the expandable element. The side holes operably communicate between the lumen of the catheter and the environment outside the catheter.

In another embodiment of the methods of use, the catheter can be used to perform thrombus retrieval. In this embodiment, the device is first prepared by flushing or priming the lumen with saline. A 0.010" OD guidewire is then inserted within the lumen to contract, inwards or downwards, the outer diameter of the element. The system is then navigated together to the site of the occlusive thrombus. The catheter and guidewire are advanced through the thrombus so that the expandable element is positioned within the thrombus. The expandable element is expanded, engaging the thrombus. After engaging the thrombus with the expanded element, the user can either administer thrombolytic agents, contract the element by moving forward the guidewire through the constrictions, or both, to further entwine the thrombus. The catheter with entrapped thrombus is then removed from the vasculature. Additionally, the user may elect to keep the element expanded, and remove the catheter device from the vasculature. Lastly, the thrombus removal could be aided by aspiration through the catheter side holes.

In another embodiment of the methods of use, the catheter can be used to perform temporary neck remodeling of aneurysms or other vascular lesions. Often during coil embolization of aneurysms, the aneurismal necks encountered are considered wide, necessitating the need for a neck-bridging device such as a temporary micro-balloon or an implantable stent. These neck-bridging devices hold the coils in place to prevent them from dropping into the parent vessel during delivery. Balloons conform to the inner surface of the vessel wall and provide a smooth surface against the coils, but seal the vessel from blood flow for perhaps long durations, such sealing having potentially catastrophic ischemic consequences if sustained for too long a time. After filling the aneurysm with coils these micro-balloons are deflated and removed for the vasculature. Neurological stents are permanent implants that can bridge the neck during the coiling procedure, they are expensive and non-retrievable, but allow blood flow through them. The design/method concept disclosed herein would be to employ the microcatheter with the expandable element positioned across the neck oft he aneurysm and radially expand the element to provide the neck bridge. The element in this case could be provided with a non-porous surface about the cylindrical outer surface portion enabling a smoother, non-open surface against the delivered embolization coils. Other embodiments can comprise a window, a skive, a hole, or a breach in the medial or distal portion of the catheter to allow the introduction of a coil deliver micro-catheter (coaxially) into the aneurysm. In this embodiment, the catheter system may be slightly larger (3-Fr to 5-Fr) than the up to 3-Fr diameter typical microcatheter.

In other embodiments, the microcatheter can be used for the purposes of anastomosis distension or dilation, vascular foreign body retrieval, temporary dilatation and flow restoration through atheromatous plaque, and vascular embolic filtering. These goals can be addressed by inserting the proper therapeutic device, such as a dilatation balloon, grasper or basket device, high force mesh dilator, or distal protection filter, respectively, through the working lumen of the microcatheter.

In certain embodiments, the expandable aspiration catheter can serve as an expandable guide catheter for placement of the micro-catheter. The expandable guide catheter is advanced to a target region in cooperation with a guidewire to allow for steering and manipulation through the vasculature. In an exemplary procedure, the guidewire and expandable guide catheter are introduced into the vasculature at a site within a femoral or iliac artery. Using a Seldinger technique, or other percutaneous procedure, a hollow 18-Gauge needle can be introduced into a femoral artery via percutaneous procedure. A guidewire is next advanced through the hollow needle and into the arterial tree. The hollow needle is next removed and a catheter introducer is advanced into the arterial tree. The expandable guide catheter is next advanced through the catheter introducer either through the same guidewire or through a larger guidewire suitable for aortic traverse. The expandable guide catheter, in its radially collapsed configuration, is advanced through the aortic arch, into a carotid artery, through the carotid siphon and into a region proximate the circle of Willis. The distal end of the expandable guide catheter is next expanded by advancing an internal element distally to force the distal end radially outward and maintain an enlarged diameter inner lumen. The expandable guide catheter can provide a very small diameter, flexible catheter that is easily inserted through tortuous anatomy such as the carotid siphon or the vertebral and basilar arteries. Once properly placed, the expandable guide catheter can be diametrically expanded to generate a lumen larger than would be possible with a standard, non-expandable catheter. In addition, the expanded guide catheter can partially or completely straighten out the tortuous vasculature to allow passage of larger diameter, less flexible microcatheters suitable for advanced therapeutic or diagnostic purposes. The expanded guide catheter can serve as an aspiration device and as a shield for retrieval of debris, thrombus, or other material from the vasculature.

For purposes of summarizing the invention, certain aspects, advantages and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein. These and other objects and advantages of the present invention will be more apparent from the following description taken in conjunction with the accompanying drawings.

Referring to FIG. 1, there is disclosed a catheter 10 in accordance with one aspect of the present invention. Although primarily described in the context of a an expandable distal segment aspiration catheter with a single central lumen, catheters of the present invention can readily be modified to incorporate additional structures, such as permanent or removable column strength enhancing mandrels, two or more lumen such as to permit drug or irrigant infusion or radiation delivery or to supply inflation media to an inflatable balloon, or combinations of these features, as will be readily apparent to one of skill in the art in view of the disclosure herein. In addition, the present invention will be described primarily in the context of removing obstructive material from remote vasculature in the brain.

The catheters disclosed herein may readily be adapted for use throughout the body wherever it may be desirable to introduce a low profile catheter and then provided a relatively large diameter aspiration or supported working channel. For example, low diameter catheter shafts in accordance with the present invention may be dimensioned for use throughout the coronary and peripheral vasculature, the gastrointestinal tract, the urethra, ureters, Fallopian tubes and other lumens and potential lumens, as well. The expandable lumen structure of the present invention may also be used as a minimally invasive percutaneous tissue tract expander, such as for diagnostic or therapeutic access to a solid tissue target (e.g., breast biopsy or tissue excision).

The catheter 10 generally comprises an elongate tubular body 16 extending between a proximal end 12 and a distal functional end 14. The length of the tubular body 16 depends upon the desired application. For example, lengths in the area of from about 120 cm to about 140 cm or more are typical for use in femoral access percutaneous transluminal coronary applications. Intracranial or other applications may call for a different catheter shaft length depending upon the vascular access site, as will be understood in the art.

In the illustrated embodiment, the tubular body 16 is divided into at least a fixed diameter proximal section 33 and an adjustable diameter distal section 34 separated by a transition 32, discussed infra. Alternatively, the adjustable diameter feature of distal section 34 can extend the entire length of the catheter from the manifold 18 or other proximal connector to distal tip 25, as will become apparent from the disclosure herein.

The proximal end 12 of catheter 10 is additionally provided with a manifold 18 having one or more access ports as is known in the art. Generally, manifold 18 is provided with a guidewire port 20 in an over-the-wire construction, and an aspiration port 22. Alternatively, the aspiration port 22 may be omitted if the procedure involves removal of the guidewire proximally from the guidewire port 20 following placement of the aspiration catheter, and aspiration through the guidewire port. Additional access ports may be provided as needed, depending upon the functional capabilities of the catheter. Manifold 18 may be injection molded from any of a variety of medical grade plastics, or formed in accordance with other techniques known in the art.

Figure 2:
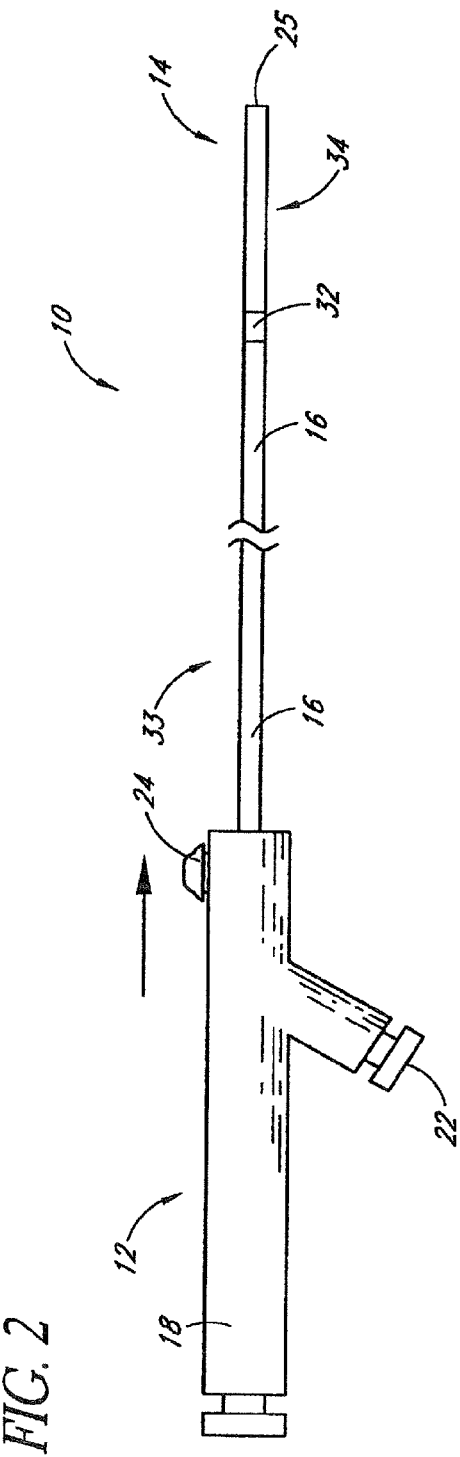
FIG. 2 is a side elevational view as in FIG. 1, with the distal segment in an enlarged cross-sectional configuration, according to an embodiment of the invention.

Manifold 18 is additionally provided with a control 24, for controlling the radial expansion of the distal segment 34 of the catheter. Control 24 may take any of a variety of forms depending upon the mechanical structure of the support. In the illustrated embodiment, control 24 comprises a slider switch, which is mechanically axially moveably linked to the distal support (discussed below) such that proximal retraction of the slider switch 24 produces a proximal movement of the support. This allows the unsupported distal section 34 to assume its low profile configuration as illustrated in FIG. 1. Distal axial advancement of the slider switch 24 produces a distal axial advance of the support, as illustrated in FIG. 2. In the distal position, the support advances the distal segment 34 from the reduced diameter as illustrated in FIG. 1, to the enlarged diameter as illustrated in FIG. 2. In the enlarged configuration, the support maintains patency of a central lumen extending through the distal segment 34 to accommodate aspiration as will be discussed below.

Any of a variety of controls may be utilized, including switches, levers, rotatable knobs, pull/push wires, and others, which will be apparent to those of skill in the art in view of the disclosure herein.

Figure 3B:
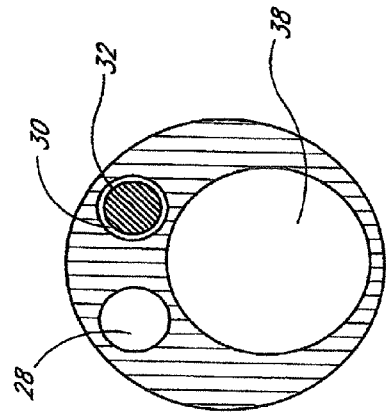
FIG. 3B is an alternate cross-section through an intracranial aspiration catheter having an over-the-wire configuration, according to an embodiment of the invention.
Figure 3A:
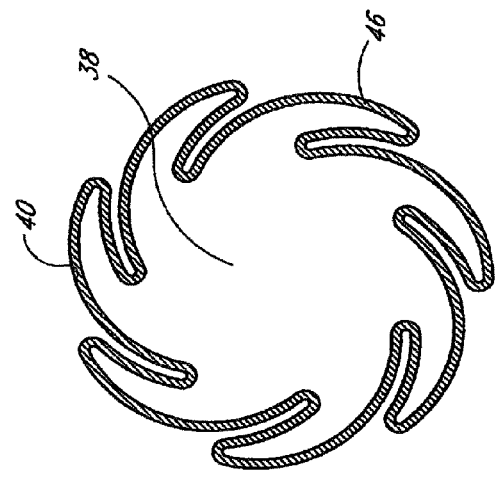
FIG. 3A is a cross-sectional view taken along the line 3-3 in FIG. 1, according to an embodiment of the invention.

Referring to FIG. 3A, there is illustrated a cross-sectional view through the proximal section 33 of the catheter shaft 16 of the embodiment of FIG. 1. In the illustrated embodiment, the proximal section 33 comprises a two lumen extrusion, having a control wire lumen 30 with an axially movable control wire 32 therein, and an aspiration lumen 38. Aspiration lumen 38 also can serve as the guidewire lumen. Alternatively, the proximal section 33 can be formed having a concentric configuration if desired.

In an alternate configuration, as illustrated in FIG. 3B, a three lumen extrusion is utilized in the proximal section 33. A separate guidewire lumen 28 is provided, for allowing an over-the-wire configuration in which the guidewire does not need to be removed in order to accomplish aspiration. The guidewire lumen 28 therefore extends between a proximal access port 20 on the manifold 18, and a distal internal access port (not illustrated) at which point the guidewire lumen 28 opens distally into the aspiration lumen 38. Generally, the distal access port will be spaced substantially distally from the manifold along the length of the catheter. The distal access port may be positioned anywhere within the range of from about 10 cm to about 60 cm from the distal end of the catheter. This enables a partial proximal withdrawal of the guidewire following placement of the catheter, to allow use of the aspiration lumen 38 as will be apparent to those of skill in the art. However, the guidewire may remain within the guidewire lumen 28, such that it can be readily distally advanced into the distal vasculature, such as for repositioning or replacement of the catheter 10.

The distal section 34 comprises a thin flexible wall defining a central lumen 38 extending axially therethrough. The flexible wall is capable of moving between a reduced crossing profile configuration, such as that illustrated in FIG. 1, and an enlarged crossing profile configuration such as that illustrated in FIG. 2. The reduced crossing profile configuration of FIG. 1 is provided for transluminal navigation of distal torturous vasculature to reach a target site. Once the target site has been reached, the distal segment 34 is radially enlarged and supported to provide an enlarged working channel such as an aspiration lumen as will be discussed below.

Movement of the distal section 34 from the reduced diameter to the enlarged diameter may be accomplished in a variety of ways, depending upon the desired construction. Referring to FIG. 4A, for example, a thin walled tubular segment is provided having an enlarged diameter, such as equivalent to the enlarged diameter of FIG. 2. The tubular segment is folded such as by partially collapsing a first wing 42 and a second wing 44, leaving a reduced diameter central lumen 38 having a sufficient inside diameter to axially advance over a guidewire. The first and second wings 42 and 44 are thereafter wrapped around a central portion 46 of the distal section 34 as illustrated in FIG. 4A. The resulting folded configuration may be retained by applying a heat set, as is known in the balloon angioplasty arts. The distal section 34 may be attached in the vicinity of transition 32 using well known catheter fabrication techniques.

In general, the collapsed diameter of lumen 38 will be approximately 0.003 inches or greater larger than the outside diameter of the intended guidewire. Guidewires having diameters in the range of from about 0.009 inches to about 0.016 inches are presently contemplated.

Avoiding a tight fit between the guidewire 40 and the inside diameter of the guidewire lumen 28 enhances the slideability of the catheter over the guidewire. In ultra small diameter catheter designs, it may be desirable to coat the outside surface of the guidewire 40 and/or the inside surface of the wall defining lumen 38 with a lubricous coating to minimize friction as the catheter 10 is axially moved with respect to the guidewire 40. A variety of coatings may be utilized, such as Parylene, Teflon, silicone rubber, polyimide-p-polytetrafluoroethylene composite materials or others known in the art and suitable depending upon the material of the guidewire or inner tubular wall 38.

Figure 4B:
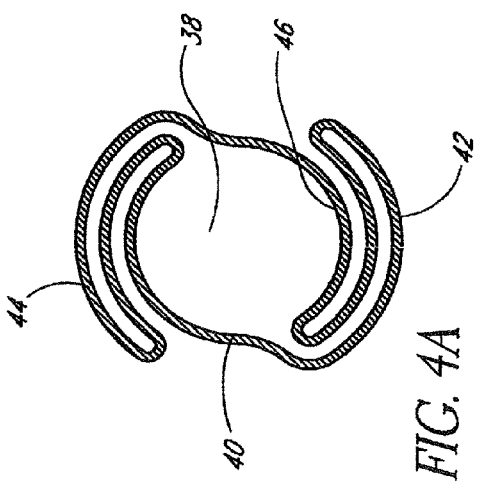
FIG. 4B is a cross-sectional view as in FIG. 4A, showing an alternate folding pattern, according to an embodiment of the invention.
Figure 4A:
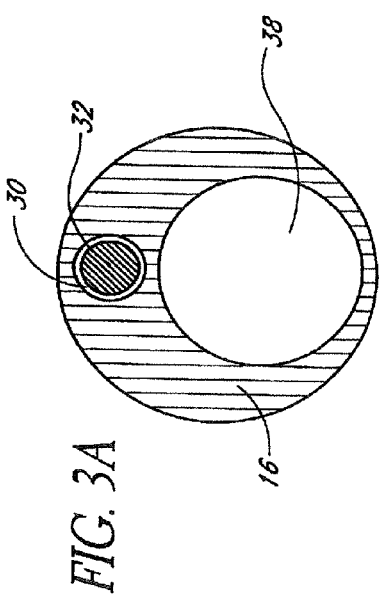
FIG. 4A is a cross-sectional view taken along the line 4-4, schematically showing a folding pattern for the distal section, according to an embodiment of the invention.

In an alternate configuration, as illustrated in FIG. 4B, the tubular wall 40 is provided with a plurality of wings 46. Each of these may be folded and provided with a heat set to produce a reduced diameter configuration. Alternatively, the tubular wall 40 may be extruded in the winged configuration, depending upon the desired manufacturing technique.

Referring to FIGS. 5 and 6, a movable support 50 is provided for enlarging the distal section 34 from the reduced diameter to the enlarged diameter configuration. In the illustrated embodiment, the movable support 50 is in the form of an axially movable coil 52. Coil 52 is mechanically linked to the control 24 by an axially movable control wire 32. Distal advance of the control 24 causes the control wire 32 to advance distally through the control wire lumen 30, thereby advancing the movable coil 52 from a position within the proximal section 33, across the transition 32 and into the distal section 38. This causes the distal section 38 to move from the reduced diameter to the enlarged diameter configuration.

The coil 52 resists collapse of the tubular wall 40 when vacuum is applied to the central lumen 38. Due to the radial support characteristics of the movable coil 52, the wall thickness of the tubular wall 40 may be minimized to a limit which is determined by physical characteristics of the polymer, together with the spacing between adjacent filars of the movable coil 52. Optimal relationships between these variables can be determined through routine experimentation by those of ordinary skill in the art, in view of the disclosure herein.

The use of an axially movable coil 52 is believed to enable both radial enlargement of the distal aspiration lumen 38, as well as placement of a large ID aspiration lumen in small vessels, even around corners in the vasculature. The catheter can be placed within torturous vasculature while in the low profile configuration, to reach a remote site. Distal advance of the support coil within the catheter can then track through the tortuous vasculature while radially enlarging the aspiration lumen. This is enabled through the use of a laterally flexible tubular support, such as a helix, spring, micro slotted tube or other tubular support with lateral flexibility. In this manner, the distal section 34 may be positioned within portions of the anatomy and then enlarged to a diameter, which would not have been able to axially traverse the vasculature without unacceptable levels of vascular trauma, using conventional catheter constructions.

The exact configuration of the moveable support 50 may be varied considerably, and still accomplish the objectives of the present invention. For example, referring to FIGS. 7 and 8, the moveable support 50 is in the form of a helical ribbon 54. The helical ribbon 54 may be provided by helically cutting through the wall of a segment of the distal end of a tube 56 using techniques, which are disclosed elsewhere herein. Thus, as illustrated in FIG. 8, a support zone 58 is provided on the distal end of a tube 56. Tube 56 may extend concentrically within the central lumen 38 proximally to the manifold 18, or to a control on the proximal catheter shaft. Alternatively, 256 may be in mechanical communication with the control 24 by way of an axially moveable control wire 32 as has been discussed. Ribbon 54 may alternatively be formed by wrapping around a mandrel, or other techniques which will be known to those of skill in the art.

Aspiration catheters of the present invention, which are adapted for intracranial applications, generally have a total length in the range of from 60 cm to 250 cm, usually from about 135 cm to about 175 cm. The length of the proximal segment 33 will typically be from 20 cm to 220 cm, more typically from 100 cm to about 120 cm. The length of the distal segment 34 will typically be in the range from 2 cm to about 50 cm, usually from about 5 cm to about 20 cm. The proximal and distal body segments 33, 34 may be joined to each other, i.e. at a transition 32. The body segments may be joined in any of a variety of conventional manners, such as heat fusion, adhesive bonding, co-extrusion, or the like. In the exemplary embodiment, the two body segments 33, 34 will be formed separately and thereafter fused together by the application of heat with a removable mandrel extending through each lumen, which crosses the transition 32 to maintain patency. A length of outer shrink-wrap tubing may be used to add structural integrity by spanning the transition 32.

The catheters of the present invention may be composed of any of a variety of biologically compatible polymeric resins having suitable characteristics when formed into the tubular catheter body segments. Exemplary materials include polyvinyl chloride, polyethers, polyamides, polyethylenes, polyurethanes, copolymers thereof, and the like. In certain embodiments, in which the distal segment 34 dilates (stretches) radially rather than unfolds, the distal segment 34 may be formed from more elastic materials, such as latex rubber, silicone rubber, and blends thereof. In one embodiment, both the proximal body segment 33 and distal body segment 34 will comprise a polyvinyl chloride (PVC), with the proximal body segment being formed from a relatively rigid PVC and the distal body segment being formed from a relatively flexible, supple PVC. Optionally, the proximal body segment may be reinforced with a metal or polymeric braid or other conventional reinforcing layer.

The proximal body segment will exhibit sufficient column strength to permit axial positioning of the catheter through a guide catheter at least a portion of with the distal body segment 34 extending into the patient's vasculature. The proximal body segment may have shore hardness in the range from 50 D to 100 D, often being about 70 D to 80 D. Usually, the proximal shaft will have a flexural modulus from 20,000 psi to 1,000,000 psi, preferably from 100,000 psi to 600,000 psi. The distal body segment will be sufficiently flexible and supple so that it may navigate the patient's distal vasculature. In highly flexible embodiments, the shore hardness of the distal body segment 34 may be in the range of from about 20 A to about 100 A, and the flexural modulus for the distal segment 34 may be from about 50 psi to about 15,000 psi.

The catheter body may further comprise other components, such as radiopaque fillers; colorants; reinforcing materials; reinforcement layers, such as braids and helical reinforcement elements; or the like. In particular, the proximal body segment may be reinforced in order to enhance its column strength and torqueability while preferably limiting its wall thickness and outside diameter.

The pleated or otherwise reduced diameter of the distal body segment 34 will usually be smaller than that of the proximal body segment. In some intracranial applications, the proximal body segment will have a constant diameter, with an outer diameter in the range from 0.33 mm to 2 mm, usually from 0.67 mm to 1.67 mm, and an inner diameter in the range from 0.1 mm to 1.75 mm, usually from 0.2 mm to 1 mm. The distal body segment can be tapered, where its proximal end has a diameter, which generally is the same as that of the distal end of the proximal body segment and its distal end has a diameter no greater than the range set forth above.

Usually, radiopaque markers will be provided at least at the distal end 25 and the transition region 32 between the proximal and distal body segments 33, 34. Other radiopaque markers may be provided elsewhere, such as on the support coil, if it is not already radiopaque. One radiopaque marker comprises a metal band, which is fully recessed within the distal end of the proximal body segment 33. Suitable marker bands can be produced from a variety of materials, including platinum, gold, and tungsten/rhenium alloy. Preferably, the radiopaque metal band will be recessed in an annular channel formed at the distal end of the proximal body segment.

The proximal section 33 of tubular body 16 may be produced in accordance with any of a variety of known techniques for manufacturing interventional catheter bodies, such as by extrusion of appropriate biocompatible polymeric materials. Alternatively, at least a proximal portion or all of the length of tubular body 16 may comprise a polymeric or metal spring coil, solid walled hypodermic needle tubing, or braided reinforced wall, as is known in the microcatheter arts.

In many applications, the proximal section 33 of tubular body 16 is provided with an approximately circular cross-sectional configuration having an external diameter within the range of from about 0.025 inches to about 0.065 inches. In accordance with one embodiment of the invention, the proximal section 33 of tubular body 16 has an external diameter of about 0.042 inches (3.2 f) throughout most of its length. Alternatively, a generally oval or triangular cross-sectional configuration can also be used, as well as other noncircular configurations, depending upon the method of manufacture, number and arrangement of internal lumens and the intended use.

In a catheter intended for peripheral vascular applications, the proximal section 33 of body 16 will typically have an outside diameter within the range of from about 0.039 inches to about 0.065 inches. In coronary vascular applications, the proximal section 33 of body 16 will typically have an outside diameter within the range of from about 0.025 inches to about 0.045 inches. The illustrated construction of distal section 34 permits lower external cross-sections in the collapsed configuration, as low as 0.028 inches or 0.025 inches or 0.022 inches or lower as may be desired for remote coronary or intracranial applications.

Diameters outside of the preferred ranges may also be used, provided that the functional consequences of the diameter are acceptable for the intended purpose of the catheter. For example, the lower limit of the diameter for any portion of tubular body 16 in a given application will be a function of the number of fluid or other functional lumen contained in the catheter, together with the acceptable minimum aspiration flow rate and collapse resistance.

Tubular body 16 must have sufficient structural integrity (e.g., column strength or "pushability") to permit the catheter to be advanced to distal locations without buckling or undesirable bending of the tubular body. The ability of the body 16 to transmit torque may also be desirable, such as to avoid kinking upon rotation, to assist in steering. The tubular body 16, and particularly the distal section 34, may be provided with any of a variety of torque and/or column strength enhancing structures. For example, axially extending stiffening wires, spiral wrapped support layers, braided or woven reinforcement filaments may be built into or layered on the tubular body 16. See, for example, U.S. Pat. No. 5,891,114 to Chien, et al., the disclosure of which is incorporated in its entirety herein by reference.

In many applications, the proximal section 33 will not be required to traverse particularly low profile or tortuous arteries. For coronary vascular applications, for example, the proximal section 33 will be mostly or entirely within the relatively large diameter guide catheter. The transition 32 can be located on the catheter shaft 16 to correspond approximately with the distal end of the guide catheter when the balloon 24 and/or distal end 14 is at the treatment site. Viewed the other way, the length of the distal section 34 is preferably at least as long as the distance from the ostium of the relevant coronary artery to the treatment site. In most applications, the transition 32 will be at least about 3 cm, preferably at least about 5 cm and alternatively as much as about 10 cm but often not more than about 20 cm from the distal end of the catheter. Distances as much as 30 cm to 50 cm or greater between the transition 32 and distal end of the catheter may also be desirable in some applications.

For certain other applications, such as intracranial catheterizations, the distal section 34 is preferably at least about 5 cm long and small enough in diameter to pass through vessels as low as 3 mm or 2 mm or lower. Catheters for this application may have a proximal section length of between about 60 cm to about 150 cm and a distal section length of between about 5 cm to about 15 cm, and the distal section is able to track a tortuous path of at least about 5 cm through vessels of less than about 3 mm lumen ID. Further structure, dimensional and method disclosure can be found in U.S. Pat. No. 4,739,768 to Engelson, the disclosure of which is incorporated in its entirety herein by reference.

The distal section 34, may be manufactured as an extrusion. In one method of manufacture, the extrusion is formed from a medium to high melt index polyethylene or other polymer having an outside diameter of greater than the diameter of the desired finished product. The raw extrusion can thereafter be drawn down to the desired diameter, in accordance with known processing techniques. The draw down pull speed can be varied such as along a proximal portion of the extrusion to produce a taper to a larger proximal diameter. This permits a smooth transition 32 from the relatively smaller outside diameter distal section 34 to the typically larger outside diameter of proximal section 33. High melt index materials allow the production of a greater number of different diameter draw downs by adjusting pull speed and other process parameters, for a given set of tooling as will be appreciated by those of skill in the art. The distal end 14 can be further reduced in diameter by an additional draw down step if desired.

Figure 7:
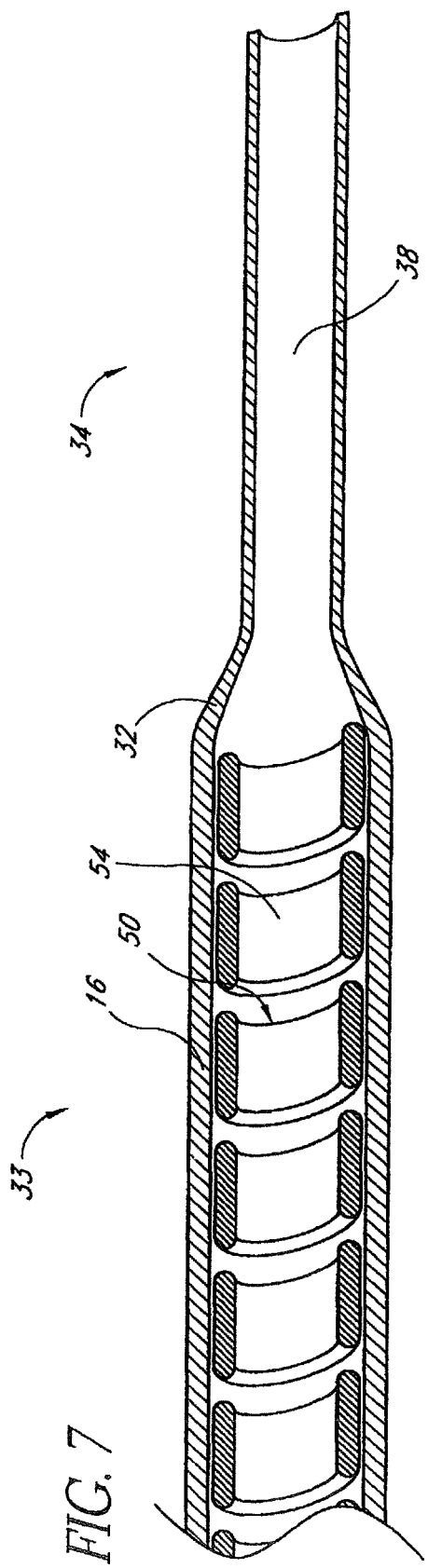
FIG. 7 is a cross-sectional view as in FIG. 5, showing an alternate support coil in a proximal position, according to an embodiment of the invention.
Figure 8:
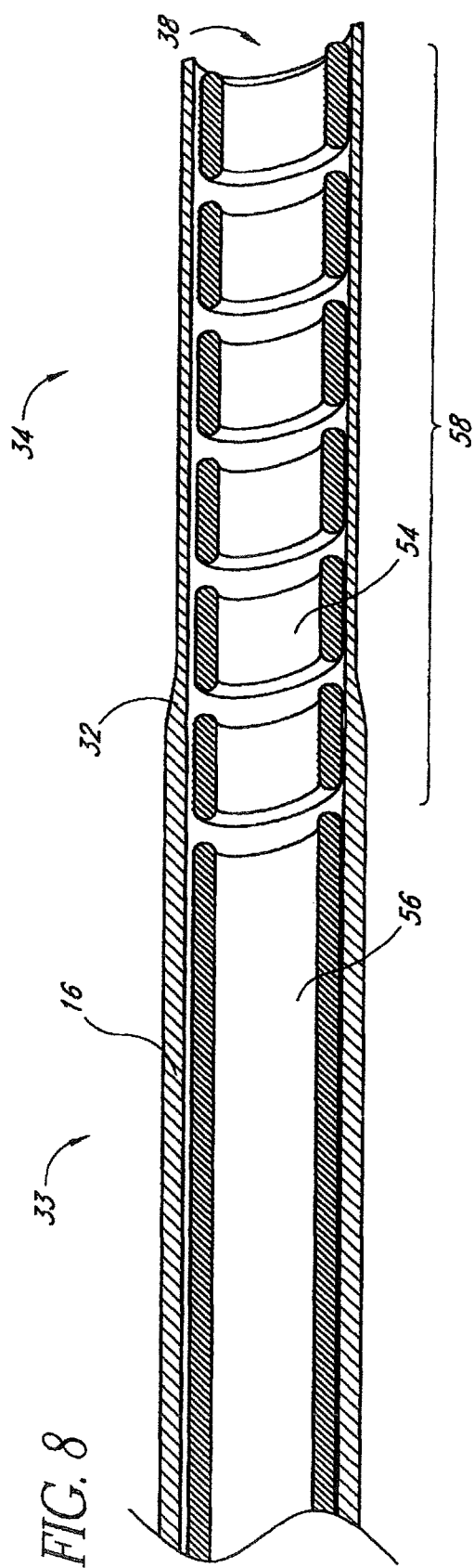
FIG. 8 is a cross-sectional view as in FIG. 7, with the alternate support coil in a distal position, according to an embodiment of the invention.

Referring to FIGS. 7 and 8, the axially moveable support may be provided in the form of an elongate flexible tube 56. A distal section 58 of tubular element 56 is provided with a spiral cut, to retain radial strength but provide lateral flexibility. The spiral cut section 58 generally has a length within the range of from about 1 centimeter to 15 centimeters, preferably within a range of about 5 centimeters to about 12 centimeters, and, in a particular embodiment, extends for approximately 10 centimeters in length. The spiral cut generally has a pitch within the range of from about 0.01 inches to about 0.125 inches, and in one embodiment, has a 0.06 pitch. In another embodiment, the distal section 32 comprises a first spiral cut section having a length of about 5 cm and a pitch of about 0.06, and a second, distal section having a length of about 5 cm and a pitch of about 0.030.

Preferably, the spiral cut extends completely through the wall of the tubular element 56 to produce a helical or coiled configuration. The precise pitch of the spiral cut and axial spacing of adjacent windings can be varied widely while still accomplishing the purposes of the present invention, and can be optimized for any particular application in view of the disclosure herein.

For example, polytetrafluoroethylene tubing, such as that suitable for tubular element 30, can be commercially obtained from Zeus, in Orangeburg, S.C. The distal section 32 can be provided with a spiral cut, such as by any of a variety of techniques that can be devised by those of skill in the art. In accordance with one technique, the PTFE or other tubing is placed onto a mandrel. The mandrel is attached to a machine with a predetermined screw thread. A cutting element such as a razor blade or other sharp instrument is placed across the tubing and the machine is activated to rotate the mandrel. As rotation of the machine (screw thread) occurs, the mandrel moves axially and rotationally causing the tubing to be cut in a spiral manner by the cutting implement. The machine can be set up to cut either a right or left hand spiral. The machine can also be set to cut continuous or variable pitch spirals, or multi-zone spiral sections in which each zone has a unique pitch. A metal spring coil 34 can be wrapped about a suitably sized rotating mandrel as is known in the art, with the distal open wound section 36 formed by stretching.

The tubular support 58 may alternatively be in the form of a wire spring, extending throughout the length of the distal segment or entire catheter. See Generally FIGS. 5 and 6. A distal section 36 of the coil spring 52 is stretched axially to produce an open wound configuration, such that the axial space between adjacent windings of the coil may be within the range of from about 0.05 mm to about 1 mm or greater. The proximal portion of coil spring 34 is generally bottomed out (not illustrated), such that adjacent windings of the coil are in contact with one another. This provides column strength, to allow distal advancement within the catheter, while retaining lateral flexibility. Alternatively, the coil spring can be open wound with, e.g., 0.01 mm to 1 mm spacing for the entire length.

A variety of materials can be used to construct the coil spring 52, such as stainless steel, platinum, platinum alloy, nickel, or titanium alloys. Coil spring 52 can be produced from any of a variety of stock forms, such as round cross-sectional wire, square or other rectangular wire, or polymeric materials as are known in the art. In one embodiment, coil spring 52 is wound from a flat wire made from stainless steel and having cross-sectional dimensions of about 0.002 by about 0.006 inches.

The cerebral circulation is regulated in such a way that a constant total cerebral blood flow (CBF) is generally maintained under varying conditions. For example, a reduction in flow to one part of the brain, such as in acute stroke, may be compensated by an increase in flow to another part, so that CBF to any one region of the brain remains unchanged. More importantly, when one part of the brain becomes ischemic due to a vascular occlusion, the brain compensates by increasing blood flow to the ischemic area through its collateral circulation.

Figure 9:
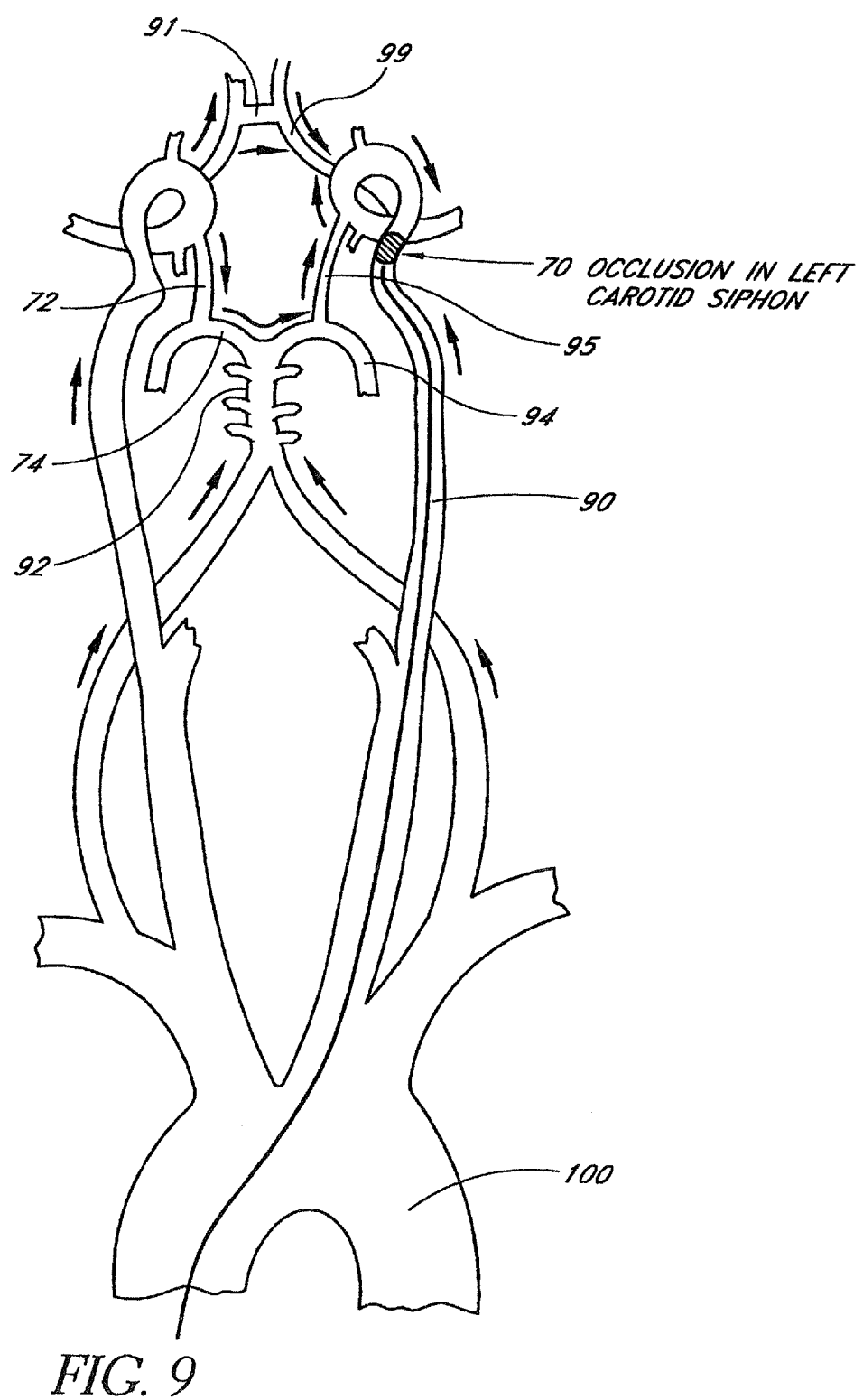
FIG. 9 is a schematic representation of the reversed circulation in the circle of Willis, to compensate for an occlusion in the left carotid siphon artery, with a guidewire extending through the left internal carotid artery to the occlusion, according to an embodiment of the invention.

FIG. 9 depicts a normal cerebral circulation and formation of Circle of Willis. Aorta 100 gives rise to right brachiocephalic trunk 82, left common carotid artery (CCA) 80, and left subclavian artery 84. The brachiocephalic artery further branches into right common carotid artery 85 and right subclavian artery 83. The left CCA gives rise to left internal carotid artery (ICA) 90 which becomes left middle cerebral artery (MCA) 97 and left anterior cerebral artery (ACA) 99. Anteriorly, the Circle of Willis is formed by the internal carotid arteries, the anterior cerebral arteries, and anterior communicating artery 91 which connects the two ACAs. The right and left ICA also send right posterior communicating artery 72 and left posterior communicating artery 95 to connect, respectively, with right posterior cerebral artery (PCA) 74 and left PCA 94. The two posterior communicating arteries and PCAs, and the origin of the posterior cerebral artery from basilar artery 92 complete the circle posteriorly.

When an occlusion occurs acutely, for example, in left carotid siphon 70, as depicted in FIG. 9, blood flow in the right cerebral arteries, left external carotid artery 78, right vertebral artery 76 and left vertebral artery 77 increases, resulting in directional change of flow through the Circle of Willis to compensate for the sudden decrease of blood flow in the left carotid siphon. Specifically, blood flow reverses in right posterior communicating artery 72, right PCA 74, left posterior communicating artery 95. Anterior communicating artery 91 opens, reversing flow in left ACA 99, and flow increases in the left external carotid artery, reversing flow along left ophthalmic artery 75, all of which contribute to flow in left ICA 90 distal the occlusion to provide perfusion to the ischemic area distal to the occlusion. A guidewire is illustrated in position proximal to the occlusion.

In use, the distal end of the aspiration catheter 10 is inserted through an incision on a peripheral artery over the guidewire into a more distal carotid or intracranial artery, such as the terminal ICA, carotid siphon, MCA, or ACA. Thromboembolic material 202 is shown occluding the lumen of a cerebral artery narrowed by atheromatous plaque 200. The occlusion site can be localized with cerebral angiogram or IVUS. In emergency situations, the catheter can be inserted directly into the symptomatic carotid artery after localization of the occlusion with the assistance of IVUS or standard carotid Doppler and TCD.

Figure 10:
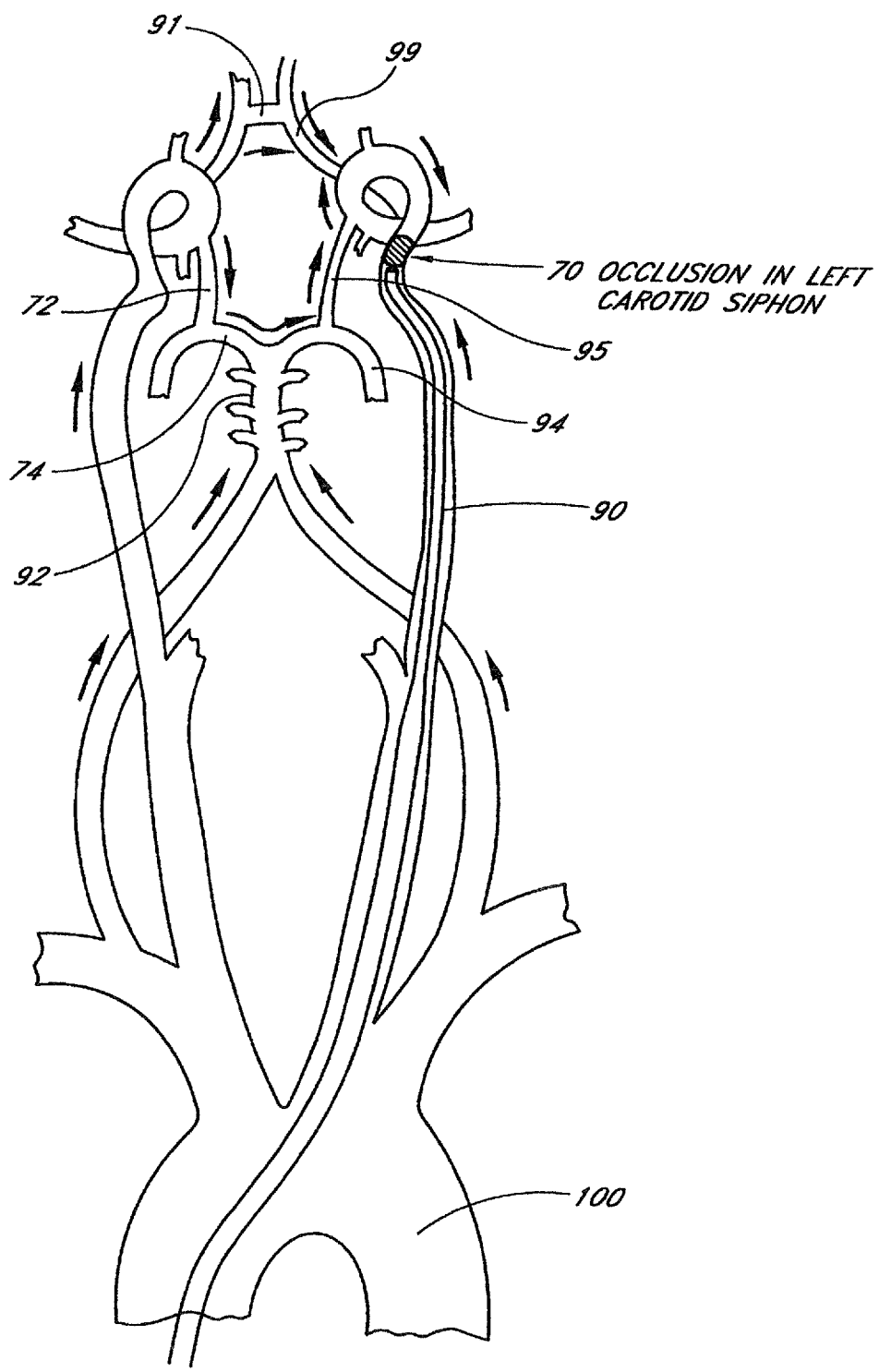
FIG. 10 is a schematic illustration as in FIG. 9, with an intracranial aspiration catheter advanced to the occlusion, in the reduced diameter configuration, according to an embodiment of the invention.

As illustrated in FIG. 10, the catheter 10 is transluminally navigated along or over the guidewire, to a position just proximal to the occlusion. Transluminal navigation is accomplished with the distal section of the catheter in the first, reduced cross sectional configuration. This enables navigation of tortuous vasculature which a larger cross section may not be able to traverse.

Figure 11:
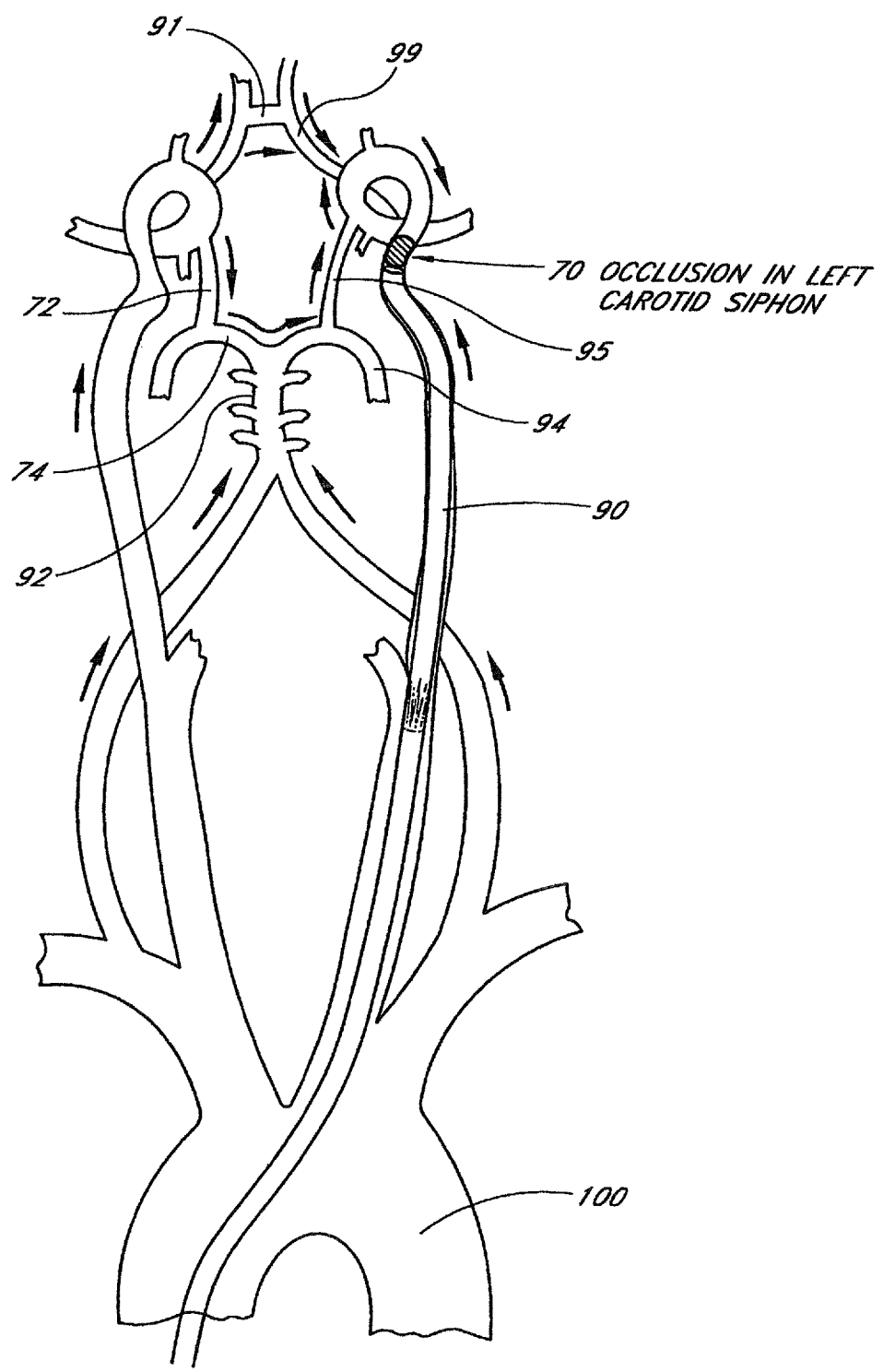
FIG. 11 is a schematic representation as in FIG. 10, with the distal section of the catheter in the enlarged diameter configuration, according to an embodiment of the invention.

Referring to FIG. 11, the cross section of the distal segment is enlarged after the catheter has been positioned, such as by distally axially advancing a tubular support as has been described previously. This allows a larger inside diameter aspiration lumen than would otherwise have been navigable to the treatment site. In addition, the use of a coil or spiral wrapping as the tubular support enables the distal segment to be expanded through curves in the vasculature, without kinking or straightening the vasculature. As will be appreciated from even the simplified schematic of the cerebral vasculature shown in FIG. 11, the length of the distal section may be varied depending upon the intended target site for the catheter. Since the inside diameter of the vasculature decreases distally, the length and collapsed crossing profile of the distal section is designed to take into account the length and inside diameter of the vessel leading up to a target occlusion.

Figure 12:
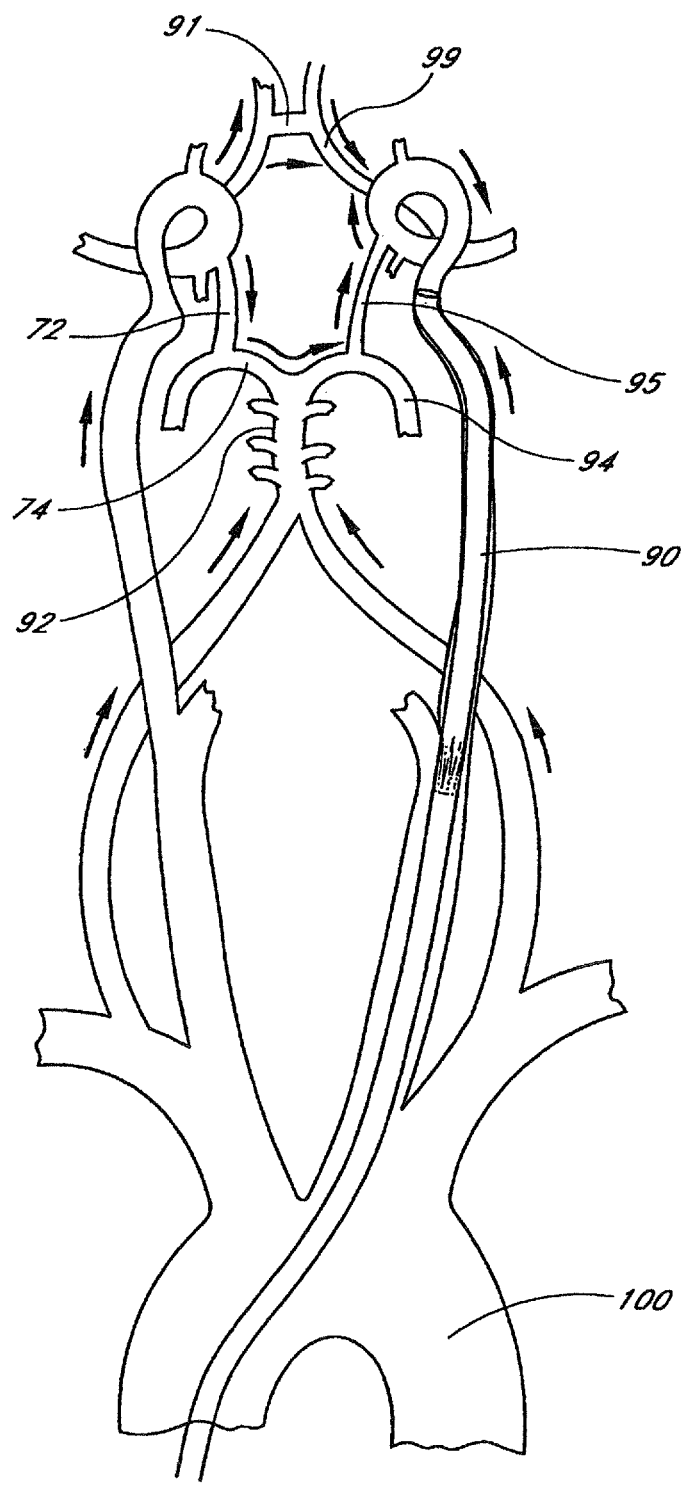
FIG. 12 is a schematic representation as in FIG. 11, following aspiration of the occlusion through the enlarged diameter of the aspiration catheter, according to an embodiment of the invention.

Aspiration is thereafter applied to the aspiration lumen, thereby drawing the occlusion into the catheter as illustrated in FIG. 12. The distal section may thereafter be reduced in cross section, and the catheter proximally retracted from the patient. A vasodilator, e.g., nifedipine or nitroprusside, may be injected through lumen 38 and port 25 to reverse vascular spasm induced as a result of instrumentation.

Pressure may be monitored by a manometer and can be altered by applying vacuum to the proximal end of the catheter. A pressure dial, which may be included in the proximal end of the catheter, allows suction within the vessel to be regulated. When continuous negative pressure is applied, occluding material 202 is dislodged into aspiration port 25 and proximally through aspiration lumen 38.

If the occlusion is not removed by the above continuous suction method, intermittent suction can be used to create an alternating negative-positive pressure gradient, which may dislodge the thromboembolic occlusion. Alternatively, a thrombolytic agent, e.g., t-PA may be infused through lumen 38 and port 25 to lyse the occlusion if soft thrombus is suspected. Standard atherectomy or angioplasty with or without stent placement can also be performed on atheromatous plaque after removal of the occlusion if perfusion through the diseased artery is still inadequate.

Focal hypothermia, which has been shown to be neuroprotective, can be administered by perfusing hypothermic oxygenated blood or fluid. Perfusion through port 25 can be achieved by withdrawing venous blood from a peripheral vein and processing through a pump oxygenator, or by withdrawing oxygenated blood from a peripheral artery, such as a femoral artery, and pumping it back into the carotid artery.

If suction fails to dislodge the occlusion, a thrombolytic agent, e.g., t-PA, can be infused through lumen 38 and port 25 to lyse any thrombotic material with greater local efficacy and fewer systemic complications. Administration of thrombolytic agent, however, may not be recommended for devices, which are inserted directly into the carotid artery due to increased risk of hemorrhage. If perfusion is continued for more than a few minutes, removal of excess fluid from the circulation is required to avoid fluid overload. Fluid can be withdrawn from a jugular vein or from any other peripheral vein or artery, e.g., the femoral vein or artery, and re-introduced into the symptomatic artery. Moderate hypothermia, at approximately 32 to 34 degrees Centigrade, can be introduced during the fluid recirculation.

In patients with vertebral artery occlusions, treatment with angioplasty often results in disastrous complications due to embolization of the occlusive lesion downstream to the basilar artery. Emboli small enough to pass through the vertebral arteries into the larger basilar artery are usually arrested at the top of the basilar artery, where it bifurcates into the posterior cerebral arteries. The resulting reduction in blood flow to the ascending reticular formation of the midbrain and thalamus produces immediate loss of consciousness. The devices described in FIG. 1 through FIG. 8 can be used to remove thromboembolic material from the vertebral artery. The occlusion site is first localized with transcranial Doppler and angiogram. The catheter 10 can be inserted through an incision on a peripheral artery into the symptomatic vertebral artery or the subclavian artery. For example, the distal end of catheter 10 may be inserted proximal to thromboembolic material 202 in right vertebral artery 87 and left subclavian artery 84. When continuous or intermittent suction is applied to the distal end of the catheter, the pressure gradient across the occluding lesion increases and thromboembolic material 202 may be dislodged and captured by the aspiration port. The thromboembolic material may thereafter be removed continuous or pulsed suction, thereby reducing the risk of embolization to the basilar artery.

Access for the catheter of the present invention can be achieved using conventional techniques through an incision on a peripheral artery, such as right femoral artery, left femoral artery, right radial artery, left radial artery, right brachial artery, left brachial artery, right axillary artery, left axillary artery, right subclavian artery, or left subclavian artery. An incision can also be made on right carotid artery or left carotid artery 130 in emergency situations.

The length of the catheter for those access sites to reach the brain will generally be between 20 to 100 centimeters, preferably approximately between 30 and 60 centimeters. The inner diameter of the catheter may be between 0.2 and 0.6 centimeters, or smaller. The foregoing ranges are set forth solely for the purpose of illustrating typical device dimensions. The actual dimensions of a device constructed according to the principles of the present invention may obviously vary outside of the listed ranges without departing from those basic principles.

FIG. 13A illustrates a microcatheter 100 comprising an outer shaft 102 further comprising an outer shaft lumen 118, a hub 104 further comprising a proximal Luer lock adapter 120, a distal shaft 116 further comprising a distal shaft lumen 106, a distal constriction 108, a proximal constriction 128, and an expandable member 110 further comprising a proximal bond 114 and a distal bond 112. The expandable member 110 is illustrated in its diametrically expanded configuration.

Referring to FIG. 13A, the proximal end of the outer shaft 102 is affixed to the distal end of the hub 104. The inner lumen 118 of the outer shaft 102 is operably connected to the tapered lumen 130 of the hub 104 such that there are minimal or no bumps or obstructions to passage of catheters or guidewires from the tapered lumen 130 into the outer shaft inner lumen 118. The proximal end of the distal shaft 116 is slidably disposed within the distal end of the outer shaft 102. The proximal end of the expandable member 110 is affixed to the outer shaft 102 by the proximal bond 114. The distal end of the expandable member 110 is affixed to the distal shaft 116 by the distal bond 112. The expandable member 110 retains a minimum and a maximum overall length between the distal bond 112 and the proximal bond 114 such that the overlap distance between the two telescoping tubes 102 and 116 is maintained to a minimum of about 1-cm. The distal constriction 108 is affixed within the lumen 106 to the distal shaft 116. The distal constriction 108 further comprises a central lumen (not shown) having an undeformed, or unstressed, diameter smaller than that of the guidewire 124 meant to be inserted therethrough. The lumen diameter of the distal constriction 108, or region of reduced diameter, can have a diameter of between 100% and 10% of the guidewire 124, and preferably between 40% and 80% of that of the guidewire 124. The central lumen (not shown) of the distal constriction 108 can expand to accommodate insertion of the guidewire 124 but imparts substantial friction on the guidewire 124. The proximal constriction 128 is affixed to the interior wall of the outer shaft 102 and within the lumen 118. The proximal face of the proximal constriction 128 can have an inwardly tapered funnel-like lead-in to the central lumen of the proximal constriction 128. This lead-in (not shown) can facilitate coercing the guidewire 124 into the central lumen of the proximal constriction 128. This is especially important in the larger diameter inner lumen 118 of the outer shaft 102. The guidewire 124 can be an elongate member configured to collapse/expand the expandable member or region 110. The elongate member may also be a linkage, mechanical linkage, pushrod, push-pull rod, or the like. The guidewire 124, or linkage, preferably comprises the properties of high column strength, high tensile strength, low elongation and high flexibility.

The hub 104 can be affixed to the outer shaft 102 by processes such as, but not limited to, adhesive bonding, heat welding, overmolding, insert-molding, ultrasonically welding, or the like. The proximal bond 114 and the distal bond 112 can be created using processes such as, but not limited to, adhesive bonding, heat welding, overmolding, insert-molding, ultrasonic welding, wrapping, mechanical fixation, encapsulation, and the like.

The overall working length of the microcatheter 100 can range between about 50 cm and 200 cm with a preferred range of about 100 cm to 175 cm. The outside diameter of the outer shaft 102 can range between about 0.5 French and 10 French with a preferred range of about 1-French to 4-French. The length of the expandable member 110 in its radially expanded configuration can range between about 1 cm and 20 cm with a preferred length range of about 2 cm and 10 cm and a most preferred range of 2.5 cm to 5 cm. The length of the tapered regions at the end of the expandable member 110 can each range between about 5% and 40% of the total length of the expandable member 110. The expandable member 110 can have an expanded diameter ranging from about 1-French to 13 French with a preferred diameter of about 2-French to 5 French. The diameter of the guidewire 124 can range between about 0.005 and 0.015 with a preferred range of 0.008 to 0.012.

The materials appropriate to the construction of the microcatheter 100 are biocompatible and sterilizable. The outer shaft 102 and the distal shaft 116 can be fabricated from relatively materials such as, but not limited to, PTFE, Pebax, Hytrel, polyurethane, polyethylene, polyimide, polyamide, polyester, PEEK, and the like. The construction of the distal shaft 116 and the outer shaft 102 can be such that flexibility, torqueability, and column strength, all beneficial to a catheter, are maintained. The distal shaft 116 and the outer shaft 102 can be of singular material construction or one or both can be of composite, or built-up, construction. Such composite construction can comprise a polymeric inner and outer coat or surround enveloping a reinforcement layer. The reinforcement layer can comprise braid, coil, or stent-shaped construction fabricated from materials such as, but not limited to, stainless steel, tantalum, titanium, nitinol, polyester, PEN, cobalt nickel alloy, polyamide, polyimide, and the like. The hub 104 can be fabricated from more rigid materials such as, but not limited to, acrylonitrile butadiene styrene (ABS), polyethylene, polypropylene, polyamide, polyimide, polyether ether ketone (PEEK), polysulfone, and the like. The mesh 110 can be fabricated from nitinol, stainless steel, titanium, cobalt nickel alloy, tantalum, polyimide, polyamide, polyester, and the like. In other embodiments, the outer shaft 102 can have variable flexibility characteristics along its length. In certain embodiments, the outer shaft 102 can comprise continuously varying properties. In certain of the continuously varying property embodiments, the outer shaft 102 can be progressively more flexible moving from the proximal end toward the distal end. In certain embodiments, the outer shaft 102 can comprise a plurality of regions of discreet flexibility. The number of regions of discreet flexibility can range between 2 and 10 and preferably between 2 and 5. The regions closer to the distal end can be made advantageously more flexible than regions closer to the proximal end of the outer shaft 102. Such changes in flexibility, for example moving from higher stiffness to lower stiffness, can be achieved by methods such as, but not limited to, changing the polymer composition to lower hardness materials, changing the pitch of a coil reinforcement to provide greater spacing between coils, changing the pitch of a braided reinforcement to achieve greater spacing, changing the thickness of the wires used in a coil or braid to smaller dimensions, or the like.

The bars of the mesh 110 can comprise round, oval, rectangular, or other suitable cross-sectional shape. The mesh 110 can also be configured as a slotted tube, or a plurality of bars oriented substantially parallel to the longitudinal axis of the distal member 116. The mesh 110 can also be configured with all the patterns disclosed for various implantable stent devices.

The overlap region between the distal shaft 116 and the outer shaft 102 permits relative motion between the two shafts 116 and 102 while the expandable member 110 changes its length in response to operator control. This length changing feature can also be accomplished by affixing a helically disposed tube, a serpentine tube, a coil, a braided tube, or other structure that can substantially maintain its shape but change length in response to external forces to the outer shaft 102, the distal shaft, 116, or both.

FIG. 13B illustrates the microcatheter 100 of FIG. 1A illustrated with a guidewire 124 inserted therethrough and the expandable member 110 in its diametrically constricted configuration. The microcatheter 100 comprises the hub 104, which is illustrated in cross-section, and further comprises a tapered lead in lumen 130. The microcatheter 100 further comprises the outer shaft 102, the outer shaft lumen 118, the distal shaft 116, the distal shaft lumen 106, the distal constriction 108, the proximal constriction, the distal bond 112, the proximal bond 114, the guidewire 124, and the guidewire proximal cap 126.

Referring to FIG. 13B, the guidewire 124 has been inserted through the lumen 130 of the hub 104 and into the lumen 118 of the outer shaft 102. The guidewire 124 is routed through the optional proximal constriction 128, into the inner lumen 106 of the distal shaft 116, through the distal constriction 108 and out the distal end of the inner lumen 106. It is also possible that the guidewire 124 will not pass entirely through the distal constriction 108, in which case, the guidewire 124 would also not extend beyond the distal end of the inner lumen 106. The guidewire proximal cap 126 is affixed to the proximal end of the guidewire 124. The guidewire proximal cap 126 is removably affixed to the Luer lock fitting 120 on the hub 104. The guidewire 124 is longitudinally fixed relative to the inner shaft 118 and the distal constriction 108 by locking the cap 126 to the hub 104. Distal motion of the guidewire 124 through the distal constriction 108 causes sufficient longitudinal stretching force, due to application of friction by the distal constriction 108, such that the expandable member 110 becomes stretched longitudinally to its maximum extent and thus the expandable member 110 assumes its minimum radial dimension.

The proximal constriction 128 is optional but the friction supplied by the proximal constriction 128 on the guidewire 124 can be used to stabilize the guidewire and maintain the expandable member 110 in its fully stretched state without the need for the cap 126. Note that the distal constriction 108 and the proximal constriction 128 are of different outside diameters to permit them to be affixed inside different diameter tubes but the diameters of the constrictions 108 and 128 can be tailored to the specific configuration of the catheter. The constrictions 108 and 128 can be of single material or multiple material layer construction. They can be fabricated from materials configured to generate high friction such as, but not limited to, silicone elastomer, latex rubber, thermoplastic elastomer, polyurethane, and the like. These elastomeric materials can be fabricated free from oils or other lubricants and with surface properties that generate high friction on the outside surface of the guidewire 124. The guidewire 124 can beneficially be constructed using an outer surface that is non-lubricious. Thus the guidewire 124 can have at least a part of its outer surface free from coating with materials such as PTFE, Teflon, FEP, or the like.

Figure 14A:
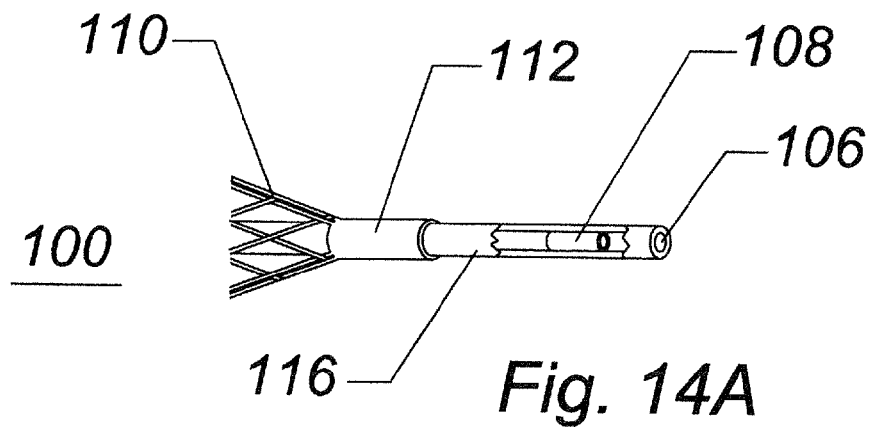
FIG. 14A illustrates a detail of the distal region of the catheter of FIG. 13A showing the guidewire constriction or aperture and a radially expanded, expandable element, according to an embodiment of the invention.

FIG. 14A illustrates a detailed image of the distal end of the microcatheter 100, with the expandable member 110 in its diametrically expanded state, further comprising the distal bond 112, the distal shaft 116 further comprising the lumen 106, and the distal constriction 108.

Referring to FIG. 14A, the expandable member 110, in the illustrated embodiment, is a mesh or braid of filaments, the mesh being bonded to the distal shaft 116 by the distal bond 112. The distal shaft 116 is shown in partial breakaway view to reveal the distal constriction 108. The mesh expandable member can be malleable, elastomeric or configured as a spring, or it can be shape memory. The mesh 110, in its malleable configuration can be fabricated from annealed stainless steel, tantalum, gold, platinum, platinum-iridium, titanium, annealed cobalt nickel alloy, certain aforementioned polymers, and the like. In an embodiment where the mesh 110 is elastomeric, the fibers or filaments can be fabricated from materials such as, but not limited to, spring hardness stainless steel, cobalt nickel alloy, superelastic nitinol, shape memory nitinol, or the like. In certain elastomeric embodiments, the expandable member or mesh 110 can be biased into its maximum diameter configuration so that upon removal of any stretching force, the expandable member 110 assumes its maximum diameter configuration. In the case of nitinol, an austenite finish (Af) temperature of about 20° C. or lower, and preferably 15° C. or lower, is beneficial to maximize spring properties at body temperature. In embodiments where the expandable member 110 comprises shape memory properties, the expandable member 110 can be fabricated from nitinol and have an austenite finish temperature of around 28 to 3220 C. in order to permit full expansion radially at about body temperature of around 37° C. In the case of nitinol embodiments, either superelastic, pseudoelastic, or shape memory, the nitinol structure can be shape set into the desired configuration to which it will remain biased, near or above its austenite finish temperature. In the illustrated embodiments, removal of any external forces can include removing the guidewire 124 from within the lumen 106 of the distal shaft 116.

The nitinol material, as described herein, is a nickel titanium alloy, which contains approximately 50% to 55.6% nickel. In a preferred body heat transition embodiment, the nitinol can be heat treated to set the transition temperature at about 28 to 32 degrees centigrade. Shape setting of the nitinol material into its activated configuration involves heating the final nitinol structure when constrained about a mandrel or fixture that forces the nitinol structure into its substantially non-straight final shape, such as a coil, etc. The heating can be performed at temperatures ranging from about 480 degrees centigrade to 550 degrees centigrade with a preferred temperature range of about 500 to 525 degrees centigrade. The heating time can range from about 3 minutes to about 15 minutes or longer, although increased heating time tends to increase the austenite finish transition temperature (Af).

Figure 14B:
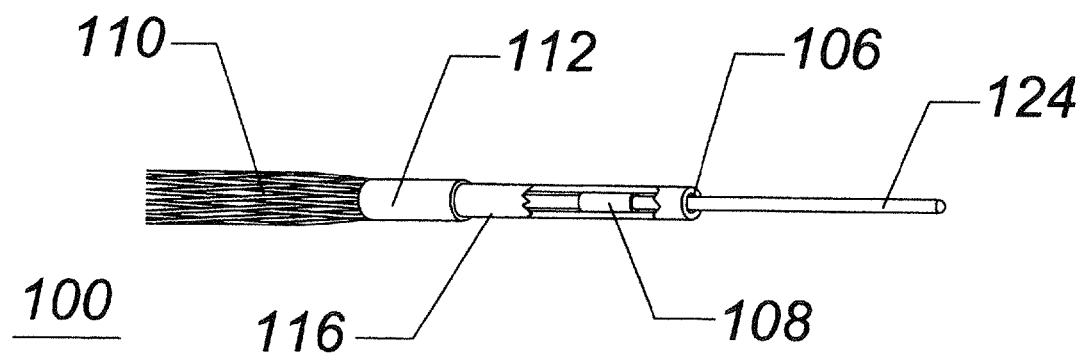
FIG. 14B illustrates a detail of the distal region of the catheter of FIG. 13A, wherein a guidewire has been inserted through the guidewire constriction forcing the expandable element to contract radially, according to an embodiment of the invention.

FIG. 14B illustrates a detailed image of the distal end of the microcatheter 100, with the expandable member 110 in its diametrically compressed, longitudinally expanded state. The microcatheter 100 further comprises the distal bond 112, the distal shaft 116 further comprising the inner lumen 106, the distal constriction 108, and the guidewire 124.

Referring to FIG. 14B, the guidewire 124 is inserted through the constriction 108, the frictional interference of which forces the distal shaft 116 to move distally to the extent possible and stretching the expandable member 110 to the extent possible. The distal shaft 116 is shown in partial breakaway view to reveal the distal constriction 108. The individual fibers of the expandable member 110 can be seen in their longitudinally expanded configuration with the fibers being oriented more axially or longitudinally than in FIG. 14A.

FIG. 15A illustrates a length of blood vessel 302 comprising a lumen 304 and a wall 306. A microcatheter 100 has been inserted into the lumen 304 and is being advanced toward a thrombus or thrombotic mass 308, which is the target of the procedure. The microcatheter 100 comprises the outer shaft 102, the expandable region 110, the distal shaft 116, the inner shaft lumen 106, the distal constriction 108, and the guidewire 124. The microcatheter 100 can be advanced through a guide catheter (not shown), which serves as a tracking device to maneuver the microcatheter 100 toward the therapeutic or diagnostic target 308.

FIG. 15B illustrates the blood vessel 302 wherein the microcatheter 100 has been advanced through the target thrombus 308 and the thrombus 308 is positioned over the expandable region 110. The microcatheter 100 further comprises the outer shaft 102, the distal shaft 116, the inner shaft lumen 106, and the guidewire 124. The blood vessel 302 is shown in partial breakaway view.

FIG. 15C illustrates the blood vessel 302 wherein the expandable region 110 has been dilated to its maximum diameter within the thrombus 308. Referring to FIGS. 3B and 3C, the diametric expansion of the expandable region 110 was performed by removing the guidewire 124 from the microcatheter 100. The expandable region 110, a spring biased mesh, has self-expanded. Additional expansion could be generated by not fully withdrawing the guidewire 124 but applying proximal force on the distal shaft 116 by friction coupling between the guidewire 124 and the distal constriction 108 of FIG. 15A.

FIG. 16A illustrates the blood vessel 302 with the microcatheter 100 advanced within the thrombotic mass 308 and the expandable region 110 having been re-collapsed by re-insertion of the guidewire 124 through the distal constriction 108. A guide catheter 402 has been advanced distally over the outer shaft 102. The guide catheter 402 further comprises a distal, adjustable flaring region 404, which is affixed to the distal end of the tubing of the guide catheter 402.

FIG. 16B illustrates the blood vessel 302 with the microcatheter 100, further comprising the outer shaft 102 and the expandable region 110, being withdrawn proximally and taking with it the thrombotic mass 308, which has become entwined within the expandable region 110. The adjustable flaring region 404 has been expanded at its distal end to coerce, at least partially, the thrombus 308 and the expandable region 110 inside the guide catheter 402. The guidewire 124 remains in place within the distal shaft 116 to maintain the stretched configuration of the expandable region 110. Once inside the guide catheter 402, the thrombus 308 can be constrained and remnants thereof can be prevented from flaking off and flowing back through the vasculature when the guide catheter 402 and the microcatheter 100 are being removed from the vasculature.

Referring to FIG. 16B, the construction of the guide catheter 402 can be the same as, or similar to, that of the microcatheter 100. The distal flaring region 404 can comprise radially expandable elements that can be activated using shape-memory properties. The shape-memory properties can be activated using body temperature or Ohmic heating to temperatures above that of body temperature. Upon removal of the higher temperatures, in the case of the Ohmic, or resistive, heating embodiments, the distal flaring region 404 can be made to assume a martensitic, or soft, characteristic conducive to removal of the guide catheter 402 from the vasculature 302. Such elevated temperatures can be generated by electrical current applied across electrical leads that run from the proximal end of the guide catheter 402 to the distal end where they are connected to each end of a nitinol expandable structure or to high-resistance wires such as those fabricated from nickel-chromium metal. The high-resistance wires can be formed along, around, or through the nitinol structure to provide optimum heat transfer to the nitinol. The electrical energy can be applied at the proximal end of the guide catheter 402 by the operator using batteries, or other electrical power supply.

Figure 17:
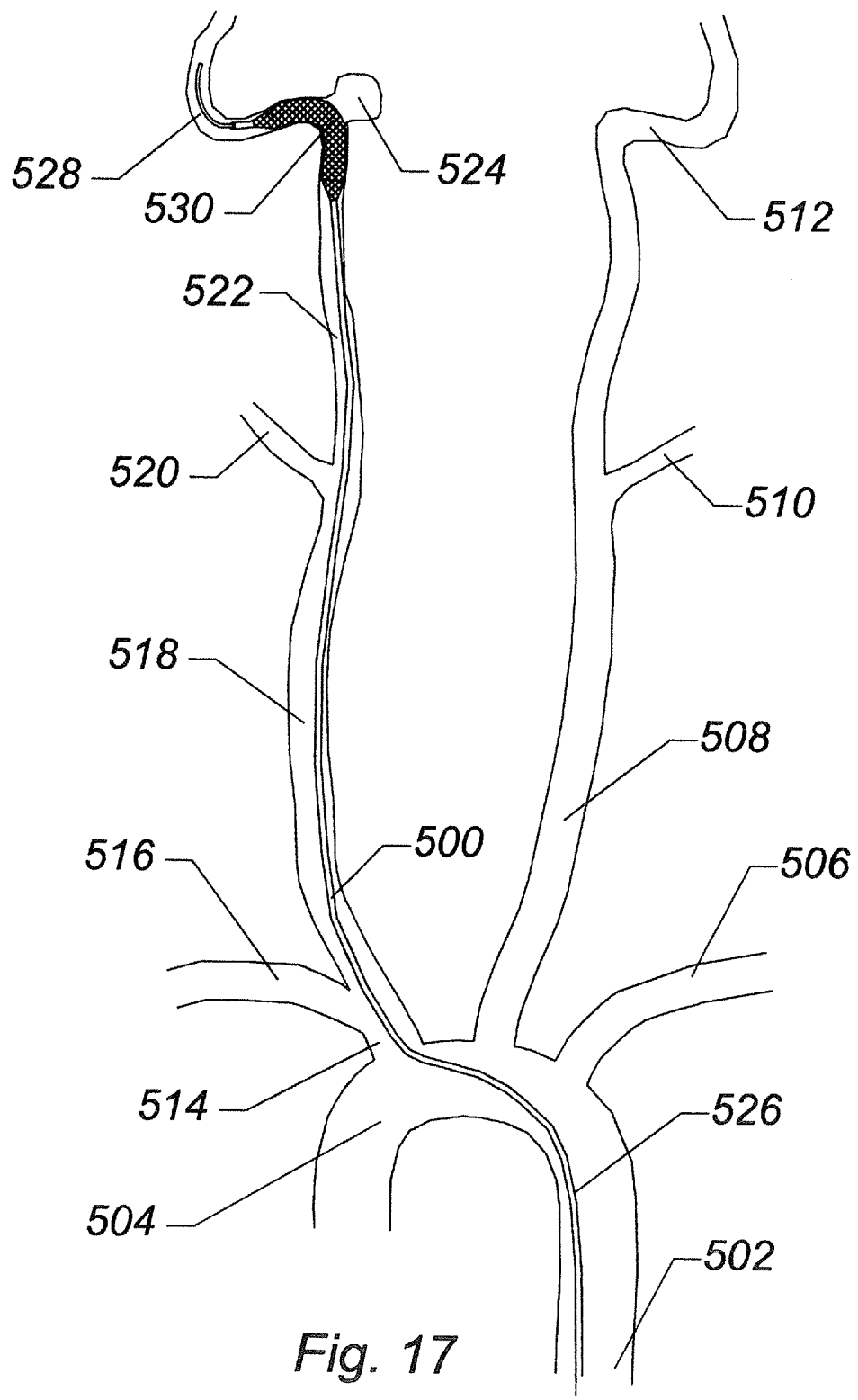
FIG. 17 illustrates an expandable catheter expanded across a cerebrovascular aneurysm for the purpose of forming a temporary neck bridge, according to an embodiment of the invention, according to an embodiment of the invention.

FIG. 17 illustrates a cranial portion of a human circulatory system comprising a descending aorta 502, an aortic arch 504, a left subclavian artery 506, a right subclavian artery 516, an innominate artery 514, a left common carotid artery 508, a right common carotid artery 518, a left external carotid artery 510, a right external carotid artery 520, a left internal carotid artery 512, a right internal carotid artery 522, a cerebrovascular aneurysm 524, a temporary neck bridge microcatheter 500, further comprising a catheter shaft 526, an expandable neck bridge region 530, and a guidewire 528.

Referring to FIG. 17, the microcatheter 500 has been routed from a femoral percutaneous insertion site (not shown) through the femoral and iliac arteries (not shown), and into the aorta 502, where it is next advanced through the innominate artery 514 and into the common carotid artery 518 and finally through the internal carotid artery 522 past the aneurysm 524 target site. The microcatheter 500 can have been routed through a guide catheter (not shown), placed during an earlier step in the procedure. The primary purpose of the guidewire 528 is to control the expansion and contraction of the neck bridge expandable region 530, although it could also be used to assist with guiding the microcatheter 500 to the target site. With the guide wire 528 removed, a separate embolic material delivery catheter (not shown) can be advanced through the guidewire lumen of the microcatheter 100 and be directed through the expandable neck bridge 530 into the aneurysm 524.

Figure 18:
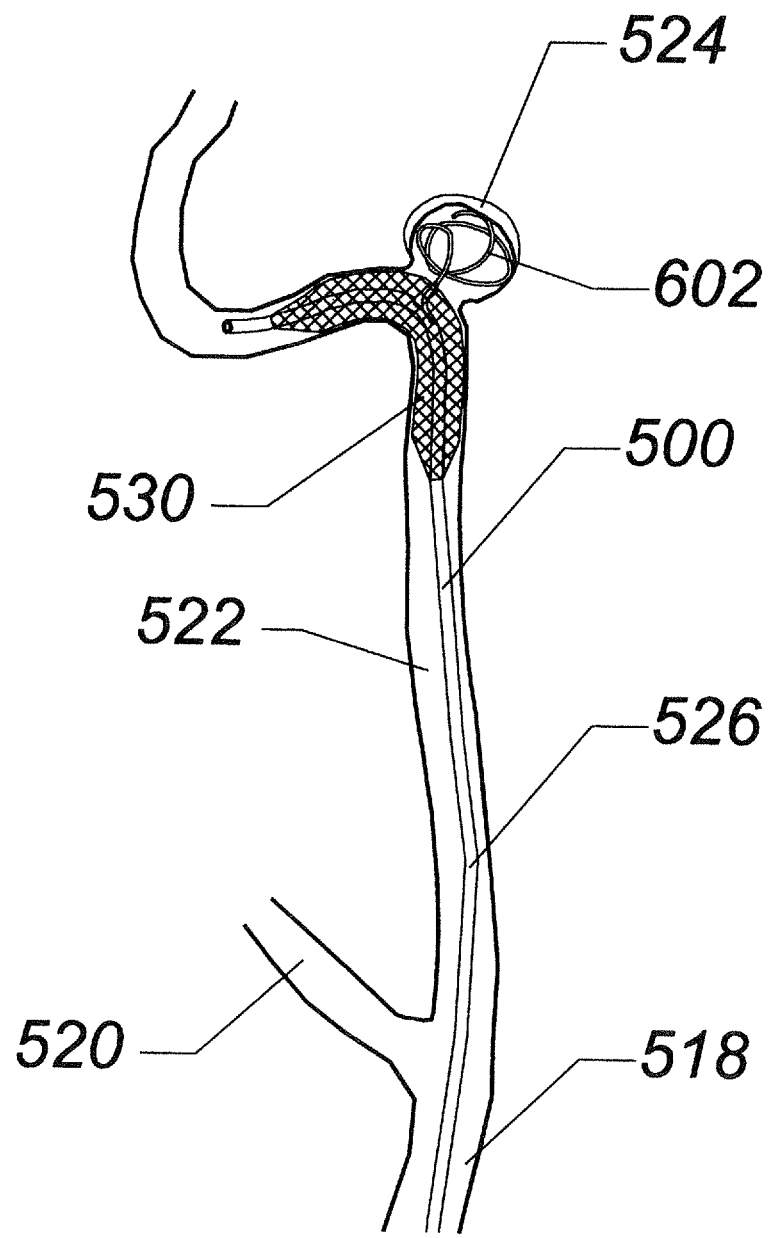
FIG. 18 illustrates an expandable microcatheter element placed across the entrance to a cerebrovascular aneurysm, wherein the expandable element forms a neck bridge across the opening to the main artery, with an embolic coil being deployed within the aneurysm, according to an embodiment of the invention.

FIG. 18 illustrates a portion of the left human carotid artery tree comprising the common carotid artery 518, the external carotid artery 520, the internal carotid artery 522, and an aneurysm 524. A microcatheter 500, comprising a catheter shaft 526 and an expandable mesh 530, has been advanced toward the aneurysm 524 and a mesh 530 has been expanded across the neck of the aneurysm 524 to form a neck bridge having porosity to blood and small diameter devices. An embolic coil 602 is being deployed within the sac of the aneurysm 524 as part of an embolization procedure.

Referring to FIG. 18, the expandable mesh 530 is capable of forming a porous barrier across the neck of the aneurysm while maintaining blood flow within the parent internal carotid artery 522. The expandable mesh 530 comprises openings between the mesh elements or strands and the openings are capable of passing small catheters, pushers, delivery devices, and the like (e.g., therapeutic or diagnostic instruments) which can be directed to the aneurysm 524 for therapeutic or diagnostic purposes. The guidewire 528, illustrated in FIG. 17, has been removed and replaced with the delivery system for the embolic coil 602. The catheter shaft 526 and the expandable mesh 530 are flexible and capable of bending around tortuous anatomy as is often found in the cerebrovasculature.

Figure 19:
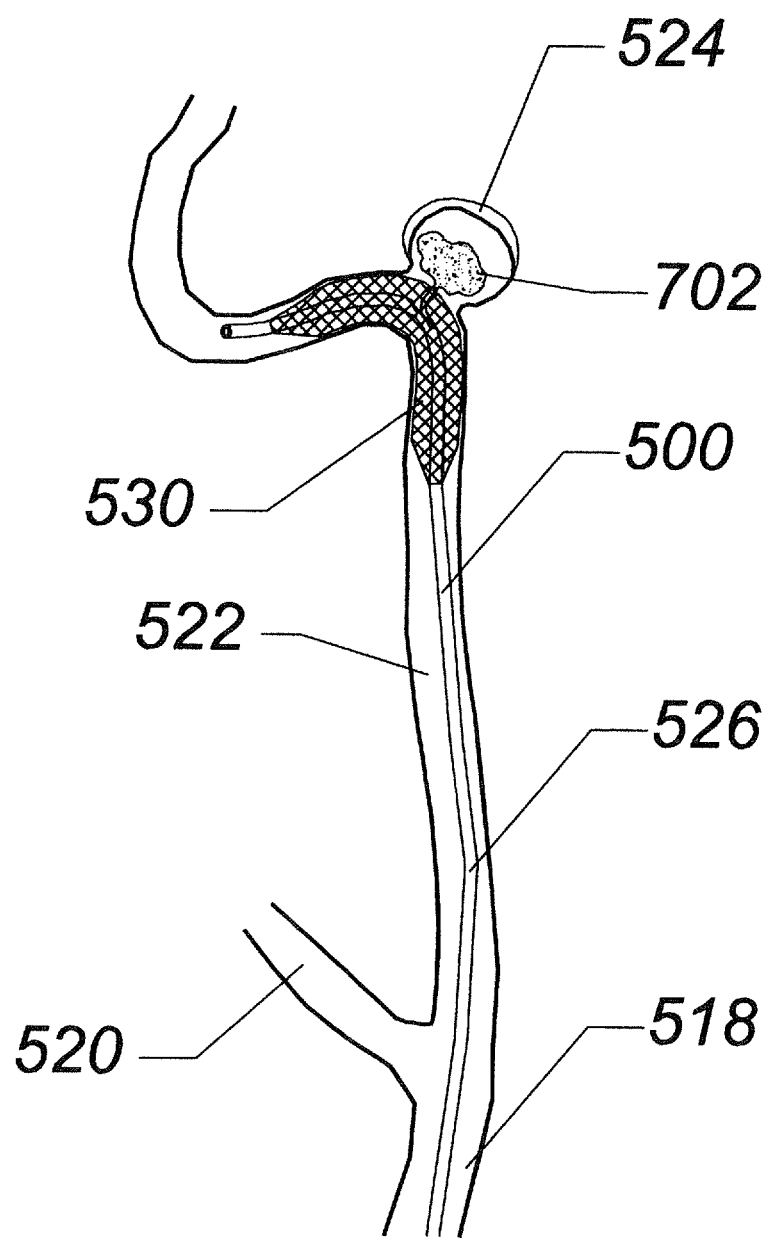
FIG. 19 illustrates an expandable microcatheter element placed across the entrance to a cerebrovascular aneurysm, wherein the expandable element forms a neck bridge across the opening to the main artery, with a quantity of embolic mass being deployed within the aneurysm, according to an embodiment of the invention.

FIG. 19 illustrates a portion of the left human carotid artery tree comprising the common carotid artery 518, the external carotid artery 520, the internal carotid artery 522, and an aneurysm 524. A microcatheter 500, comprising a catheter shaft 526 and an expandable mesh 530, has been advanced toward the aneurysm 524 and a mesh 530 has been expanded across the neck of the aneurysm 524 to form a neck bridge having porosity to blood and small diameter devices. A volume of embolic material 702 is being deployed within the sac of the aneurysm 524 as part of an embolization procedure.

Referring to FIG. 19, the embolic material 702 is being delivered through a liquid delivery catheter routed through the central lumen of the catheter shaft 526 following removal of any guidewires 528 such as those illustrated in FIG. 5. The embolic material 702 is preferably liquid or a very thin gel to permit injection through the liquid delivery catheter. The embolic material 702 can comprise polymers dissolved within solvents such as DMSO or the like, wherein upon exposure to the body environment, the DMSO or other solvent is absorbed by body tissues leaving the polymeric mass to harden into a rigid or semi-rigid embolic structure. Other embolic materials can comprise cyanoacrylate adhesives, tantalum powder, and other additives such as polymeric agents, for example. The embolic material 702 can be used alone or in conjunction with the coils 602 illustrated in FIG. 18. The catheter 500 used for this procedure, as illustrated in FIG. 17, need not be substantially different from the catheter 500 used in the procedure shown in FIG. 18.

Figure 20:
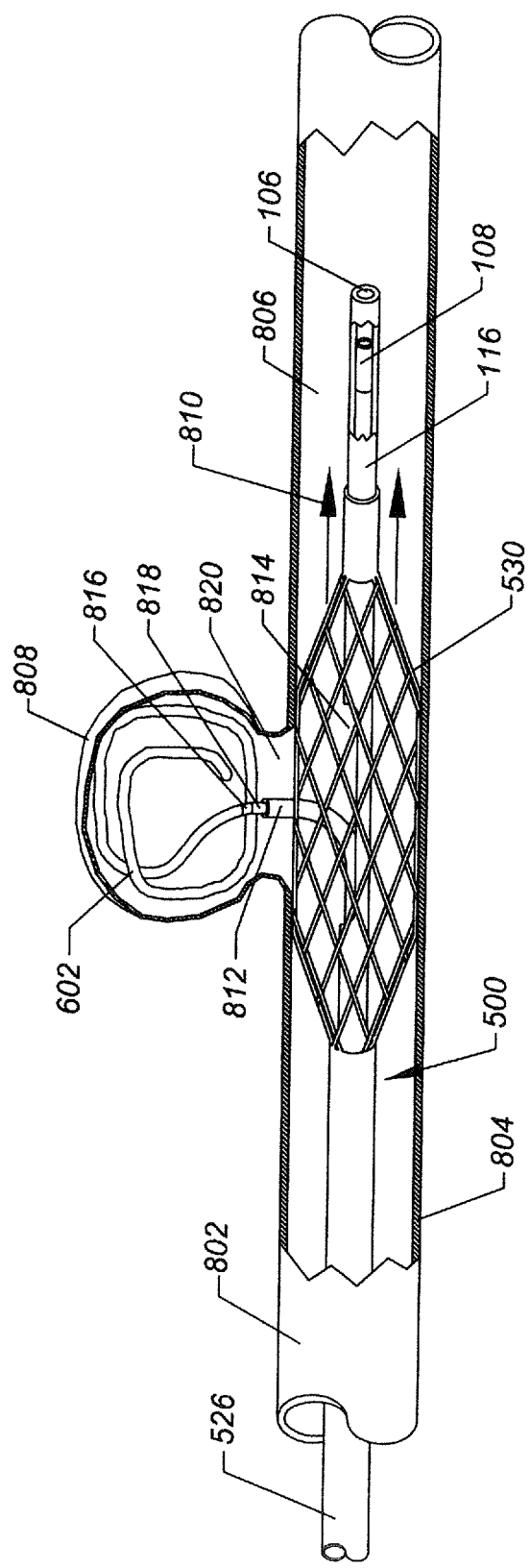
FIG. 20 illustrates the distal end of a microcatheter with an expandable region placed across the entrance to an aneurysm such that a delivery catheter is capable of deploying a coil within the aneurysm, according to an embodiment of the invention.

FIG. 20 illustrates a more detailed view of the distal end of a microcatheter 500 configured as a temporary neck bridge for an aneurysm. The microcatheter 500 comprises the mesh 530, the primary shaft 526, the secondary, or distal, shaft 116 further comprising a lumen 106, a distal constriction 108, a side window 814, a coil delivery catheter 812, a coil pusher 818, a coupler 816, and the embolic coil 602. The microcatheter 500 is illustrated deployed within a blood vessel 802 further comprising a wall 804, a lumen 806, an aneurysm 808 further comprising an aneurysm neck 820, and a volume of flowing blood 810.

Referring to FIG. 20, the guidewire 528 of FIG. 17 is not illustrated because it is removed to create room for the coil delivery catheter 812 and because its withdrawal from the distal constriction 108 permits recovery of the mesh 530 to its fully expanded configuration. The coil delivery catheter 812, or pusher, can further comprise a releasable coupler 816 at its distal end that controllably and reversibly joins the embolic coil 602 to the coil delivery catheter 812. The coil delivery catheter 812 is configured with a distal arc, or bend, so that upon exposure to the side window 814, the catheter 812 curves out of the window toward the aneurysm into which it can now be advanced. The catheter 812 is smaller in diameter than the openings in the mesh 530 to permit passage through the mesh filaments. The coil delivery catheter 812 can be a guide for a pusher 818, as illustrated, or it can, itself, be the coil pusher 818. The coupler 816 can operate due to erosion of a fusible link, release of a mechanical interlock, release of a friction bond, electrolytic detachment, or the like.

The application of the microcatheter 500 as a porous neck bridge permits partial closure of the neck 820 of the aneurysm 808, thus reducing flow washout effects that could dislodge embolic material. The expandable mesh 530 is porous and permits blood to flow through the mesh 530 following diametric expansion, thus maintaining distal perfusion. This is a superior technique to the prior art that involves total blockage of the neck 820 of the aneurysm 808 and parent vessel lumen 806 with a balloon during embolic material delivery. Such prior art total blockage can last for periods of time in excess of those tolerable to cerebral tissues. Eliminating cerebral tissue ischemia facilitates better patient outcomes following procedures where placement of a temporary neck bridge across an aneurysm 808 is indicated. Increasing the time of temporary neck bridge placement eases the burden on the interventional neuroradiologist and permits more accurate therapeutic procedures with superior patient outcomes. The microcatheter 500 can be configured to reach into the vasculature as far as the carotid siphon with an outside diameter of around 2 to 4 French. The microcatheter can be configured to reach into the cerebrovasculature as far as the Circle of Willis and beyond into the middle cerebral artery as far as the M1 bifurcation with a diameter of 1 to 3 French. The size of corresponding catheter components can be scaled appropriately to the catheter outside diameter.

Figure 21:
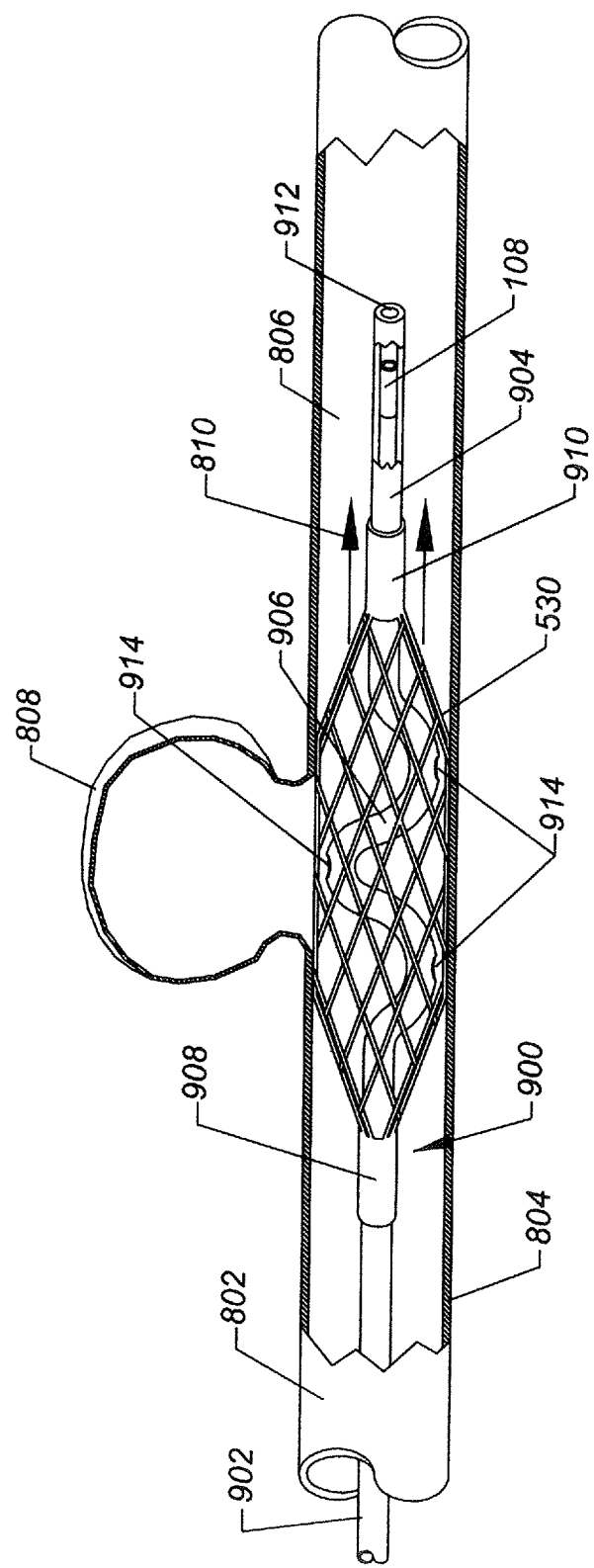
FIG. 21 illustrates the distal end of a microcatheter with its expandable region dilated within a length of cerebrovasculature, wherein the catheter comprises a serpentine expandable length section within the expandable region, according to an embodiment of the invention.

FIG. 21 illustrates an embodiment of the microcatheter 900 comprising a proximal shaft 902, a distal shaft 904, a serpentine adjustable length shaft 906, and an expandable region 530. The serpentine adjustable length shaft 906 further comprises a plurality of fenestrations ports, or holes 914. The distal shaft 904 further comprises a central lumen 912 and a constriction 108. The expandable region 530 further comprises a proximal bond 908 and a distal bond 910. The microcatheter 900 is illustrated being advanced inside a blood vessel 802 comprising a wall 804, a lumen 806, an aneurysm 808, and a volume of flowing blood 810 within the lumen 806.

Referring to FIG. 21, the expandable region 530 is being used as a temporary neck bridge to create a porous barrier across the neck of the aneurysm 808. The expandable region 530 is bonded to the proximal shaft 902 by the proximal bond 908 and to the distal shaft 904 by the distal bond 901. The serpentine adjustable length shaft 906 is bonded, welded, integral to, or otherwise affixed to the proximal shaft 902 and the distal shaft 904. The constriction 108 is affixed to the walls of the interior lumen 912 of the distal shaft 904. The holes 914 are integral to the wall of the serpentine adjustable length shaft 906. The holes 914 operably connect the interior lumen (not shown) of the serpentine adjustable length shaft 906 to the exterior environment around the outside of the shaft 906, the environment being substantially within the volume encompassed by the expandable region 530.

The expandable region 530 can comprise a mesh, as illustrated, or it can comprise a plurality of longitudinal bars or struts spaced circumferentially around the axis of the microcatheter 900. The expandable region 530 can, in other embodiments, comprise mesh structures at the proximal end, distal end, or both, and interconnecting longitudinal struts between the mesh proximal and distal ends. The serpentine adjustable length shaft 906 can comprise polymeric materials or polymeric layered construction with a central reinforcement. The polymeric materials used in the serpentine adjustable length shaft 906 can, in some embodiments, comprise elastomeric materials to permit the shaft 906 to assume a bias toward a pre-set configuration. The pre-set configuration can comprise a coil configuration or an undulating or wavy configuration. The pre-set configuration can be fabricated by methodologies such as heat-setting, casting the tube over a spiral mandrel, etc. The shaft 906 is configured such that it can straighten out either by having its ends be placed in tension, as with a guidewire pushing on the constriction 108, by a substantially straight catheter (not shown) being inserted therethrough, or both. In a preferred embodiment, the expandable region 530 is in its radially collapsed configuration when the serpentine shaft 906 is in its straightened configuration.

The holes 914 can be used for infusion of thrombolytic agents such as, but not limited to, urokinase, streptokinase, tissue plasminogen activator (tPA), or the like. In other embodiments, the holes 914 can also be used to infuse thrombogenic or embolic materials into an aneurysm 808 or for infusion of dye contrast agents for radiographic purposes.

FIG. 22A illustrates a microcatheter 100 being advanced, over a guidewire 124, toward a partially occluding thrombus 1010 adherent to the interior wall 306 of the blood vessel 302. The thrombus 1010 partially occludes the lumen 304 causing stenosis of the blood flow 810. The microcatheter 100 further comprises the proximal shaft 102, the distal shaft 116, the constriction 108, the lumen 106 of the distal shaft 116, and the expandable region 110.

Referring still to FIG. 22A, the expandable region 110 is collapsed to approximately its minimum lateral profile by the distal force exerted by the guidewire 124 against the constriction 108. The microcatheter 100 is being advanced, in some embodiments, using fluoroscopic monitoring and guidance with the aid of radiopaque markers strategically affixed to the microcatheter 100.

FIG. 22B illustrates the microcatheter 100 having been advanced through the thrombus region 1010 with the radially collapsed expandable region 110 placed approximately across the thrombus region 1010. The guidewire 124 is illustrated still in place within the microcatheter 100 to prevent diametric expansion of the expandable region 110.

FIG. 22C illustrates the microcatheter 100 with its expandable region 110 having been expanded by removal of the guidewire 124 (refer to FIG. 22B). The microcatheter 100 further comprises the proximal shaft 102, the distal shaft 116 further comprising the lumen 106 and the plurality of side holes 1002, and the constriction 108 being free from force since the guidewire is removed. The vessel 302 continues to support blood flow 810 within its lumen since the expandable region is porous to the flow of blood, due to the large fenestrations between the mesh elements. The thrombus 1010 is expanded radially outward to provide a central flow region within the vessel 302 that is free from clinically relevant obstruction. In some embodiments, holes or openings 1002 in the wall of the distal shaft 116, disposed beneath the expandable region 110, can be used for the infusion of thrombolytic agents described in FIG. 21. During infusion of the thrombolytic agents, a distal plug (not shown), located near the constriction 108 can prevent escape of the thrombolytic agents out the distal end of the lumen 106. In another embodiment, the guidewire 124 can be configured with a diameter small enough to permit annular flow thereby, but plug or close the hole in the constriction 108 to prevent substantial loss of agent through the distal end. The embodiments described herein are especially suited to rapid treatment of occlusive or ischemic stroke.

FIG. 23A illustrates a microcatheter 1100 being advanced toward an aneurysm 808 in a vessel 802. The vessel 802 further comprises a vessel wall 804, a vessel lumen 806, and a volume of flowing blood 810. The microcatheter 1100 further comprises a proximal shaft 1102, a distal shaft 1108, an expandable region 1104, and a guidewire 1110, which is shown inserted through the central lumen and which maintains the diametrically collapsed configuration of the expandable region 1104. An embolic coil 1112 is illustrated partially lodged within the aneurysm 808 with the proximal section 1114 of the coil 1112 having escaped into the lumen 806 of the parent vessel 802. The expandable region 1104 is illustrated in its diametrically collapsed configuration. In the illustrated embodiment, the expandable region 1104 is a mesh structure. The proximal tail or section 1114 could generate thrombus, thromboemboli, or itself become fully dislodged and float downstream to embolize the lumen 806 of the parent vessel 802.

FIG. 23B illustrates the microcatheter 1100 with its expandable region 1104 having been fully expanded radially in response to removal of the guidewire 1110. The microcatheter 1100 comprises the proximal shaft 1102, the distal shaft 1108, the expandable region 1104, which is a mesh in the illustrated embodiment, and a coil length adjusting region 1106. The vessel 802 comprises the wall 804, the lumen 806, the aneurysm 808, and the volume of flowing blood 810. The proximal tail 1114 of the embolic coil 1112 continues to protrude into the lumen 806.

FIG. 23C illustrates the microcatheter 1110 with a snare 1118 inserted through the central lumen of the microcatheter 1110. A guide catheter 1120 has been advanced over the proximal shaft 1102, the guide catheter 1120 further comprising a controllably, or selectively, flared distal end 1122. The snare 1118 has hooked the proximal tail 1114 of the coil 1112 in preparation for proximal retraction into the flared guide catheter 1120 and ultimate removal of the coil 1112 from the lumen 806 of the parent vessel 802.

Referring to FIG. 23C, the flared distal end 1122 is affixed to the distal end of the guide catheter 1120. The flared distal end 1122 can be an expandable structure configured with a braid or plurality of longitudinal, bendable elements, and a pull-wire (not shown) which can be used to axially contract the braid, resulting in radial expansion. Alternatively, in other embodiments, the flared distal end 1122 can comprise nitinol shape-memory elements that expand in response to applied electrical current and subsequent resistive heating, or it can expand in response to exposure to blood at body temperature. In yet another embodiment, the flared distal end 1122 can be made to expand in response to removal of a sheath, shroud, or jacket restraint.

Figure 24A:
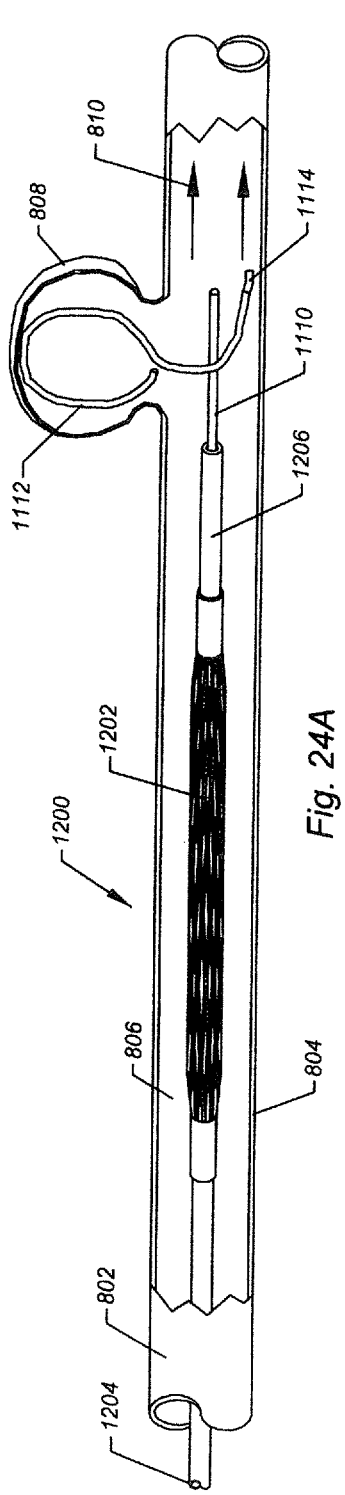
FIG. 24A illustrates a microcatheter being advanced toward an embolic coil which has become partially dislodged from an aneurysm, according to an embodiment of the invention.

FIG. 24A illustrates a microcatheter 1200 being advanced toward a partially dislodged tail or end 1114 of an embolic coil 1112. The coil 1112 is placed in an aneurysm 808 in the wall 804 of a parent vessel 802, further comprising a lumen 806 and filled with a volume of flowing blood 810. The microcatheter 1200 comprises a proximal shaft 1204, a distal shaft 1206, an expandable region 1202, and a guidewire 1110.

Figure 24B:
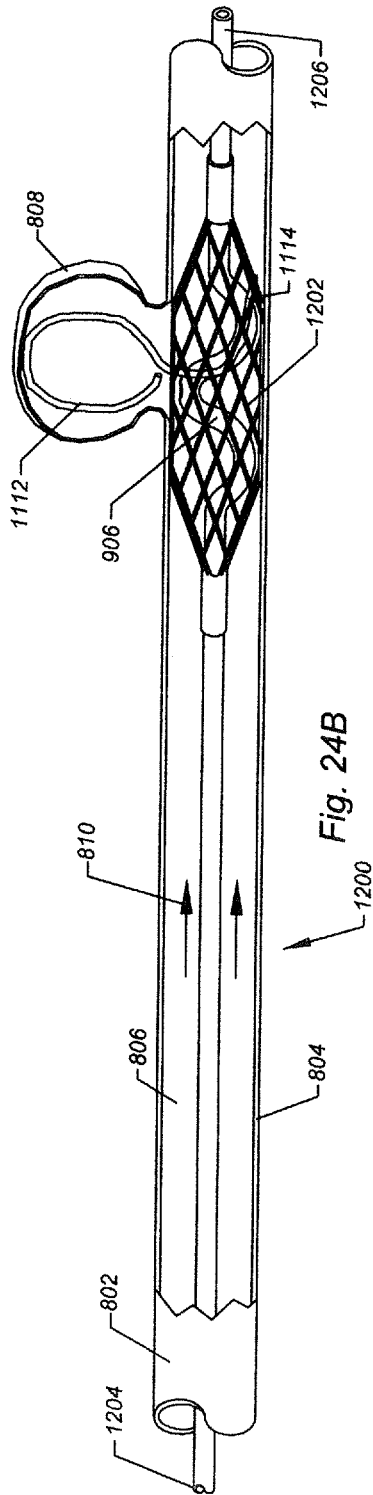
FIG. 24B illustrates an expandable member of the microcatheter dilated adjacent to the aneurysm such that the dislodged end of the coil has become entrapped within the mesh of the expandable member, according to an embodiment of the invention.

FIG. 24B illustrates the microcatheter 1200 with the guidewire 1110 removed and the expandable region 1202 in a diametrically expanded configuration. The tail 1114 is trapped within the expanded mesh of the expandable region 1202. In the illustrated embodiment, the expandable region 1202 is a mesh. However, the expandable region 1202 can also be configured as a plurality of longitudinal bars, a serpentine stent-like structure, a slotted tube, a wire basket, or the like. The microcatheter 1200 comprises a serpentine length-adjustable element 906 as described in the text accompanying FIG. 21.

Figure 24C:
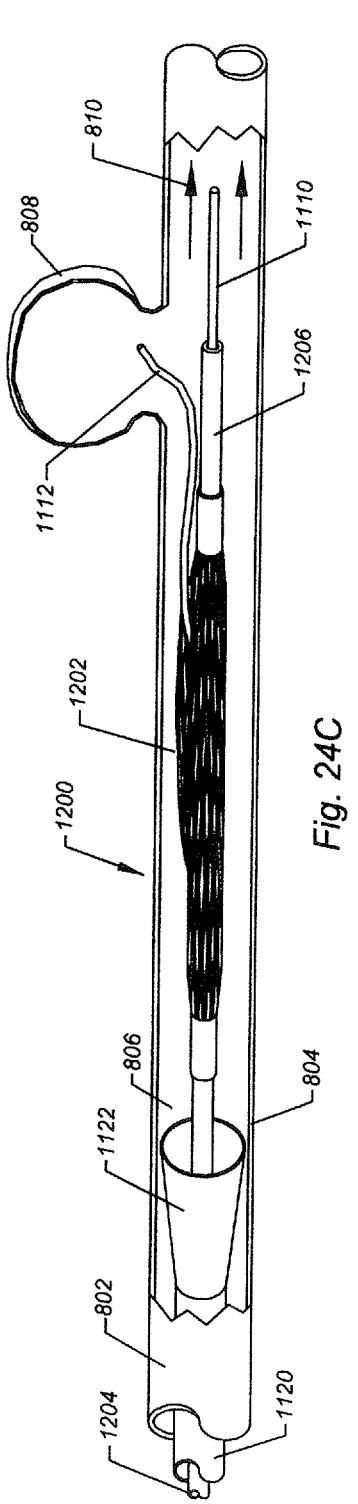
FIG. 24C illustrates the expandable member having been constricted to a reduced diametric dimension to secure the coil end within its structure, the expandable member being withdrawn proximally into a flared receiving catheter, according to an embodiment of the invention.

FIG. 24C illustrates the microcatheter 1200 with the expandable region 1202 in its diametrically collapsed or minimum profile configuration. The guidewire 810 has been inserted to straighten the length changing region 906, engaging a constriction (not shown), or both, thus forcing the axial length increase and diametric decrease in the mesh 1202. The tail 1114 of the coil 1112 is trapped within the expandable region 1202 and is in the process of being withdrawn from the aneurysm 808. A guide catheter 1120 with a flared distal end 1122 has been advanced over the proximal shaft 1120 to assist with recovery of the misplaced embolic coil 1112.

FIG. 25A illustrates a body vessel 302 with an obstruction 308 disposed therein. A microcatheter 1300 has been advanced through the obstruction 308 and an expandable member 1302 has been expanded diametrically. The microcatheter 1300 further comprises a proximal shaft 1310 and a distal expandable member cover 1304.

Referring to FIG. 25A, the expandable member 1302 comprises a mesh, braid, plurality of longitudinal filaments, or the like. The expandable member 1302 is covered, on its exterior, by the expandable member cover 1304. The expandable member cover 1304 can be fabricated from a weave, braid, knit, or membrane, either porous or impermeable to liquids. The expandable member cover 1304 can be affixed to the interior of the expandable member 1302 or to the exterior as illustrated. The expandable member cover 1304 can be deployed inside the expandable member 1302 and be tacked to the expandable member 1302 at a few points or not at all. The points of attachment can be configured to move or slide along the bars of the expandable member 1302 or the points of attachment can be fixed. The expandable member cover 1304 can be elastomeric and biased to self-expand when the expandable member 1302 is expanded. The cover 1304 is illustrated on the distal portion of the expandable member 1302 but the cover can also be positioned on the proximal portion of the expandable member 1302. The amount of expandable member 1302 partial coverage can range from 20% to 75%. The partial expandable member cover 1304 can be beneficial for procedures such as, but not limited to, trapping debris within the expandable member 1302 or for serving as a filter or protection device.

FIG. 25B illustrates a blood vessel 302 comprising an obstruction 308. A microcatheter 1320 has been advanced through the obstruction 308. The microcatheter 1320 comprises the proximal shaft 1310, the expandable region 1302, an exterior mesh cover 1308, and an interior mesh cover 1306.

Referring to FIG. 25B, in a preferred embodiment, the expandable region 1302 would have either an exterior mesh cover 1308 or an interior mesh cover 1306. The exterior mesh cover 1308, or the interior mesh cover 1306, would preferably cover substantially the entire expandable region 1302. In the illustrated embodiment, the exterior mesh cover 1308 is disposed over only the proximal ½ of the expandable region 1302 while the interior mesh cover 1306 is disposed under only the distal ½ of the expandable region. Such a configuration is made here for clarity. Materials suitable for fabricating the interior mesh cover 1306 or the exterior mesh cover 1308 include, but are not limited to, polyurethane, thermoplastic elastomer, silicone elastomer, polyester, polyimide, polyamide, PEEK, PEN, PTFE, or the like. The microcatheter 1310 comprising the full expandable region cover 1306 or 1308 is suitable for partial or complete occlusion of a vessel during a procedure for purposes such as, but not limited to, flow reversal, stagnation generation, and the like. In yet another embodiment, the mesh coating or cover 1306 or 1307 can be disposed along the central, substantially uniform diameter part of the expandable region 1302 but not extend substantially onto the tapered end sections of the expandable region 1302. In this embodiment, blood can continue to flow through the center of the expandable region 1302 and through the tapered ends from, and into, the parent vessel 302, while the cover 1306 or 1307 can serve to completely, or partially, block the neck or entrance to an aneurysm 808 such as that illustrated in FIG. 24C. Such a device can be brought to bear quickly to prevent additional hemorrhage from a ruptured aneurysm on an emergency basis, for example. Furthermore, instrumentation can be introduced through the lumen of the microcatheter to perform therapy distal to the expandable region.

Figure 26:
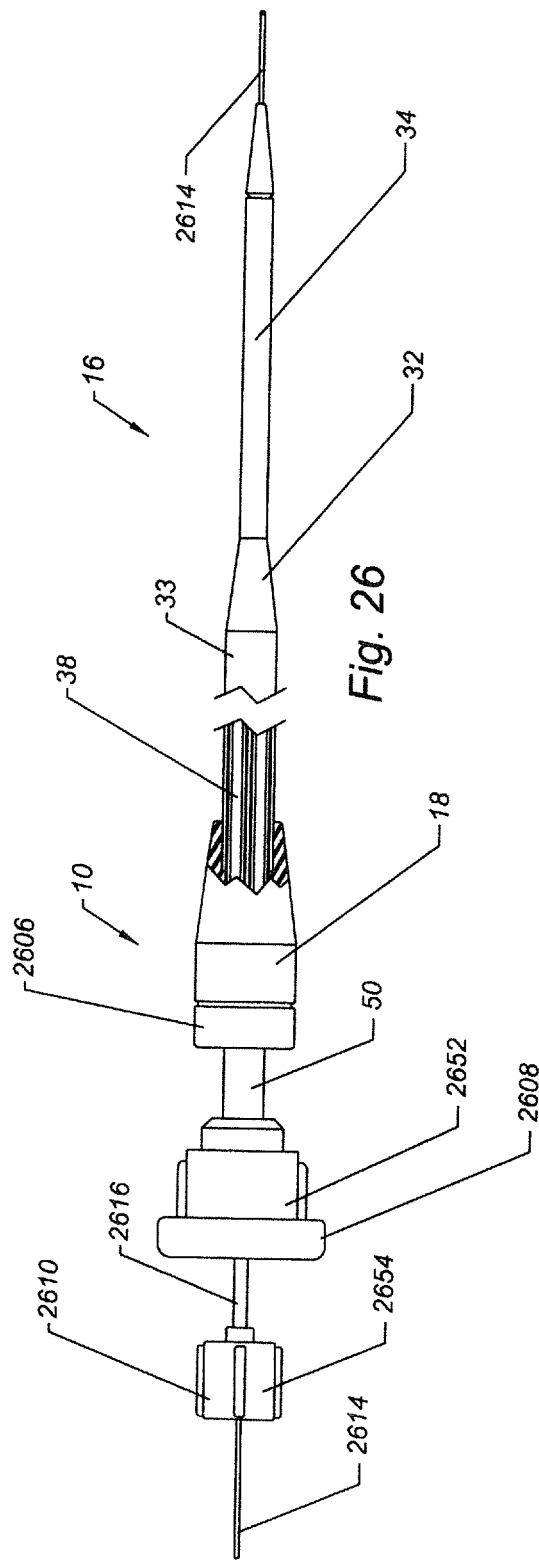
FIG. 26 illustrates a partial breakaway view of the proximal end of an expandable guide catheter, according to an embodiment of the invention.

FIG. 26 illustrates a partial breakaway, side view of an expandable guide catheter detailing the guide catheter proximal portion 2600. The proximal portion of the expandable guide catheter comprises a length of proximal tubing 2602, a slide dilator tube 2620, a length of obturator tubing 2616, a sheath hub 2650, a slide dilator hub 2652, an obturator hub 2654, and a guidewire 2614. The slide dilator hub 2652 further comprises a hemostasis valve 2608 configured to provide a fluid-tight sliding seal against the shaft of a catheter, for example the obturator tubing 2616, inserted therethrough, or to provide a fluid-tight seal with nothing inserted. The Sheath hub 2650 further comprises a hemostasis valve 2606 configured to provide a sliding seal against the slide dilator tube 2620 so as to prevent fluid loss or leakage therebetween. The obturator hub 2654 further comprises a hemostasis valve 2610 configured to seal against the guidewire 2614, or to completely close off with nothing inserted therethrough.

The proximal end of the slide dilator tube 2620 is affixed to the distal end of the slide dilator hub 2652. A central lumen extending through the slide dilator hub 2652 is operably connected to the central lumen of the slide dilator tube 2620 and to the central lumen of the hemostasis valve 2608. The proximal end of the sheath proximal tube 2602 is affixed to the distal end of the sheath hub 2650. The sheath hemostasis valve 2606 is affixed near the proximal end of the sheath hub 2650 and the central lumen of the sheath hemostasis valve 2606 is operably connected to the central lumen of the sheath hub 2650, which is also operably connected to the central lumen of the sheath proximal tube 2602. The slide dilator tube 2620 is radially restrained but can move axially within the central lumen of the sheath proximal tube 2602 under control of the user. The obturator tube 2616 is configured to slide axially but be constrained radially within the slide dilator tube 2620 central lumen, the slide dilator hub 2652 central lumen, and the slide dilator hemostasis valve 2608 central lumen, such that the obturator tube 2620 can be removed and replaced with a working catheter at a later time.

Materials suitable for fabrication of the slide dilator hub 2652, the sheath hub 2650, the obturator hub 2610, and all the hemostasis valve housings 2606, 2608, 2610 include but are not limited to, polyurethane, polyethylene, polyvinyl chloride, PEEK, polysulfone, ABS, Hytrel, polyester, and the like. The material of the hubs can be selected to match properties of any tubes affixed thereto, such that the hubs can be welded, insert-molded, ultrasonically welded, adhered using adhesive, or the like.

FIG. 27A illustrates the expandable guide catheter distal end 2700 in its first, unexpanded, radially (or diametrically) contracted or compressed state. The distal end 2700 comprises a proximal non-expandable tube 2602, an obturator tube 2616 further comprising a central lumen 2712, a transition zone 2704, an expandable outer sleeve 2706, a nose cone 2708 further comprising a proximal taper 2710 and a central lumen 2712, a translation dilator tube 2620 further comprising a central lumen 2722, and a guidewire 2714.

Referring to FIG. 27A, the nose cone 2708 is affixed to the distal end of the obturator tube 2616 and the central lumen 2712 runs all the way from the distal end of the nose cone 2708 through the proximal end of the obturator tube 2616 and any hubs affixed thereto. The translation dilator tube 2620 is slidably disposed within the lumen of the proximal tubing 2602. The distal end of the translation dilator tube 2620 is advantageously beveled or rounded on its outer edge to minimize the risk of catching on the interior aspect of the transition zone 2704 or the expandable outer sleeve 2706. In the unexpanded state, the distal end of the translation dilator tube 2620 is preferably retraced proximally to a point proximal to the proximal end of the transition zone 2704. The expandable outer sleeve 2706 can comprise a single layer or a plurality of layers. The layers of the expandable outer sleeve 2706 can be fabricated from polymeric materials. The layers of the expandable outer sleeve 2706 can be folded longitudinally to create pleats, they can be elastomeric and formed around a small mandrel with the capability of elastomeric expansion upon imposition of internal dilator pressure, or both. The layers of the expandable outer sleeve 2706 can comprise braided, woven, knitted, or other known patterns of fabric. The translation dilator tube 2620 can be fabricated from nitinol, stainless steel, titanium, PEEK, Pebax, Hytrel, polyimide, polyamide, polyester, or other suitable material. The distal end of the translation dilator tube 2620 advantageously comprises the qualities of kink resistance, flexibility, and column strength (or pushability). In an exemplary embodiment, the translation dilator tube 2620 comprises an outside diameter of approximately 3.2 French, an inside diameter of approximately 2.8 French, and a length of approximately 120-cm. The translation dilator tube can be cut, laser cut, photo-etched, electron discharge machined (EDM), or otherwise formed into a spiral cut, snake cut, or other structure with high column strength, high flexibility, and a thin wall.

FIG. 27B illustrates the expandable guide catheter distal end 2700 in its second, radially expanded state. The distal end 2700 comprises the proximal non-expandable tube 2602, the transition zone 2704, the expanded expandable outer sleeve 2706, and the translation dilator tube 2620 further comprising the central lumen 2722. The distal end 2700, in its diametrically expanded state, can comprise a substantially straight configuration, or it can comprise simple or complex curves along its longitudinal axis.

Referring to FIG. 27B, the translation dilator tube 2620 has been advanced distally such that its distal end is proximate the distal end of the expandable outer sleeve 2706. The central lumen 2722 of the translation dilator tube 2620 comprises the central lumen of the entire distal end 2700 of the guide catheter and is, in certain embodiments, the smallest lumen within the guide catheter since more proximal lumens can be at least as large in diameter, or larger. The expandable outer sleeve 2706 surrounds the translation dilator tube 2620 as a thin layer.

FIG. 28A illustrates an expandable guide catheter 2800 being advanced through a vessel 2804, further comprising a vessel lumen 2802, a volume of flowing blood 2806, and a mass of thrombus 2808. The expandable guide catheter 2800 further comprises a proximal shaft 2810, a transition zone 2812, a distal expandable length 2814, a distal nose cone 2816, a central lumen 2828, and a guidewire 2820.

Referring to FIG. 28A, the mass of thrombus 2808 has become lodged within the vessel lumen 2802. The vessel lumen 2802 is bounded by the interior of the vessel 2804. The vessel lumen 2802 contains flowing blood 2806. The mass of thrombus 2808 serves as a restriction to block the flow of blood 2806 with potentially catastrophic physiological consequences to tissues distal to the mass of thrombus 2808. The mass of thrombus 2808 can completely occlude the vessel lumen 2802 or it can partially block the vessel lumen 2802.

The proximal shaft 2810 is an axially elongate tubular structure comprising a proximal end, a distal end, and a lumen extending therethrough. The distal end of the proximal shaft 2810 is affixed, or integral, to the transition zone 2810, which is a tapered, hollow, axially elongate structure. The distal end of the transition zone 2812 is affixed, or integral, to the distal expandable length 2814, which is a hollow, axially elongate structure, further comprising a central lumen (not shown). The nose cone 2816 can be affixed to an inner shaft (not shown) slidably disposed along the inner or central lumen of the distal expandable length 2814 and capable of being removed from the expandable guide catheter 2800. The nose cone 2816 and the inner shaft (not shown) further comprise an inner lumen 2818 capable of slidably receiving the guidewire 2820.

FIG. 28B illustrates the expandable guide catheter 2800 with its distal expandable region 2814 and the transition zone 2812 enlarged to their full, maximum operating diameter within the vessel 2804, comprising the lumen 2802 and the thrombus 2808. The nose cone 2816, illustrated in FIG. 28A, has been removed by proximal retraction and is not visible. The expandable guide catheter 2800 comprises the proximal shaft 2810 and a dilator tube 2822, further comprising a central lumen 2824.

The transition zone 2812 has had its conical shape altered and is now a generally cylindrical tube having approximately constant diameter along its length. The dilator tube 2822, which was retracted proximal to the transition zone 2812 in FIG. 28A, is illustrated advanced distally so that its distal end resides generally at or near the distal end of the expandable region 2814. The inner lumen 2824 of the dilator tube 2822 describes the boundary through which catheters, debris, instruments, and other objects can pass. The dilator tube 2822 extends substantially from the distal end of the expandable region 2814 through and out the proximal end of any hubs (not shown) at the proximal end of the proximal shaft 2810. The proximal shaft 2810 can comprise constant bending and column strength or the flexibility of the proximal shaft 2810 can vary from proximal end to distal end, either in steps, continuously, or continuously variable steps. The flexibility of the proximal shaft 2810 advantageously can increase moving from the proximal end toward the distal end of the proximal shaft 2810. The flexibility of the proximal shaft 2810 can be determined entirely by the proximal shaft 2810, entirely by the dilator tube 2822, or by a combination of both. The dilator shaft or tube 2822 comprises sufficient column strength that it can be advanced and retracted axially within the proximal shaft 2810 with controllable force exerted by the user. The region between the proximal shaft 2810 and the dilator shaft 2822 as well as between the dilator shaft 2822 and the transition zone 2812 and the expandable region 2814 can comprise enhanced lubricity to facilitate smooth, relative axial movement therebetween.

The materials comprising the expandable guide catheter can include, but not limited to, PEBAX, PEEK, Hytrel, polyurethane, polyethylene, FEP, PTFE, silicone elastomer, and the like. The lubricious layer between the dilator tube 2822 and the rest of the device can comprise materials such as, but not limited to, hydrophilic materials, silicone oil, PTFE, or the like. The lubricious layer can be affixed to the dilator tube 2822, the proximal shaft 2810, the transition zone 2812, the expandable region 2814, or a combination of the aforementioned. The proximal shaft 2810 and the dilator tube 2822 can comprise monolithic materials or they can comprise composite structures with outer layers and reinforcing layers embedded therein. Such reinforcing layers can include helical metal or polymer coil windings, braided structures, longitudinal wires, spiral regions of reduced wall thickness, and the like. The transition zone 2812, the expandable distal region 2814, or both, can comprise longitudinal folds or elastomeric structures to facilitate diameter changes in response to the presence or absence of the dilator tube 2822.

FIG. 29A illustrates a microcatheter 2900 deployed through the inner lumen 2824 of the expandable guide catheter 2800. The microcatheter 2900 comprises the proximal catheter shaft 2902, an expandable mesh 2904, an expandable mesh proximal bond 2906, an expandable mesh distal bond 2908, and a length of distal tubing 2910. The guidewire 2820 is illustrated having been advanced through a central lumen of the distal tubing 2910. The expandable guide catheter 2800 comprises the proximal shaft 2810, the transition zone 2812, the expanded distal expandable length 2814, and the dilator tube or sliding dilator 2822 further comprising the central lumen 2824 and one or more vent slots 2922. The sliding dilator 2822 is slidably disposed within the lumen of the guide catheter 2800. The sliding dilator 2822 can also be configured to rotate about its longitudinal axis to present different structures toward a given circumferential position. The microcatheter 2900, the sliding dilator 2822 and the guide catheter 2800 advantageously comprise hubs (not shown) affixed to their proximal ends.

Referring to FIG. 29A, the thrombus 2808 is pierced by the microcatheter shaft 2902 and expandable mesh 2904 is positioned, in its diametrically collapsed configuration, distal to the occlusion or thrombus 2808. The expandable mesh 2904 is affixed, at its proximal end, to the microcatheter shaft 2902 by the proximal mesh bond. The expandable mesh 2904 is affixed, at its distal end, to the length of distal tubing 2910 by the distal mesh bond 2908.

The microcatheter shaft 2902 and the length of distal tubing 2910 can be fabricated from the same, or similar, materials as those used for the proximal sheath tubing 2810. The expandable mesh 2904 can be a braid or other mesh of polymeric or metal strands. Metallic materials suitable for fabrication of the expandable mesh 2904 can include but are not limited to, nitinol, stainless steel, cobalt-nickel alloys such as Elgiloy®, titanium, or the like. Polymeric materials suitable for fabrication of the expandable mesh 2904 can include polyester, co-polyester, polyamide, polyimide, and the like. The strands of the expandable mesh 2904 can comprise round, rectangular, triangular or other suitable cross-sectional shapes. A braid pattern comprising between 1 and 4 ends per strand and between 10 and 60 strands over 360 degrees can be used for the expandable mesh 2904. In an exemplary embodiment, nitinol wire ranging in diameter from about 0.002 to 0.005 inches can be used for this purpose. The nitinol can be superelastic, with a low austenite finish temperature, ranging below about 20 degrees Centigrade, in an exemplary embodiment. In other embodiments, the nitinol wire can have austenite finish temperatures above about 25 to 37 degrees Centigrade and can be configured to have shape-memory capabilities.

FIG. 29B illustrates the microcatheter 2900 of FIG. 29A with its expandable mesh 2904 having been diametrically expanded to its second, larger cross-sectional diameter that approximates that of the inside diameter of the vessel 2804. A length of catheter tubing 2916 that is disposed intermediate the proximal mesh bond 2906 and the distal mesh bond 2908 is biased toward and is illustrated having returned to a serpentine configuration that permits the proximal mesh bond 2906 and the distal mesh bond 2908 to move axially closer together resulting in an increase in the diameter of the expandable mesh 2904. The serpentine configuration of the intermediate catheter tubing 2916 can, for example, occur in a single plane up and down or sideways, etc. lateral to the longitudinal axis of the tubing 2916, it can form a spiral, or it can form other configurations. The intermediate catheter tubing 2916 is advantageously configured so that it exerts less restorative force than is exerted by a guidewire 2820 inserted therethrough, as illustrated in FIG. 29A, such that the intermediate catheter tubing 2916 configuration is governed by an inserted guidewire 2820 and forced generally straight and unbent. Removal of the guidewire 2820, as illustrated in FIG. 29B, results in the intermediate catheter tubing 2916 returning to its pre-biased serpentine configuration.

The axial shortening of the distance between the proximal and distal ends of the expandable mesh 2904 permits, creates, forces, or generates an increase in the diameter of the expandable mesh 2904, depending on whether the expandable mesh 2904 is biased to its maximum diameter, its minimum diameter, or an intermediate diameter. In an embodiment where the expandable mesh 2904 is biased to its largest diameter, the length decrease can permit the mesh to enlarge without restriction. In an embodiment where the expandable mesh 2904 is biased to its smallest diameter, the length decrease can force the mesh to enlarge, against its internal bias forces. In an embodiment where the expandable mesh 2904 is biased to an intermediate diameter, the axial length decrease can permit the mesh 2904 to enlarge somewhat and then force the expandable mesh 2904 to expand to its maximum specified diameter. It is beneficial that the diameter of the expandable mesh 2904 approximate that of the inside diameter of the vessel 2804 so that it can form a complete barrier distal to any clot or obstruction 2808. The openings in the expandable mesh 2904 are sized large enough to permit blood flow therethrough but small enough to trap or grab the occlusive material 2808.

The diameter of the expandable guide catheter 2800 is such that the inner lumen 2822 approximates that of the blood vessel lumen 2802. Vent holes 2920, numbering between 1 and 20 and sized between 0.005 and 0.050 inches in diameter, in the guide catheter proximal shaft 2810 can pass blood flow 2806 within the vessel 2804 if permitted by the obstruction 2808. Similar holes, or longitudinally oriented slots 2922, in the slide dilator 2822 can be aligned to permit blood flow therethrough or rotated out of alignment to block the flow of blood, gas, or other fluid. Blood can flow into the vent holes 2920, through the central lumen 2824 of the guide catheter 2800, and out the distal end through the annulus between the guide catheter 2800 and the microcatheter shaft 2902.

FIG. 29C illustrates the expanded microcatheter 2900 of FIG. 29B being withdrawn proximally into the expanded guide catheter 2800. Withdrawal of the microcatheter 2900 and its expanded mesh 2904 proximally causes the obstruction 2808 trapped therebetween to be coerced into the distal opening and into the lumen 2824 of the tube slide dilator 2822. Aspiration, or generation of a vacuum within the lumen 2824, can facilitate removal of the obstruction 2808 from the vessel lumen 2802. Closure of the vent holes 2920 to maintain the vacuum at the distal end of the guide catheter 2800 can be accomplished by rotating non-vented regions of the slide dilator 2822 to obstruct the vent holes 2920 in the proximal tubing 2810. The proximal end of the mesh 2904 is tapered to allow the mesh 2904 to be coerced into the lumen 2824. The obstruction 2808 and the expandable mesh 2904 can be completely withdrawn into the lumen 2824 and out the proximal end of the guide catheter 2800. Another, or the same, catheter 2900 can be reinserted into the proximal end of the guide catheter 2800 and be advanced to the target region for repeat or continued therapy or diagnosis.

Figure 30:
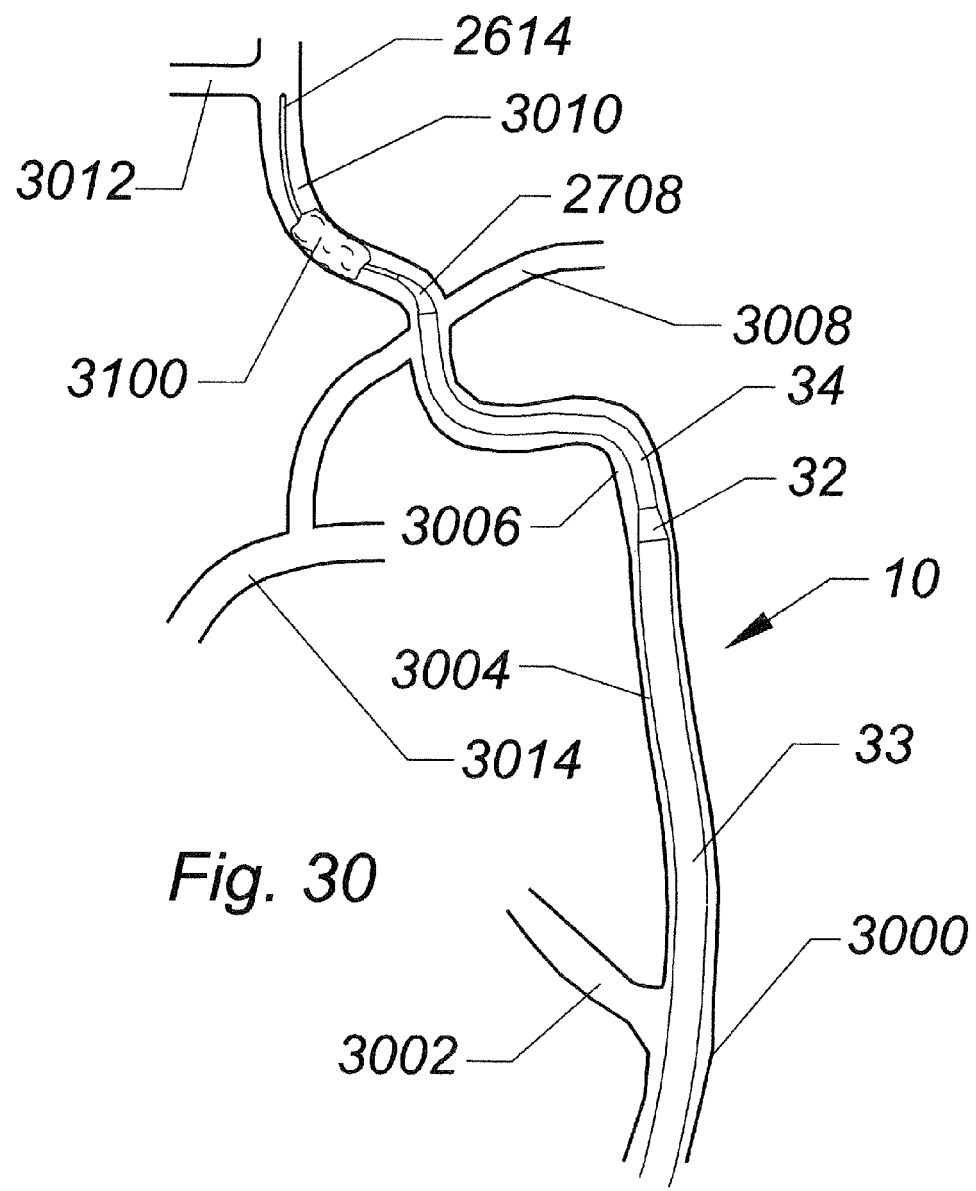
FIG. 30 illustrates a region of cerebrovasculature with an expandable guide catheter inserted with its collapsed distal region traversing a tortuous region and a guidewire extending distally thereof; according to an embodiment of the invention.

FIG. 30 illustrates a region of cerebrovasculature 3000 with an expandable guide catheter 2800 inserted therein over a guidewire 2820. The expandable guide catheter 2800 is shown comprising the proximal tubing 2810, the transition zone 2812, the distal expandable region 2814, and the nose cone 2816. The cerebrovascular anatomy 3000 comprises the internal carotid artery 3004, the external carotid artery 3002, the carotid siphon 3006, the middle cerebral artery 3008, the anterior cerebral artery 3010, the anterior communicating artery 3012, the posterior cerebral artery 3014, the posterior communicating artery 3016, and a region of thrombus 3100 located in the anterior cerebral artery 3010.

Referring to FIG. 30, the expandable guide catheter 2800 is illustrated with its distal expandable region 2814 in its diametrically collapsed, small cross-sectional distal configuration such that it comprises maximum flexibility while maintaining column strength. The expandable region 2814 is smaller in diameter than the proximal region 2810. The transition zone 2812 tapers between the diameter of the proximal region 2810 and the expandable region 2814 at an angle of between 1 and 45 degrees. The small diameter expandable region 2814 exhibits high flexibility and pushability and can, therefore, easily negotiate the tortuous carotid siphon 3006 in a way that larger catheters cannot achieve. In coordination with a J-tip guidewire 2820 or other suitably shaped guidewire having a diameter of about 0.013 inches, 0.010 inches, or smaller, the expandable guide catheter 2800 can be advanced into the circle of Willis, which is the region of the cerebrovasculature anatomically distal to the carotid siphon 3006. The proximal region 2810, which exhibits lower flexibility than the distal expandable region 2814, resides in vessels exhibiting lower tortuosity, larger diameter, or both. The nose cone 2816 is removable and serves as a tapered leading edge to help guide the guide catheter distal end 2814 into the vasculature.

Figure 31:
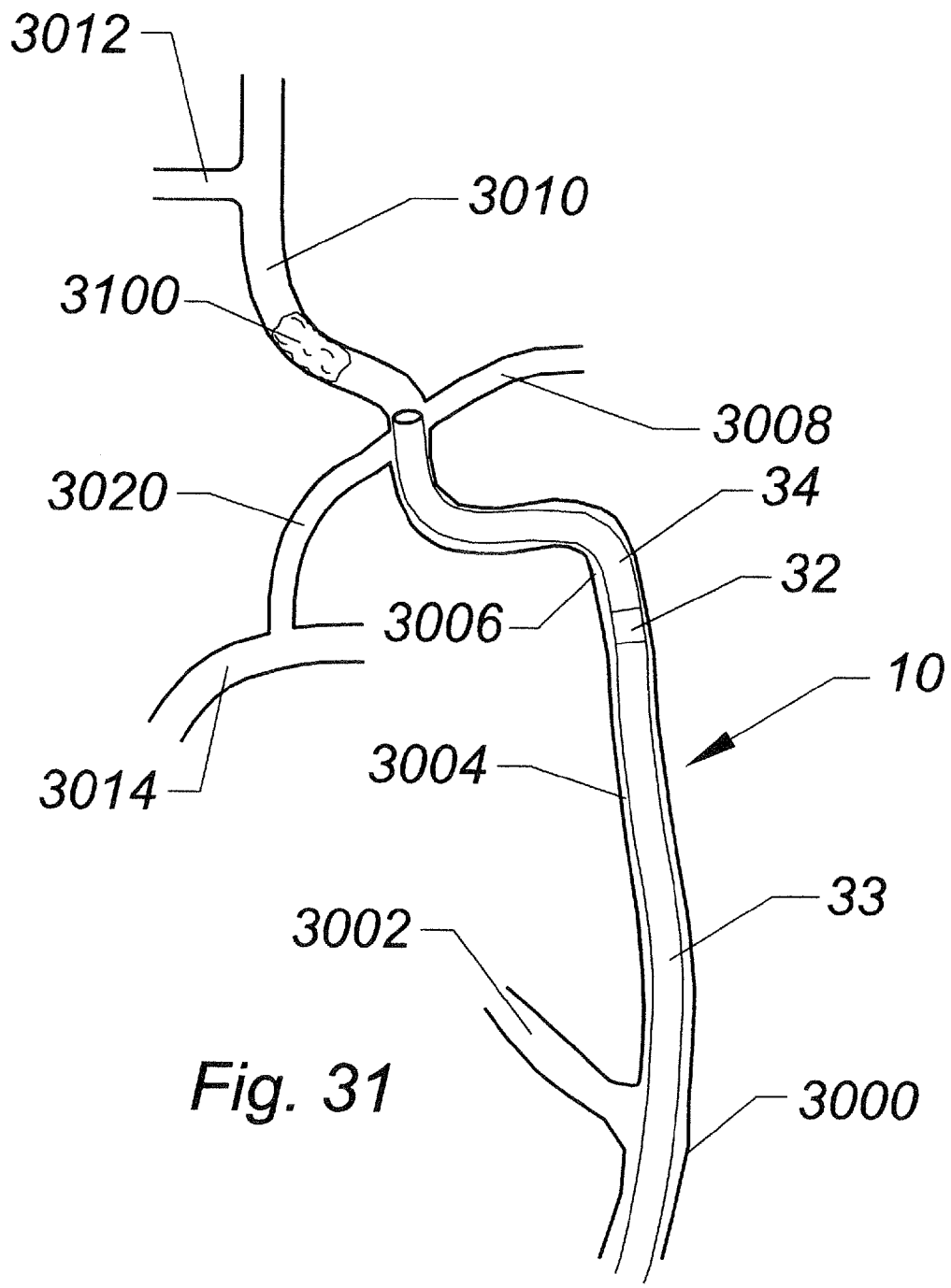
FIG. 31 illustrates the expandable guide catheter inserted into the cerebrovasculature in close proximity to an occlusive clot and its distal end diametrically expanded; according to an embodiment of the invention.

FIG. 31 illustrates the expandable guide catheter 2800 with its distal expandable region 2814 having been dilated to its full extent. The vascular anatomy 3000 comprises the internal carotid artery 3004, the carotid siphon 3006, the middle cerebral artery 3008, the anterior communicating artery 3012, the posterior cerebral artery 3014, the posterior communicating artery 3020, and the anterior cerebral artery 3010. The occlusion 3100 resides in the anterior cerebral artery 3010. The carotid siphon 3006 has straightened out and enlarged in diameter somewhat due to the presence of the expanded guide catheter distal end 2814. An occlusion 3100, which can be a mass of thrombus, a misplaced medical device, a region of atheroma, or the like, substantially occludes the lumen of the anterior cerebral artery 3010. Any guidewires are removed from the guide catheter 2800 at this time.

Figure 32:
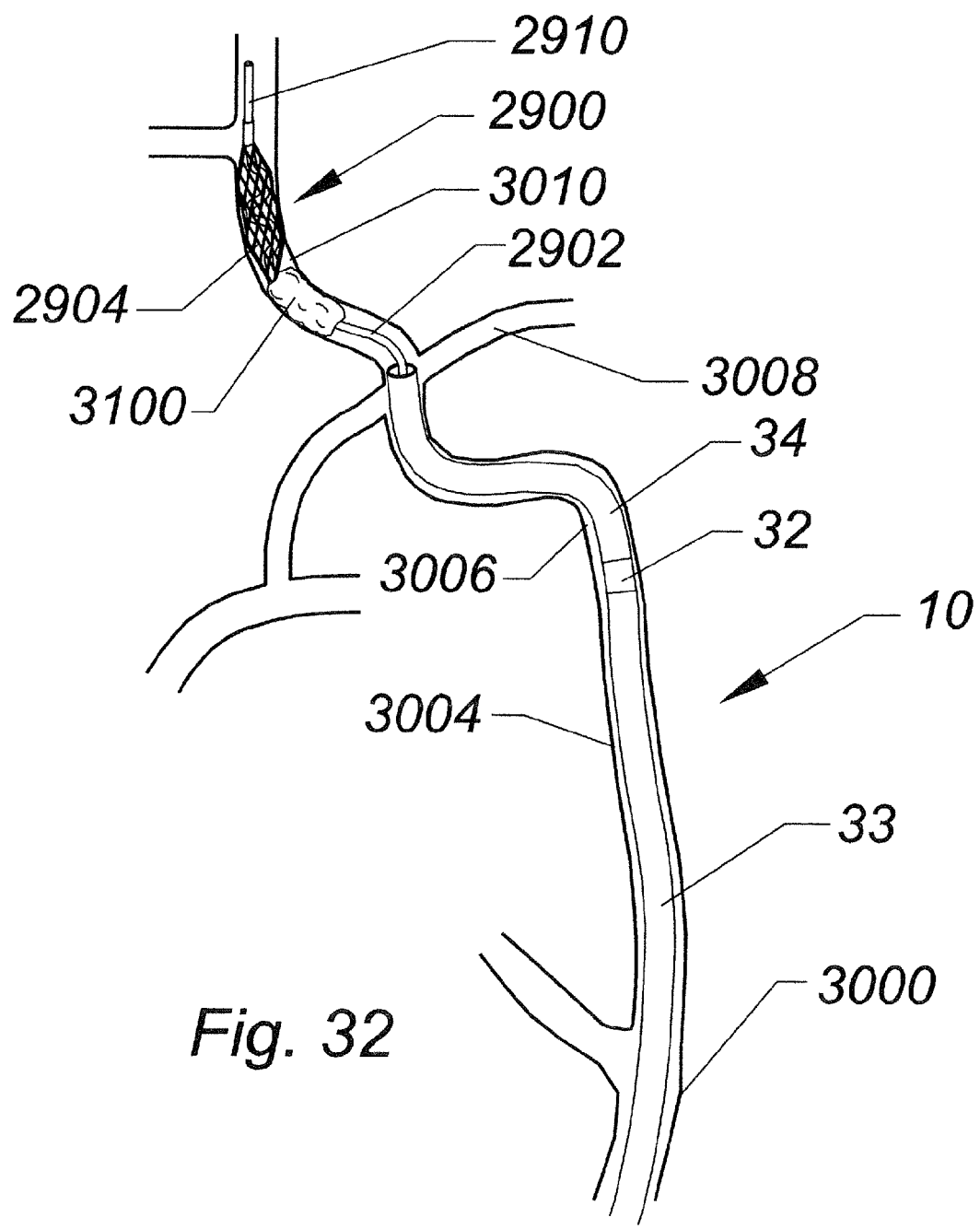
FIG. 32 illustrates the expandable guide catheter of FIG. 31 with a clot retrieving microcatheter inserted therethrough and beyond a clot prior to expansion of a distal snare element, according to an embodiment of the invention.

FIG. 32 illustrates the distal end of an expandable microcatheter 2900 inserted through the expanded guide catheter 2800, through the occlusion 3100, and with its distal end 2904 diametrically expanded. The expandable microcatheter 2900 comprises the proximal catheter shaft 2902, the expandable mesh 2904, and the distal catheter shaft 2910. The vascular anatomy 3000 comprises the internal carotid artery 3004, the carotid siphon 3006, the middle cerebral artery 3008, and the anterior cerebral artery 3010. The occlusion 3100 resides in the anterior cerebral artery 3010. The microcatheter 2900 will next be withdrawn proximally, relative to the guide catheter 2800, to retrieve the obstruction 3100. After the obstruction 3100 is removed from the vasculature 3000, the microcatheter 2900 will be removed from the guide catheter 2800. The guide catheter distal region 2814 will be collapsed diametrically by retracting the slide dilator 2822 proximally, after which the guide catheter 2800 can be removed from the vasculature.

FIG. 33A illustrates a microcatheter 2900 deployed through the inner lumen 2824 of the expandable guide catheter 2800. The microcatheter 2900 comprises the proximal catheter shaft 2902, an expandable mesh 2904, an expandable mesh proximal bond 2906, an expandable mesh distal bond 2908, and a length of distal tubing 2910. The guidewire 2820 is illustrated having been advanced through a central lumen of the distal tubing 2910. The expandable guide catheter 2800 comprises the proximal shaft 2810, the transition zone 2812, the expanded distal expandable length 2814, and the dilator tube or sliding dilator 2822 further comprising the central lumen 2824 and one or more vent slots 2922. The sliding dilator 2822 is slidably disposed within the lumen of the guide catheter 2800. The sliding dilator 2822 can also be configured to rotate about its longitudinal axis to present different structures toward a given circumferential position. The microcatheter 2900, the sliding dilator 2822 and the guide catheter 2800 advantageously comprise hubs (not shown) affixed to their proximal ends.

The microcatheter 2900 is shown advanced into and through a thrombus 2808 resident within the lumen of a body vessel 2804. Flood flow 2806 is restricted by the presence of the thrombus 2808 so tissues distal to the thrombus 2808 are at risk for ischemia. The microcatheter 2900 is placed within the thrombus 2808 so that it can be expanded for the purpose of flow restoration within the lumen of the vessel 2804.

FIG. 33B illustrates the microcatheter 2900 of FIG. 33A with its expandable mesh 2904 having been diametrically expanded to its second, larger cross-sectional diameter that approximates that of the inside diameter of the vessel 2804. A length of catheter tubing 2916 that is disposed intermediate the proximal mesh bond 2906 and the distal mesh bond 2908 is biased toward and is illustrated having returned to a serpentine configuration that permits the proximal mesh bond 2906 and the distal mesh bond 2908 to move axially closer together resulting in an increase in the diameter of the expandable mesh 2904. The serpentine configuration of the intermediate catheter tubing 2916 can, for example, occur in a single plane up and down or sideways, etc. lateral to the longitudinal axis of the tubing 2916, it can form a spiral, or it can form other configurations. The intermediate catheter tubing 2916 is advantageously configured so that it exerts less restorative force than is exerted by a guidewire 2820 inserted therethrough, as illustrated in FIG. 33A, such that the intermediate catheter tubing 2916 configuration is governed by an inserted guidewire 2820 and forced generally straight and unbent. Removal of the guidewire 2820, as illustrated in FIG. 33B, results in the intermediate catheter tubing 2916 returning to its pre-biased serpentine configuration.

Following removal of the guidewire 2820 and diametric expansion of the mesh 2904, the thrombus 2808 is compressed against the wall of the vessel 2804 thus permitting blood 2806 to flow more readily through the lumen of the vessel. Thus, in this configuration, temporary flow restoration is accomplished within the blood vessel, thus minimizing the risk of ischemia to the patient. Injection of thrombolytic agents through the microcatheter 2900 causes the thrombolytic agents to exit through the ports 914, proximate the thrombus 2808. The thrombolytic agents can dissolve or break up the thrombus 2808 to permit aspiration of the clot 2808 into the guide catheter 2800.

Figure 34A:
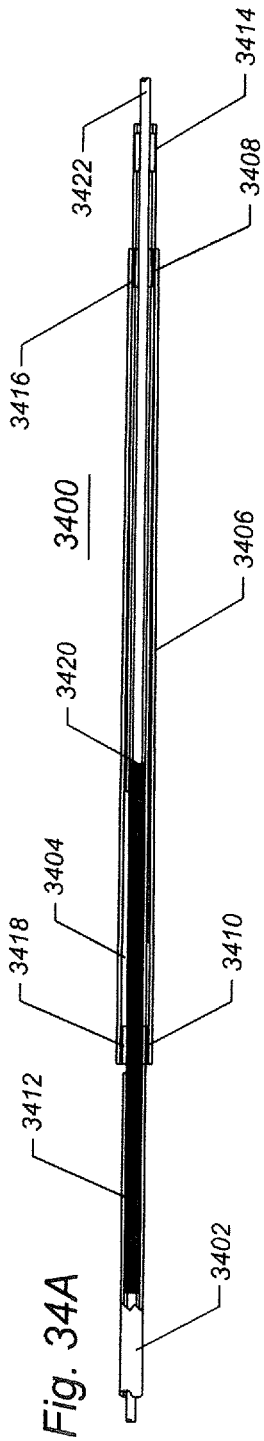
FIG. 34A illustrates an unexpanded distal end of a thrombectomy or flow restoration catheter that is activated by distal advancement of the proximal end of an expandable mesh, according to an embodiment of the invention.

FIG. 34A Illustrates a side view of a microcatheter 3400 configured as a thrombectomy or flow restoration device. The microcatheter 3400 comprises a catheter shaft 3402 further comprising a slider window 3404, a hub (not shown), an expandable mesh 3406, a distal mesh bond 3408, a proximal mesh collar 3410, a slider 3412, a distal radiopaque marker 3414, a distal mesh radiopaque marker 3416, and a slider to collar bond 3418. The slider 3412 further comprises a central lumen 3420 and the catheter 3400 rides over a small diameter guidewire 3422 that passes through the central lumen 3420 of the slider 3412. This embodiment, as well as similar embodiments, has the advantage of exerting substantial radial forces outward to help ensnare or trap thrombus, as well as for moving the thrombus radially outward to create a permanent or temporary flow restoration channel.

Referring to FIG. 34A, the slider 3412 is affixed to the proximal mesh collar 3412 by a weld, bond, pin, fastener, or the like 3418. The slider to collar bond 3418 rides within a skive, window, fenestration, elongated hole, or the like 3404 in the catheter tubing or shaft 3402. The proximal slider to collar bond 3418 affixes the proximal end of the mesh 3406 to the collar 3410. The collar 3410 is slidably disposed over the outside of the catheter shaft 3402 and moves along the longitudinal axis of the catheter shaft 3402, but is radially constrained not to move relative to the catheter shaft 3402. The distal end of the mesh 3406 is affixed to the catheter tubing 3402 by the distal mesh bond 3408. The hub (not shown) is bonded, welded, or otherwise affixed to the proximal end of the catheter shaft 3402. The expandable mesh 3406 is fabricated from nitinol, stainless steel, cobalt nickel alloy, polyimide, polyamide, polyester, or other high strength material. The wire diameter comprising the mesh 3406 can range between about 0.0005 and 0.006 inches with a preferred range of about 0.001 to 0.004 inches. The mesh 3406 can also comprise flat wire ranging in thickness between about 0.0005 to 0.004 inches and in width between about 0.001 and 0.010 inches. In a preferred embodiment, the mesh 3406 is fabricated from superelastic nitinol that is shape set to be biased toward a cylindrical, diametrically collapsed configuration.

In an exemplary embodiment, the slider 3412 has an internal diameter of about 0.012 inches and the inside diameter of the catheter shaft 3402 is about 0.016 to 0.017 inches. The mesh 3406 can be about 1-cm to about 5-cm long depending on the use of the device. The distance between the distal mesh bond 3408 and the distal end of the catheter shaft 3402 can range from about 1-cm to about 10-cm.

The slider 3412, in an exemplary embodiment can comprise a coil of platinum, stainless steel, tantalum, gold, titanium, nitinol, or the like with an outside diameter of about 0.015 inches. The slider coil 3412, having strand diameters ranging between about 0.001 to 0.003 inches remains flexible along its length and does not detract from the flexibility of the distal end of the catheter shaft 3402. The collar to slider bond 3418 is maintained as short as possible, preferably between 0.010 and 0.100 inches to maximize flexibility in the region.

The catheter shaft 3402, in an exemplary embodiment, comprises between two and six discreet regions of flexibility with increasing flexibility moving from the proximal to the distal end of the catheter shaft 3402. The increasing flexibility can be generated by decreasing the modulus of elasticity or hardness (durometer) of the polymer used in the shaft 3402, as well as changing the stiffness of a reinforcing braid or coil encased therein.

Figure 34B:
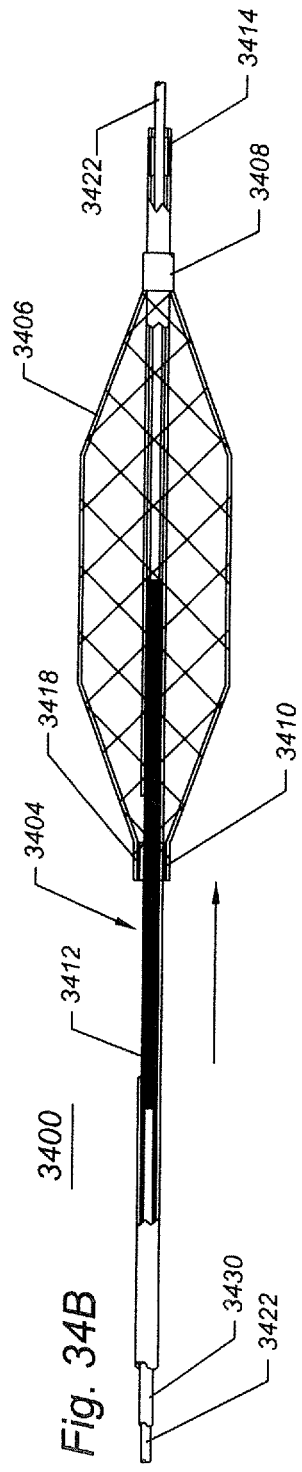
FIG. 34B illustrates an expanded distal end of a thrombectomy or flow restoration catheter having been activated by distal advance of an annular sleeve surrounding a guidewire against a feature coupled to the proximal end of the mesh, according to an embodiment of the invention.

FIG. 34B illustrates a side view of the microcatheter 3400 wherein the distal expandable mesh 3406 has been expanded by distal motion of the proximal end of the mesh 3406 relative to the fixed distal end 3408 of the mesh 3406. The distal advance of the proximal end of the mesh 3406 is generated through force applied by an annular sleeve 3430 surrounding the guidewire 3422, wherein the annular sleeve 3430 exerts a force to move the slider 3412, slidably disposed within the lumen of the catheter 3402. The slider 3412 is affixed to an external collar 3410 by the collar to slider bond 3418, which is in turn affixed to the proximal end of the mesh 3406. The collar 3410 and slider fixation element 3418 protrudes through the window 3404 in the side of the catheter tubing 3402, wherein the window 3404 completely penetrates the wall of the tubing 3402.

Referring to FIG. 34B, the annular sleeve 3430 can completely surround the guidewire 3422 or it can partially surround the guidewire 3422. The partially surrounding version of the sleeve 3430 comprises a generally "C"-shaped cross-section. The diametric clearance between the inner diameter of the sleeve 3430 and the outer diameter of the guidewire 3422 can range from about 0.0005 inches to 0.010 inches and preferably between 0.001 and 0.003 inches. The diametric clearance between the outside diameter of the sleeve 3430 and the inside diameter of the catheter tubing 3402 can range from about 0.0005 inches to about 0.010 inches with a preferred range of about 0.001 and 0.005 inches.

The annular sleeve 3430 can comprise materials such as but not limited to, polyimide, polyamide, PEEK, Hytrel, polyester, and the like. The annular sleeve 3430 can comprise a reinforcing structure such as a coil, braid, or the like.

The window 3404 is preferably about as long as the projected travel of the collar 3410 with extra allowance to accommodate for the length of the collar 3410. For example, if the collar 3401 is projected to move 0.300 inches and the length of the collar is 0.060 inches, the window 3404 is preferably at least about 0.360 inches long. The circumferential extent of the window 3404 can range from about 90 degrees to about 180 degrees.

The bond 3418 between the collar 3410 and the slider 3412 can comprise a pin, a weld, an adhesive joint, a silver solder joint, a combination thereof, or the like. In an exemplary embodiment, the collar 3410 is welded to the slider 3412 using a laser welder or a micro-tig welder. The length of the collar 3410 and the attachment joint 3418 is advantageously minimized to maintain maximum flexibility of the collar 3410 and slider 3412 assembly.

The proximal end (not shown) of the annular sleeve 3430 extends to the proximal end of the catheter hub (not shown) and beyond so that the sleeve 3430 can be manipulated by the user relative to the catheter hub (not shown). In a preferred embodiment, the proximal end of the annular sleeve 3430 comprises a knob, hub, or fitting (not shown) suitable for grasping and advance relative to the catheter hub (not shown). In another embodiment, the sleeve hub (not shown) comprises a tubular projection that slides longitudinally within the catheter hub to maintain radial positioning and prevent buckling of the sleeve-guidewire combination within the catheter hub (not shown). In yet another embodiment, the sleeve hub comprises a male Luer lock configured to releasably attach to a complimentary structure such as a female Luer lock on the catheter hub (not shown).

Figure 34C:
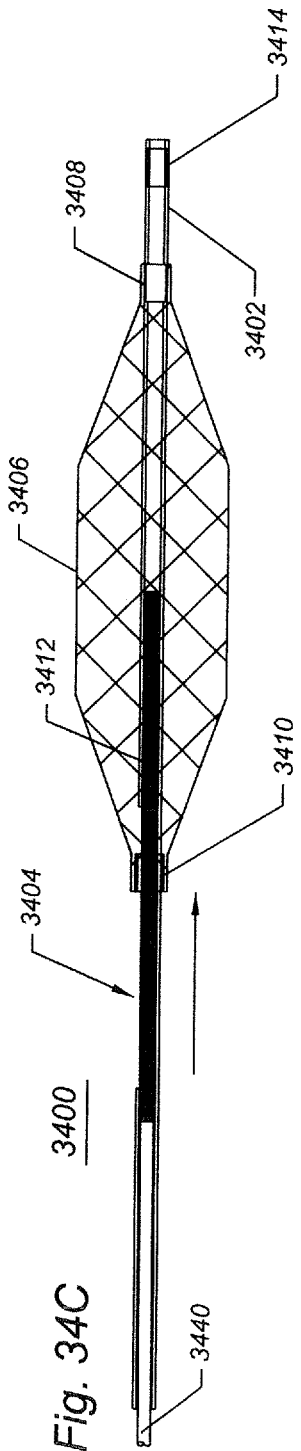
FIG. 34C illustrates an expanded distal end of a thrombectomy or flow restoration catheter having been activated by distal advance of a large guidewire against a feature coupled to the proximal end of the mesh, according to an embodiment of the invention.

FIG. 34C illustrates a side view of the microcatheter 3400 wherein the distal expandable mesh 3406 has been expanded diametrically by distal motion of the proximal end of the mesh 3406 relative to the fixed distal end 3408 of the mesh 3406. The distal advance of the collar 3410, which drives the mesh 3406 is generated by advancing an activation guidewire 3440, comprising a diameter or enlargement that is incapable of passing through the lumen of an axially elongate slider 3412 disposed within the lumen of the catheter tubing 3402.

Referring to FIG. 34C, the microcatheter 3400 comprises the catheter tube 3402, the window 3404, the distal radiopaque marker 3414, the distal mesh bond 3408, the collar 3410, the slider 3412, and the mesh 3406. The activation guidewire 3440 can be inserted following removal of the standard tracking guidewire 3422 (Refer to FIG. 34A). The tracking guidewire 3422 is small enough to fit through the central lumen or hole in the slider 3412 and allows free motion of the catheter 3400 thereover. The activation guidewire 3440 comprises features that allow it to displace the slider 3412 distally since it will not fit through the hole or lumen in the slider 3412.

FIG. 35A illustrates a proximal end of a thrombectomy or flow restoration catheter 3400 comprising a hub 3502 further comprising a female Luer lock fitting 3506, a strain relief 3504, the catheter tubing 3402.

Referring to FIG. 35A, the hub 3502 comprises a central tapered lumen that facilitates coercion of guidewires and other small catheters distally so that they are guided into the lumen of the catheter tubing 3402. The guidewire 3422 is illustrated passing through the hub 3502 and into the catheter tubing 3402. The catheter tubing 3402 is affixed within the hub 3502 using welding, insert molding, adhesive bonding, solvent bonding, or the like. A thru lumen is maintained without any steps moving from proximal to distal within the hub 3502. The strain relief 3504 comprises an elastomeric material that reduces stresses on the catheter tubing 3402 where it exits the hub 3502. The hub 3502 can comprise materials such as, but not limited to, polycarbonate, polysulfone, Grilamid®, polyurethane, ABS, and the like.

FIG. 35B illustrates a proximal end of a thrombectomy or flow restoration catheter 3400 comprising the hub 3502, the female Luer lock fitting 3506, the strain relief 3504, and the catheter tubing 3402. The catheter 3400 further comprises an activation sleeve 3430 slidably disposed over the guidewire 3422. The activation sleeve 3430 is affixed, at its proximal end, to a control cap 3510 further comprising an optional male Luer lock fitting 3512. The activation sleeve 3430 is bonded, welded, adhesive bonded, solvent bonded, insert molded, or the like to achieve the attachment to the cap 3510. A through lumen (not shown) is maintained all the way out the proximal end of the cap 3510 so that the guidewire 3422 can exit out the proximal end of the cap 3510. The cap 3510 is affixed to the sleeve 3430 in a precise location so that the user can advance the cap and tighten it to the hub 3502 without needing to worry about over-advancing the sleeve 3430 too far and thus causing damage to the slider 3412 or collar 34210

FIG. 36A illustrates a catheter hub 3600 affixed to the proximal end of the catheter shaft 3402. The catheter hub 3600 comprises a "Y" connector suitable for injection of thrombolytic material into a sidearm port 3606, which is terminated with a female Luer lock fitting 3608. The catheter hub 3600 can also comprise hemostasis valves 3622 such as, but not limited to, Tuohy-Borst valves, pinhole valves, stopcocks, slit valves, duckbill valves, a combination of these, or similar, to terminate the central port as well as the sidearm port 3606.

Referring to FIG. 36A, the catheter hub 3600 comprises a main body 3602 further comprising the slider window 3620 and the slider lumen 3616, the sidearm port 3606 further comprising the Luer lock fitting 3608, the control slider 3610, the slider handle 3618, the hemostasis valve 3622, the strain relief 3504, the catheter tubing to hub bond 3604, the activation sleeve 3430, the activation sleeve to slider bond 3614, and a plurality of seals 3612.

The proximal end of the annular sleeve 3430 is affixed to the tubular slider 3610 slidably disposed within the lumen 3616 of the catheter hub body 3602. The catheter hub 3600 comprises the sliding seals 3612, for example "O"-rings, within the inside diameter of the catheter hub body 3602 so that a fluid seal is maintained independent of axial location of the tubular slider 3610 within the catheter hub body 3602. A knob, button, trigger, handle, rotating collar, or the like 3618, can be affixed, or fabricated integral to, the tubular slider 3610 to advance or retract the tubular slider 3610 and the affixed sleeve 3430 relative to the catheter hub 3600 thus controlling the motion and the extents or limits of motion of the slider 3610 within the catheter hub body 3602. Referring to FIG. 34B, the motion of the proximal end of the mesh 3406, controlled by the sleeve 3430 is, thus, displacement limited at the catheter hub 3600 so that excess force cannot be exerted on the fragile slider 3412 to collar 3410 and collar 3410 to mesh 3406 attachments through the sleeve 3430. The catheter hub body 3602, the tubular slider 3610, or both, can comprise materials such as, but not limited to, polycarbonate, polysulfone, Grilamid®, polyurethane, ABS, and the like. The feature of displacement limited movement of the distal end of the annular sleeve 3430 relies on the annular sleeve 3430 having high column strength with insignificant compression and the catheter shaft 3402 having insignificant linear expansion under tension. The braided construction of the catheter shaft 3402 can help maintain low tensile elongation. Under 1 pound of linear force, the catheter 3402 stretch combined with the shortening of the annular sleeve 3430 needs to be less than a total of 0.10 inches.

FIG. 36B illustrates a side view of an activation guidewire 3440. In an exemplary embodiment, the activation guidewire 3440 comprises a proximal region 3630, a tapered transition zone 3632, an intermediate region 3634, a flexible region 3638, a pusher bump 3640, and a distal region 3642.

Referring to FIG. 36B, the proximal region diameter is about 0.014 inches, stepping down, at the tapered transition zone 3632 to a diameter of about 0.012 inches, further comprising a 0.014 inch diameter pusher bump 3640 proximate the distal end of the 0.012 diameter flexible region 3638, and then reducing to 0.009 to 0.011 inches in diameter for the distal most region 3642, which has a length of about 1 to 20 cm.

The length of the bump 3640 can range from about 0.010 inches to 0.100 inches or longer. The activation guidewire 3440 can comprise stainless steel, nitinol, fluoropolymer exterior layers, hydrophilic layers, and the like. The distal most 10 to 30 cm of length 3638 can comprise a wire stepdown to a diameter of approximately 0.001 to 0.006 inches. A coil of platinum, tantalum, stainless steel, or other wire can surround the flexible region 3638 located distally to the intermediate region 3634. The coil within the flexible region 3638 can comprise wire with diameters ranging from about 0.001 to 0.004 inches in diameter and the individual coils are preferably spaced with 0 to 2 wire diameters between coils. The built-up or composite construction of the activation guidewire 3440 can comprise an outer layer of FEP, PFA, PTFE, or the like that encapsulates the coil within the flexible region 3638. The coil composite structure can extend completely, or part-way into the distal most region 3642 and can comprise a change in coil wire thickness or spacing.

In another embodiment, the activation guidewire 3440 comprises a wire having a diameter of about 0.013 to 0.015 inches. In another embodiment, the activation guidewire 3440 comprises a main diameter of about 0.014 inches except for the distal most about 1 to 20 cm, which is stepped down to about 0.009 to 0.011 inches in diameter. In another embodiment, the activation guidewire 3440 comprises a proximal diameter of 0.012 inches, an about 0.013 to 0.015 inch diameter step up proximate the distal end of the 0.012 inch diameter, and then a distal most 0.09 to 0.011 inch diameter in the distal most 1 to 20 cm of guidewire.

Referring to FIGS. 36B and 35B, the proximal end of the activation guidewire 3440 can comprise a hub, permanently or removably affixed thereto similar to the cap 3510. The proximal end of the activation guidewire 3440 can comprise a hub further comprising a male Luer lock fitting 3512 that is reversibly lockable with a complimentary fitting 3506 on the proximal end of the catheter hub 3502. The position of the hub 3510 on the activation guidewire 3440 is selected and adjusted so that when the activation guidewire hub 3510 is fitted or engaged against the catheter hub 3502, the distal end of the 0.014 inch diameter portion of the wire or the bump 3640 is advanced a pre-determined amount to displace the slider 3412 a predetermined amount such that the entire system is displacement limited and cannot be overstressed by an overzealous operator.

FIG. 37A illustrates the distal end of a thrombectomy, occlusion removal, or flow restoration catheter 3400 comprising a slider coil 3412 having an increased length extending in the distal direction. The distal end 3702 of the slider coil 3412 is spaced apart from the radiopaque marker 3408 by the gap 3704. The purpose of the increased coil or slider 3412 is to provide a visual indicator of expansion of the mesh 3406 when viewed under fluoroscopy, because the mesh 3406, itself, is generally not visible under fluoroscopy, even in embodiments where the mesh 3406 is fabricated from metal because most spring metals have poor radiopacity.

FIG. 37B illustrates the distal end of the catheter 3400 of FIG. 37A having the extended length slider 3412. The slider 3412 has been advanced distally, under force, or displacement, exerted by the guidewire 3440 against the proximal end of the slider 3412. The expandable mesh 3406 has expanded radially as the slider 3412 pushes the collar 3410 distally. The collar 3410 is affixed to the proximal end of the mesh 3406. The mesh 3406 further comprises a plurality of radiopaque markers 3706 affixed proximate the longitudinal center of the mesh 3406. The gap 3704 between the distal end 3702 of the slider 3412 and the second radiopaque marker 3408 has reduced to substantially zero. The slider 3412 advantageously comprises radiopaque materials such as, but not limited to, platinum, gold, tantalum, platinum-iridium, and the like. The radiopaque materials can comprise the entire slider 3412 or a portion thereof. In an exemplary embodiment, the distal most 0.010 to 0.100 of the slider 3412 is radiopaque while the rest of the slider 3412 comprises malleable stainless steel, nitinol, or other substantially less radiopaque materials. The distal radiopaque part of the slider 3412 can be welded or crimped to the proximal, substantially non-radiopaque part of the slider 3412. The reduction in the gap 3704 can advantageously be used to allow the user to observe the amount of distal advance of the mesh, by viewing the system under fluoroscopy.

The plurality of radiopaque markers 3706 can be small beads or masses fabricated from materials such as, but not limited to, tantalum, platinum, platinum-iridium, gold, and the like, The plurality of radiopaque markers 3706 can have configurations that comprise loops of round or flat wire, split shot, beads having a central hole, or the like. The plurality of radiopaque markers 3706 are configured to detect, visualize, or illustrate, under fluoroscopy, the presence of, or the diametric or radial extent of, the expansion of the mesh 3406. In a preferred embodiment, the plurality of radiopaque markers number between 1 and 10 and preferably between 2 and 8 at a given axial location on the mesh. The plurality of radiopaque markers 3706 can be disposed at the center, the ends of the flat length, or both, of the mesh 3406.

Figure 38:
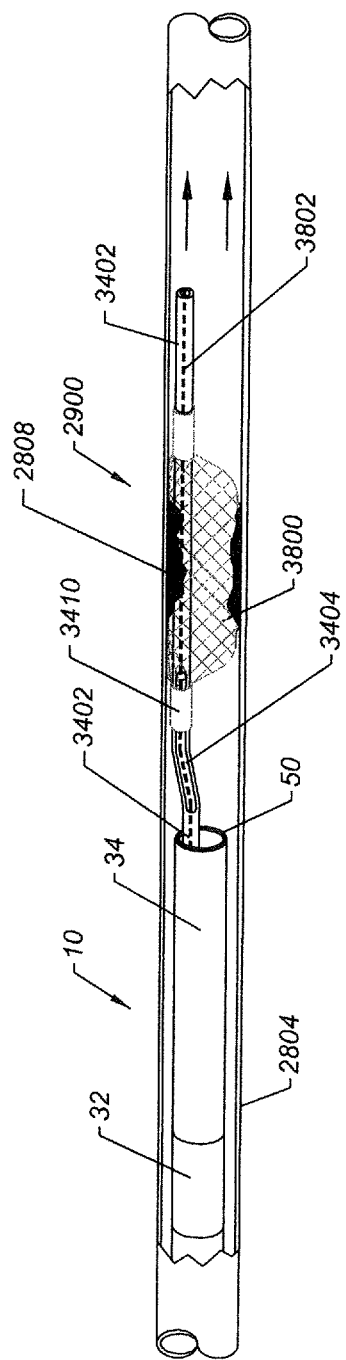
FIG. 38 illustrates the thrombectomy or flow restoration catheter deployed within a thrombus such that a mesh is asymmetrically expanded within the thrombus such that the catheter shaft resides closer to one side of the mesh than the other, according to an embodiment of the invention.

FIG. 38 illustrates a flow restoration catheter 2900 deployed within a thrombus 2808, which has become resident within the lumen of a blood vessel 2804. The flow restoration catheter 2900 has been advanced through an expandable guide catheter 10 further comprising a transition zone 32, a distal expandable region 34, and a slide dilator 50. The flow restoration catheter 2900 further comprises the window 3404, the sliding collar 3410, the expandable mesh 3800, and the catheter tubing 3402. The catheter tubing 3402 further comprises a length of longitudinally disposed wire or strand 3802 embedded or affixed thereto.

Referring to FIG. 38, the catheter tubing 3402 has deployed along the side of the vessel 2804 and is not centered therein. The expandable mesh 3800 has expanded asymmetrically but substantially has forced the thrombus open to generate a temporary flow lumen. The off-center access to the thrombus 2808 can be beneficial because passage through the thrombus 2808 may be obstructed centrally but more open on a side. The mesh 3800 has sufficient expansion capabilities to compensate for the off-center location of the main catheter tubing 3402. The main catheter tubing 3402 further is embedded with one or more stretch-resistant strands 3802. The stretch-resistant strands 3802 can range in diameter from 0.0005 to 0.005 inches in diameter or major dimension. The stretch-resistant strands 3802 can number between 1 and 10 and be circumferentially disposed about the catheter shaft 3402. The material used to fabricate the stretch-resistant strands 3802 can include, but not be limited to, stainless steel, tantalum, gold, platinum, platinum iridium, polyamide, polyimide, polyester, PEEK, polyurethane, or the like. A single strand 3802 is shown embedded within the tubing 3402 along its entire length, as in a co-extrusion or layup. The single strand 3802 passes on the other side of the tubing 3402 opposite the window 3404 so as to strengthen the tubing 3402 surrounding the window 3404.

FIG. 39A illustrates the thrombectomy or flow restoration catheter 3400 comprising the catheter shaft 3402, the slider 3412, the collar 3410, the collar to mesh bond 3418, the expandable mesh 3406, the catheter tube window 3404, and the proximal mesh to collar bond 3418. Also illustrated is an activation guidewire 3900 further comprising a slidable link 3902, a linkage lumen 3904, a deflector 3906, a side window 3908, and a distal link tip 3910.

Referring to FIG. 39A, the guidewire 3900 is sized to pass slidably through the central orifice or lumen of the slider 3412. The slidable link 3902 is slidably disposed within the linkage lumen 3904, integral to the guidewire 3900. The linkage lumen 3904 is terminated by the deflector 3906 which is integral or affixed to the guidewire 3900. The window 3908 is integral to the wall of the guidewire 3900 and operably connects the linkage lumen 3904 with the outside of the guidewire. When advanced distally, distal end 3910 of the slidable link 3902 is deflected laterally out the window 3908 such that it protrudes laterally out the side of the guidewire 3900. With the distal end 3910 protruding out through the window 3908, the activation guidewire 3900 engages the proximal end of the slider 3412 and can advance the slider distally when the guidewire 3900 is advanced distally, relative to the catheter shaft 3402. This type of activation guidewire 3900 can permit complete freedom of motion of the catheter tubing 3402 and the slider 3412 relative thereto, but, following extension of the distal end 3910, can be used to push on the slider 3412 to move the proximal bond 3418 distally and expand the mesh 3406.

FIG. 39B illustrates another embodiment of an activation guidewire 3920 disposed within the thrombectomy or flow restoration catheter 3400. The thrombectomy or flow restoration catheter 3400 comprises the catheter shaft 3402, the slider 3412, the collar 3410, the collar to mesh bond 3418, the expandable mesh 3406, the catheter tube window 3404, and the proximal mesh to collar bond 3418. The activation guidewire 3920 comprises a linkage 3922 disposed within a linkage lumen 3926, a distal end anchor 3924, and a plurality of outwardly bendable struts 3928.

As in FIG. 39A, the activation guidewire 3920 is configured to become larger in diameter or extend a portion laterally to engage the proximal end of the slider 3412 of the catheter 3400. The linkage 3922 is slidably disposed within the linkage lumen 3926 and is affixed to the distal portions of the guidewire by the anchor 3924. The struts 3928 are thin regions in the wall of the guidewire 3920 that bend outward when tension is applied on the linkage 3922 to pull it proximally relative to the guidewire 3920. The proximal tension on the linkage 3922 causes compression to be exerted on the struts 3928 causing them to bend outward in response. The guidewire 3920 and its components can all be fabricated from materials such as, but not limited to, stainless steel, nitinol, PTFE coatings, FEP coatings, PFA coatings, platinum-iridium, tantalum, and the like. A handle or tab (not shown) can be affixed to the proximal end of the linkage 3922 and the guidewire 3920 to permit and control relative motion therebetween. A jack-screw or other mechanical advantage type control can be disposed between the guidewire hub and the linkage hub to control and provide high force to generate motion therebetween.

Figure 40A:
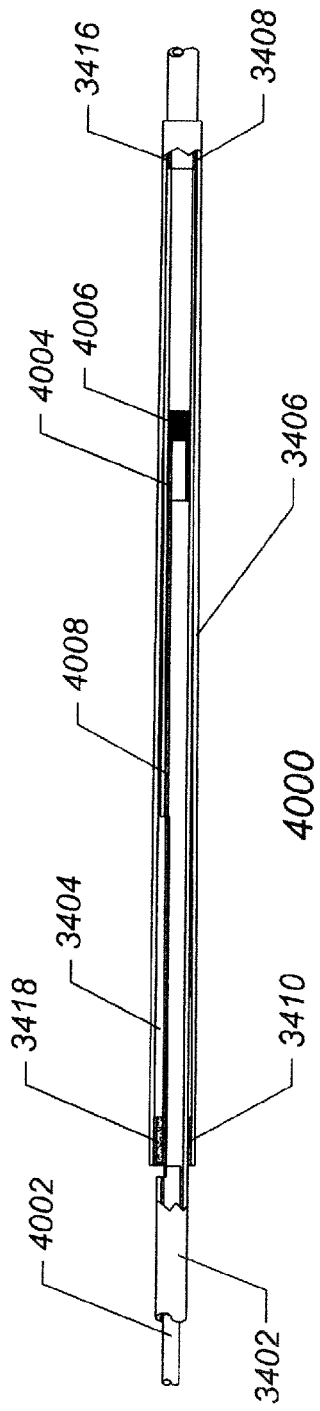
FIG. 40A illustrates a thrombectomy or flow restoration catheter comprising a standard, small diameter guidewire deployed therethrough and further comprising a short, tubular mesh slider deployed distally to a window in the catheter tubing wall, wherein the slider comprises a tail disposed proximally and affixed to a collar and the proximal end of the mesh through a window in the catheter tubing, according to an embodiment of the invention.

FIG. 40A illustrates a radially or laterally collapsed thrombectomy or flow restoration catheter 4000 comprising a catheter tube 3402, a window 3404, a proximal collar 3410, a slider tail 4008, a slider 4004, a slider radiopaque marker 4006, a distal mesh 3406 in its collapsed configuration, a distal mesh radiopaque marker 3408, a distal mesh bond 3416, and a large diameter commercial guidewire 4002.

Referring to FIG. 40A, the commercial guidewire 4002 is being advanced distally and has just reached the window 3404 in the catheter tubing 3402. The mesh 3406 is elastomeric, shape memory, or superelastic, and is biased to its maximum length, minimum diameter configuration by its own intrinsic restorative forces.

Figure 40B:
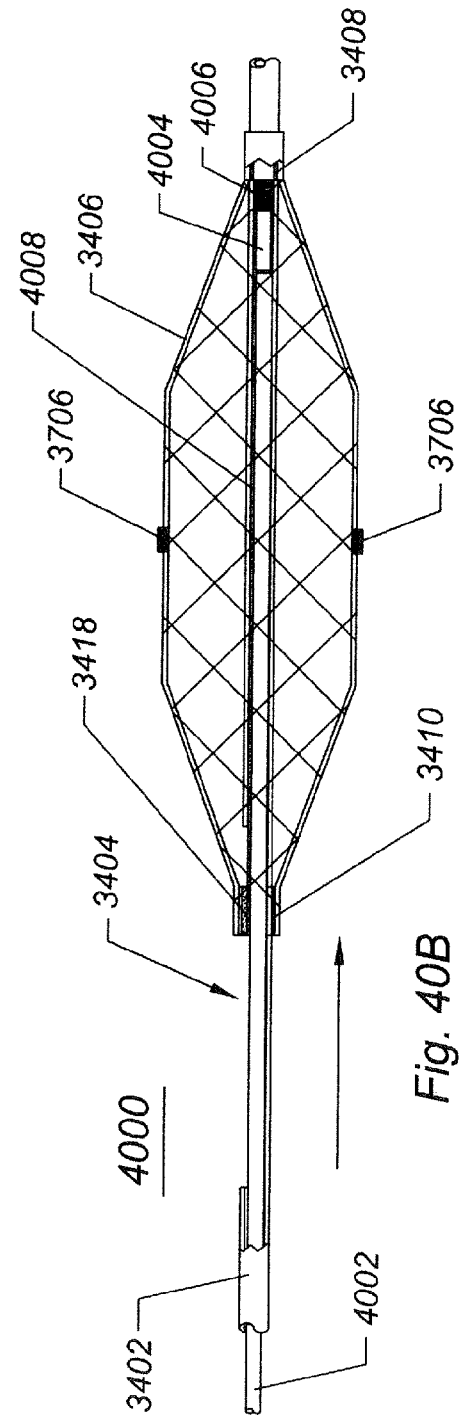
FIG. 40B illustrates the thrombectomy or flow restoration catheter of FIG. 40A, comprising a standard, large diameter activation guidewire and a modified ring and tail slider for moving the proximal end of the mesh, wherein the activation guidewire has been advanced distally to expand the mesh, according to an embodiment of the invention.

FIG. 40B illustrates a radially or diametrically expanded thrombectomy or flow restoration catheter 4000 comprising a catheter tube 3402, a window 3404, a proximal collar 3410, a slider tail 4008, a slider 4004, a slider radiopaque marker 4006, a distal mesh 3406 in its expanded configuration, a distal mesh bond radiopaque marker 3408, a plurality of mesh extent radiopaque markers 3706, a distal mesh bond 3416, and a large diameter commercial guidewire 4002.

Referring to FIG. 40B, the guidewire 4002 has been advanced distally to just contact the proximal end of the slider 4004, which is smaller in inside diameter than the outside diameter of the guidewire 4002. The slider radiopaque marker 4006 is affixed to the distal end of the slider 4004. The slider tail 4008 is affixed, or integral to, the proximal end of the slider 4004. In a preferred embodiment, the slider tail 4008 and the slider 4004 are integrally formed from a single length of hypodermic tube (hypo tube). The sides of the hypo tube are partially cut away to form the tail structure 4008 while the region where the hypotube is not cut away forms the axially elongate cylindrical slider 4004. The slider 4004 and the slider tail 4008 can be fabricated from materials including, but not limited to, stainless steel, platinum, gold, tantalum, cobalt nickel alloy, titanium, nitinol, and the like. The slider radiopaque marker 4006 can be fabricated from materials including, but not limited to, platinum, platinum iridium, tantalum, gold, barium or bismuth salts, or the like. The slider radiopaque marker 4006 can be fabricated from round or flat wire formed into a coil, with the wire having a width or diameter of approximately 0.002 inches and ranging from about 0.0005 to 0.005 inches.

The guidewire, typically having a diameter ranging from about 0.012 to 0.018 inches has been advanced distally past the slider tail 4008, which places some off-center forces on the guidewire 4002 but still permits the guidewire 4002 to pass. The guidewire 4002 is advanced distally until it abuts the proximal end of the slider 4004, after which it forces the slider 4004 distally to shorten the mesh 3406 and expand the mesh 3406 diametrically. Since the slider 4004 is distal to the window 3404, the guidewire 4002 is not coerced to exit through the window since it has already passed the window when it contacts the slider 4004. Furthermore, the slider tail 4008 serves as a moving blockade to prevent the guidewire 4002 from exiting the window 3404. In an exemplary embodiment, the inside diameter of the slider 4004 can be about 0.012 inches. In an exemplary embodiment, the inside diameter of the catheter tubing 3402 can range from about 0.016 to about 0.017 inches.

FIG. 41A illustrates the unexpanded, expandable guide catheter 10 deployed within the lumen 2802 of the blood vessel 2804. The expandable guide catheter 10 further comprises the proximal non-expandable region 33, a transition zone 32, a distal, expandable region 34, the slide dilator 50 further comprising the lumen 38, the guidewire 2614, the nose cone 2708 further comprising the central lumen 2828, and a ribcage reinforcing structure 4100.

Referring to FIG. 41A, the ribcage reinforcing structure 4100 is embedded within the wall of the distal region 34, the transition zone 32, and optionally a portion or substantially all of the proximal region 33. The ribcage reinforcing structure 4100 can be fabricated from malleable materials such as, but not limited to, tantalum, stainless steel, titanium, gold, platinum, platinum-iridium, cobalt nickel alloy, or the like. The ribcage reinforcing structure 4100 can be compressed to circumferentially surround the majority of the distal region 34, or a portion thereof. The ribcage reinforcing structure 4100 can be configured to not be fully embedded within any polymer surround of the distal region 34 such that the ribs can slide circumferentially upon expansion of the distal region 34 and the transition zone 32. The ribcage 4100 can provide pushability and torqueability to the system. In this diametrically collapsed configuration, the distal region 34 can retain significant flexibility and navigability through tortuous vasculature and can be advanced over the guidewire 2614.

FIG. 41B illustrates the expandable guide catheter 10 of FIG. 41A with the distal region 34 expanded to its maximum operating diameter. The guide catheter 10 comprises the proximal region 33, the transition zone 32, the dilator 50 further comprising the central lumen 38, the guidewire 2614, and the ribcage reinforcement 4100 of FIG. 41A further comprising the longitudinally oriented spine 4104 and the ribs 4102. The guide catheter 10 is deployed within the blood vessel 2804 further comprising the lumen 2802.

Referring to FIG. 41B, the distal region 34 is expanded by distal advancement of the slide dilator 50 causing the central lumen 38 of the dilator 50 to comprise the effective central lumen of the guide catheter 10. The ribs 4102 of the ribcage 4100 have opened up to form "C"-shaped structures. The balance of the distal cross-section 34 is comprised by polymeric material within which or against which the ribcage 4100 is affixed. The fixation of the ribcage 4100 to the polymeric material is such that the ribs are able to move circumferentially relative to the polymeric material comprised by the distal region 34. The ribcage 4100 has opened up diametrically, or radially, such that it now describes a larger diameter arc than in its collapsed configuration, as illustrated in FIG. 41A. The ribcage 4100 provides substantial support to a portion of the distal region 34 in both the longitudinal and circumferential directions. This support may be important when sliding the dilator 50 distally to expand and proximally to contract the distal region 34.

Figure 42A:
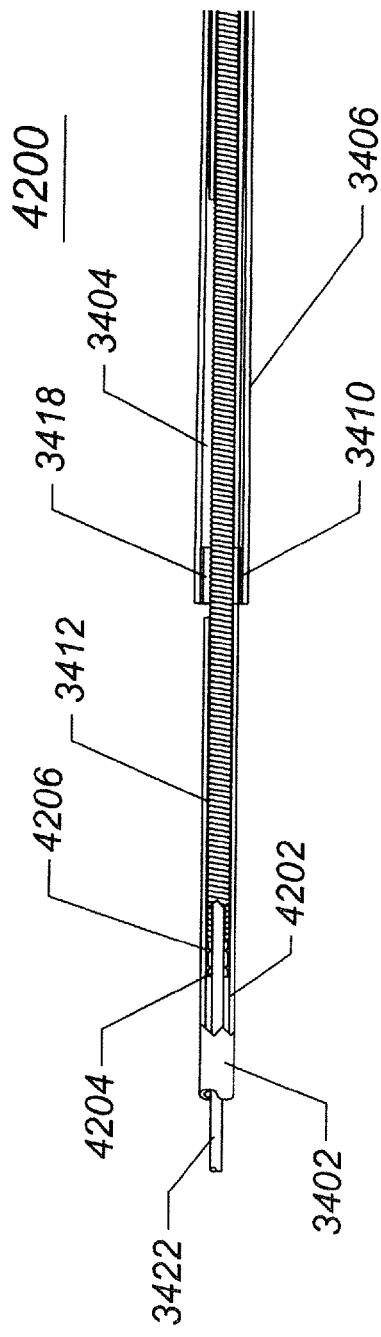
FIG. 42A illustrates a region of a thrombectomy or flow restoration catheter wherein the proximal end of the mesh is affixed to a hydraulic plunger annularly placed between the guidewire and the inside diameter of the catheter tubing, according to an embodiment of the invention.

FIG. 42A illustrates, in side cross-section and partial breakaway view, a region surrounding the proximal end of the expandable mesh 3406 of a thrombectomy or flow restoration catheter 4200 having hydraulic activation means. The catheter 4200 comprises the catheter tubing 3402, the slider or traveler 3412, the expandable mesh 3406, the collar 3410, the mesh to collar bond 3418, the window or skive 3404, a hydraulic plunger 4204, a catheter lumen 4202, one or more plunger seals 4206, and a guidewire 3422.

Referring to FIG. 42A, the guidewire 3422 is configured to slidably move within the catheter lumen 4202, the hydraulic plunger 4204, and the slider 3412. The slider 3412 is advantageously configured to be highly flexible but retain column strength. In an exemplary embodiment, the slider 3412 is a closed coil spring, as illustrated and can further comprise a backbone (not shown) running axially and affixed thereto at one or more points. The hydraulic plunger 4204 seals around the guidewire 3422, which can be an about 0.010 inch diameter guidewire, or similar, and capable of passing entirely through the system without restriction. The hydraulic plunger 4204 is affixed to the slider 3412 by welding, adhesive bonding, mechanical fastening, or the like.

Pressurization of the catheter lumen 4202, which forms an annulus between the catheter tubing 3402 and the guidewire 3422, transmits pressure energy along the catheter length from the proximal end to the point of the hydraulic plunger 4202. Pressure can be applied at the proximal end of the catheter 4200 through a fluid infusion port 3608, as illustrated in FIG. 36 and be transmitted through the catheter lumen 4202. The hydraulic plunger 4202, which slidably seals to the catheter tubing 3402 and the guidewire 3422 prevents escape of fluid pressure out the distal end of the catheter 4200.

Figure 42B:
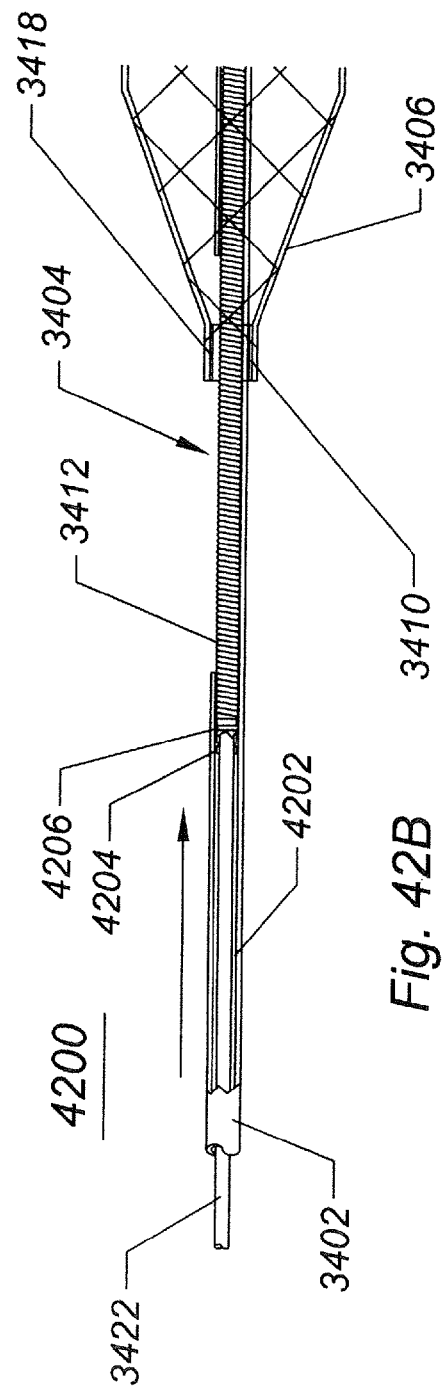
FIG. 42B illustrates the thrombectomy or flow restoration catheter of FIG. 42A wherein the annulus between the guidewire and the catheter inside diameter has been pressurized, forcing the hydraulic plunger to advance distally and resulting in diametric expansion of an expandable mesh element, according to an embodiment of the invention.

FIG. 42B illustrates the catheter 4200 with pressure applied to the catheter tubing lumen 4202 and with the hydraulic plunger 4204 advanced distally to approximately a limit point. The catheter 4200 comprises the catheter tubing 3402, the slider or traveler 3412, the expandable mesh 3406, the collar 3410, the mesh to collar bond 3418, the window or skive 3404, the hydraulic plunger 4204, the catheter lumen 4202, one or more plunger seals 4206, and the guidewire 3422.

Referring to FIG. 42B, the slider 3412 is affixed to the collar 3410, which is further affixed to the proximal end of the expandable mesh 3406, said proximal end of the expandable mesh 3406 being free to move axially to the extent the window 3404 permits. The amount of pressure applied can range between 1 PSI and 5,000 PSI depending on the surface area of the hydraulic plunger 4204. Application of pressure forces the mesh 3406 to become axially compressed, thus increasing its diameter. The mesh 3406 can be fabricated from spring materials such as, but not limited to, nitinol, titanium, cobalt-nickel alloy, stainless steel, and the like. The mesh 3406 can be advantageously biased toward its diametrically compressed, axially elongated configuration. Release or evacuation of the fluid pressure, preferably generated by infusion of saline or radiopaque contrast dye or the like, permits the expandable mesh 3406, to return to its diametrically unexpanded, unstressed state.

In certain embodiments, methods of use are enabled by utilization of the devices disclosed herein. In some embodiments, the vasculature is accessed by a percutaneous or surgical incision into the groin. In a percutaneous method, a hollow, 18-gauge needle is inserted into a femoral or iliac artery, following which a guidewire is inserted through the hollow lumen of the needle and routed into the vasculature. The needle is next removed and an access sheath can be inserted over the guidewire and into the vasculature. The access sheath is typically terminated, at its proximal end, with a hemostasis valve to prevent loss of blood or influx of air into the vasculature. The expandable guide catheter can next be inserted into the vasculature through the access sheath or the expandable guide catheter can form the access sheath itself, without the need for a separate access sheath. The expandable guide catheter is next routed, along with the guidewire up the aorta toward the head of the patient. Interaction between a J-tip guidewire and the expandable guide catheter can be used for steering and manipulation of the expandable guide catheter into the carotid arteries or vertebral arteries. The extremely flexible distal end of the unexpanded, expandable guide catheter facilitates steering in conjunction with various guidewire distal end configurations since it can be made straight or curved with relative ease. The expandable guide catheter can be advanced through extremely tortuous vasculature such as that found in the carotid siphon or the basilar artery and adjacent vessels such that the expandable guide catheter can be advanced with its distal end resident within the circle of Willis. Once the expandable guide catheter is positioned within the cerebrovasculature proximate a target lesion, the guidewire can be removed. The expandable guide catheter can next be expanded by distal advancement of the translation dilator. The dilator remains in place during the procedure. If, as in another embodiment, a balloon dilator is used to expand the distal end of the expandable guide catheter, the balloon dilator is next deflated and removed to expose the central lumen for catheter access therethrough.

In certain embodiments where blood flow re-establishment or clot removal is indicated, a therapeutic catheter, such as is described herein, is advanced through the central lumen of the expandable guide catheter toward the target lesion. Expandable elements at the distal end of the therapeutic catheter are maintained in their radially collapsed configuration to minimize diametric profile during catheter advance. In certain embodiments, the therapeutic catheter is advanced with a guidewire inserted through the central lumen to maintain a diametrically collapsed configuration. The distal end of the therapeutic catheter is advanced through or across the obstruction. The obstruction can be a thrombus, clot, bolus of embolic material, misplace device, or the like. The distal end of the therapeutic catheter can next be deployed, or diametrically expanded, by removing the guidewire proximally, causing the biased therapeutic catheter tubing within the expandable distal end to become distorted into a serpentine or coil shape, thus shortening the length of an expandable element and increasing its radius, diameter, cross-section, or other lateral dimension. In embodiments where the expandable element is expanded within the obstruction, blood flow can be acutely re-established. Thrombolytic agents can be infused through vents within the expandable element, if desired, to dissolve, or assist with removal of, any thrombus. In embodiments where the therapeutic device is an expandable mesh, malecot, coil, or other device, the expandable element is configured so as not to be damaging to the vessel wall or intima.

In other embodiments, or in a further procedure using the same embodiment of the device, the expandable element of the therapeutic catheter can be radially collapsed, or re-collapsed, by distal advancement of the guidewire therethrough, and positioned on the other side (instrumentally distal) of the obstruction from the location of the distal end of the expandable guide catheter. The mesh can be next expanded by proximal withdrawal of the guidewire. The therapeutic catheter can then be withdrawn proximally toward the distal end of the expandable guide catheter such that the expandable element engages the obstruction or clot and withdraws it toward and into the open end of the expandable guide catheter, wherein it can be removed from the body. Vacuum, or suction, can be applied to the lumen of the expandable guide catheter to provide aspiration effects to facilitate withdrawal of the obstruction into the lumen of the expandable guide catheter. The therapeutic catheter can be pulled proximally through and out of the expandable guide catheter to remove the thrombus or obstruction after which it can be re-inserted for follow-up therapeutic procedures. The expandable guide catheter can be removed from the body, preferably following proximal retraction of the translation dilator from the expandable distal end to increase flexibility and suppleness of the distal end. The expandable distal end of the expandable guide catheter can become flaccid with the same diameter or it can resiliently bias to a smaller diameter by the urging of elastomeric elements disposed therein. The expandable guide catheter can, in other method embodiments be withdrawn with the dilator retracted proximally and the therapeutic catheter with trapped obstruction enclosed, or partially enclosed, within its lumen.

In other embodiments, the devices and methods disclosed herein can be configured or dimensioned for use throughout the vasculature, including the coronary and peripheral vasculature, the gastrointestinal tract, the urethra, ureters, Fallopian tubes, biliary tract ducts, and other body lumens and potential lumens.

In other embodiments, the devices and methods disclosed herein can be configured to elute drugs from a mesh or temporary stent. In some embodiments, the mesh, or expandable element, which can be termed a temporary stent, can be coated with a layer of polymer such as, but not limited to, Parylene, polyurethane, polyglycolic acid (PGA), polylactic acid (PLA), collagen, synthetic Glycocalix, phosphorylcholine, or the like. The polymer layer can be impregnated with pharmaceutical agents such as, but not limited to, anti-cancer drugs, anti-inflammatory drugs, antimicrobial drugs, antibiotics, thrombolytic agents, or the like. Over time, the drugs contained by the polymer layer can be designed to equilibrate or migrate out of the polymer layer and into the tissue, the bloodstream, or both. The drugs or other pharmacological agents can be directed to perform tasks such as, but not limited to, retardation of tissue hyperplasia, retardation of thrombus buildup, dissolution of thrombus buildup, and the like.

In other embodiments, the expandable structure or temporary stent can be configured to be covered with a polymeric coating, a polymeric membrane, a covering, or the like which spans elements of the expandable structure. The covering can comprise a monolayer of polymer or it can comprise a fabric such as a weave, knit, braid, or the like of materials such as, but not limited to, polyester (e.g. Dacron®), polyimide, polyamide, Hytrel, Pebax, or the like. The fabric or cloth covering can be further coated or embedded with polymeric material such as, but not limited to, polyurethane, silicone elastomer, thermoplastic elastomer, or the like. The pores in the fabric can be configured to be open with spaces up to 1-mm or larger therebetween, or the pores can be substantially closed.

The expandable region can be configured to open regions of thrombus in the vasculature, including in the coronary arteries or the cerebrovasculature. Such ability to open regions that have become partially or completely occluded with thrombus, clot, or atheroma provides a temporary flow restoration device or stent. The unexpanded device is first advanced through the thrombus such that it substantially spans the thrombus region, following which the device is expanded diametrically to open the thrombotic region and allow fluid, such as for example blood, flow to resume therein. In some embodiments, the apparatus, devices, methods, and procedures can be used to open clots or thrombus, which blocks the lumen of stents or stent-grafts implanted within a body vessel or lumen. The devices and methods can be advantageously used to open blockages in stents, neck bridges, or other devices placed within the cerebrovasculature, neurovasculature, and coronary vasculature.

Such an expandable structure delivered by a catheter can be used following percutaneous transluminal coronary angioplasty (PTCA), plain old balloon angioplasty (POBA), or stenting in the coronary arteries or neurovasculature to deliver drugs to treat or prevent restenosis, reduce or treat inflammation, etc. The device for drug delivery comprises fluid delivery lumens within the catheter that are operably connected to injection ports on the catheter hub and operably connected to openings in the catheter proximate the distal end of the catheter or proximate the expandable region. Drugs delivered by the device which can serve as platelet inhibitors include, but are not limited to, ticlopidine, clopidogrel, aspirin, and the like. Drugs delivered by the device can be used to treat restenosis and those drugs include, but are not limited to, sirolimus, paclitaxel, methotrexate, everolimus, Biolimus A9, zotarolimus, and the like, and are generally of a group of drugs used for anti-cancer therapy. Drugs used to treat inflammation include, but are not limited to, aspirin, ibuprofen, naproxen sodium, steroids, and the like. Drugs used to treat vessel cramping or vasoapasm include papavarine, or the like. Drugs used to treat thrombosis include, but are not limited to, tissue plasminogen activator, streptokinase, urokinase, lysokinase; staphylokinase, agents that convert plasminogen to fibrinolysin; fibrinolysin; fibrin modulatin, and the like.

In another embodiment of the methods of use, the catheter can be used to perform temporary neck remodeling of aneurysms or other vascular lesions. Often during coil embolization of aneurysms, the aneurismal necks encountered are considered wide, necessitating the need for a neck-bridging device such as a temporary micro-balloon or an implantable stent. These neck-bridging devices hold the coils in place to prevent them from dropping into the parent vessel during delivery. Balloons conform to the inner surface of the vessel wall and provide a smooth surface against the coils, but seal the vessel from blood flow for perhaps long durations, such sealing having potentially catastrophic ischemic consequences if sustained for too long a time. After filling the aneurysm with coils these micro-balloons are deflated and removed for the vasculature. Neurological stents are permanent implants that can bridge the neck during the coiling procedure, they are expensive and non-retrievable, but allow blood flow through them. The design/method concept disclosed herein would be to employ the microcatheter with the expandable element positioned across the neck oft he aneurysm and radially expand the element to provide the neck bridge. The element in this case could be provided with a non-porous surface about the cylindrical outer surface portion enabling a smoother, non-open surface against the delivered embolization coils. Other embodiments can comprise a window, a skive, a hole, or a breach in the medial or distal portion of the catheter to allow the introduction of a coil deliver micro-catheter (coaxially) into the aneurysm. In this embodiment, the catheter system may be slightly larger (3-Fr to 5-Fr) than the up to 3-Fr diameter typical microcatheter.

It is to be appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless otherwise specified of if to do so would render the embodiment or example unsuitable for its intended use. Also, where the steps of a method or process have been described or listed in a particular order, the order of such steps may be changed unless otherwise specified or unless doing so would render the method or process unworkable for its intended purpose. All reasonable additions, deletions, modifications and alterations are to be considered equivalents of the described examples and embodiments and are to be included within the scope of the following claims.

What is claimed is:

1. A catheter system comprising;
   a guide catheter;
   an embolectomy catheter comprising;
   an outer shaft characterized by a proximal end and a distal end, said outer shaft having a first lumen extending from the proximal end to the distal end thereof, said lumen having a first diameter;
   an inner, distal shaft characterized by a proximal end and a distal end, said inner, distal shaft disposed within the outer shaft, said inner, distal shaft having a second lumen having a second diameter, said second lumen extending from the proximal end to the distal end of said inner, distal shaft, and a constriction disposed within said second lumen of the inner distal shaft;
   an expandable member characterized by a proximal end and a distal end, said expandable member secured at its proximal end to the distal end of the outer shaft and secured at its distal end to the distal end of the inner, distal shaft;
   wherein the expandable member is expanded and contracted by relative movement of the outer shaft and the inner, distal shaft, and
   wherein the constriction is characterized by an inner diameter which is less than the second diameter of the lumen of the inner distal shaft.

2. The catheter system of claim 1, wherein the constriction inner diameter is sized to frictionally engage a guidewire which has an outer diameter smaller than the diameter of the second lumen of the inner distal shaft.

3. The catheter system of claim 1, wherein the guide catheter further comprises a flared distal opening.

4. The catheter system of claim 1, wherein the guide catheter further comprises a flared distal opening, said flared distal opening comprising a radially expandable shape memory element.

5. The catheter system of claim 1, further comprising a cover disposed on a distal portion of the expandable member, said cover being impermeable to liquids.

6. The catheter system of claim 1, further comprising a cover disposed on the entirety of the expandable member, said cover being impermeable to liquids.

7. The catheter system of claim 1, wherein the inner, distal shaft is characterized by an aperture communicating from the lumen to the exterior of the inner, distal shaft, said aperture disposed within the expandable member.

8. The catheter system of claim 1, wherein the inner, distal shaft terminates proximally within the distal end of the outer shaft.

9. The catheter system of claim 1 wherein the expandable member takes on a first, unexpanded configuration when the inner distal shaft is in a first position relative to the outer shaft and takes on a second, expanded configuration when the inner distal shaft is moved to a second position, proximal to the first position, relative to the outer shaft.

10. The catheter system of claim 1, wherein the expandable member is self-expandable, and has a first, small diameter configuration when tensioned by a guidewire inserted into the constriction and a second, large diameter configuration when not tensioned by a guidewire disposed in the constriction.

11. A catheter system comprising;
    a guide catheter;
    an embolectomy catheter comprising;
    an outer shaft characterized by a proximal end and a distal end, said outer shaft having a first lumen extending from the proximal end to the distal end thereof, said lumen having a first diameter;
    an inner, distal shaft characterized by a proximal end and a distal end, said inner, distal shaft disposed within the outer shaft, extending distally from the distal end of the outer shaft and terminating proximally within the distal end of the outer shaft, said inner, distal shaft having a second lumen having a second diameter, said second lumen extending from the proximal end to the distal end of said inner, distal shaft, and a constriction disposed within said second lumen of the inner distal shaft;
    an expandable member characterized by a proximal end and a distal end, said expandable member secured at its proximal end to the distal end of the outer shaft and secured at its distal end to the distal end of the inner, distal shaft;

wherein the expandable member is expanded and contracted by relative movement of the outer shaft and the inner, distal shaft, and wherein the constriction is characterized by an inner diameter which is less than the second diameter of the lumen of the inner distal shaft, and said inner diameter is sized to frictionally engage a guidewire which has an outer diameter smaller than the diameter of the second lumen of the inner distal shaft.

12. The catheter system of claim 11, wherein the guide catheter further comprises a flared distal opening.

13. The catheter system of claim 11, wherein the guide catheter further comprises a flared distal opening, said flared distal opening comprising a radially expandable shape memory element.

14. The catheter system of claim 11, further comprising a cover disposed on a distal portion of the expandable member, said cover being impermeable to liquids.

15. The catheter system of claim 11, further comprising a cover disposed on the entirety of the expandable member, said cover being impermeable to liquids.

16. The catheter system of claim 11, wherein the inner, distal shaft is characterized by an aperture communicating from the lumen to the exterior of the inner, distal shaft, said aperture disposed within the expandable member.

17. The catheter system of claim 11 wherein the expandable member takes on a first, unexpanded configuration when the inner distal shaft is in a first position relative to the outer shaft and takes on a second, expanded configuration when the inner distal shaft is moved to a second position, proximal to the first position, relative to the outer shaft.

18. The catheter system of claim 11, wherein the expandable member is self-expandable, and has a first, small diameter configuration when tensioned by a guidewire inserted into the constriction and a second, large diameter configuration when not tensioned by a guidewire disposed in the constriction.

* * * * *